US011390655B2

(12) United States Patent
Sievers et al.

(10) Patent No.: US 11,390,655 B2
(45) Date of Patent: Jul. 19, 2022

(54) MODIFIED CHIMERIC ANTIGEN RECEPTORS AND METHODS OF USE

(71) Applicant: Kite Pharma, Inc., Santa Monica, CA (US)

(72) Inventors: Stuart A. Sievers, Van Nuys, CA (US); Jed J. W. Wiltzius, Woodland Hills, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 121 days.

(21) Appl. No.: 16/192,492

(22) Filed: Nov. 15, 2018

(65) Prior Publication Data

US 2019/0144515 A1    May 16, 2019

Related U.S. Application Data

(60) Provisional application No. 62/587,336, filed on Nov. 16, 2017.

(51) Int. Cl.
| | | |
|---|---|---|
| *C07K 14/47* | (2006.01) | |
| *C12N 15/62* | (2006.01) | |
| *C07K 16/28* | (2006.01) | |
| *C07K 14/705* | (2006.01) | |
| *C07K 14/725* | (2006.01) | |
| *C12N 5/0783* | (2010.01) | |

(52) U.S. Cl.
CPC ...... *C07K 14/4748* (2013.01); *C07K 14/7051* (2013.01); *C07K 14/70521* (2013.01); *C07K 16/2878* (2013.01); *C12N 15/62* (2013.01); *C07K 2317/31* (2013.01); *C07K 2317/53* (2013.01); *C07K 2317/55* (2013.01); *C07K 2319/03* (2013.01); *C07K 2319/75* (2013.01); *C07K 2319/91* (2013.01); *C12N 5/0638* (2013.01)

(58) Field of Classification Search
CPC ............ C07K 2319/75; C07K 2319/33; C07K 2319/03
USPC ..................................... 424/133.1; 530/387.3
See application file for complete search history.

(56) References Cited

U.S. PATENT DOCUMENTS

| | | | |
|---|---|---|---|
| 5,728,388 A | 3/1998 | Terman et al. | |
| 5,827,642 A | 10/1998 | Riddell et al. | |
| 5,830,462 A | 11/1998 | Crabtree et al. | |
| 5,834,266 A | 11/1998 | Crabtree et al. | |
| 5,869,337 A | 2/1999 | Crabtree et al. | |
| 6,040,177 A | 3/2000 | Riddell et al. | |
| 6,165,787 A | 12/2000 | Crabtree et al. | |
| 6,319,494 B1 | 11/2001 | Capon et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,709,226 B2 | 5/2010 | Foote et al. | |
| 7,741,465 B1 | 6/2010 | Eshhar et al. | |
| 8,349,791 B2* | 1/2013 | Slusky .................... A61P 35/00 514/1.1 |
| 8,486,693 B2 | 7/2013 | Park et al. | |
| 10,597,456 B2* | 3/2020 | Wiltzius .................. A61P 37/08 |
| 11,118,168 B2* | 9/2021 | Shah ............... C07K 14/70521 |
| 2002/0006409 A1 | 1/2002 | Wood et al. | |
| 2004/0014194 A1 | 1/2004 | Beyer et al. | |
| 2011/0286980 A1 | 11/2011 | Brenner et al. | |
| 2012/0130076 A1 | 5/2012 | Holt et al. | |
| 2013/0287748 A1 | 10/2013 | June et al. | |
| 2014/0050708 A1 | 2/2014 | Powell et al. | |
| 2014/0099309 A1 | 4/2014 | Powell et al. | |
| 2014/0154228 A1 | 6/2014 | Volk et al. | |
| 2014/0171649 A1 | 6/2014 | Li et al. | |
| 2014/0227237 A1 | 8/2014 | June et al. | |
| 2014/0286987 A1 | 9/2014 | Spencer et al. | |
| 2015/0266973 A1 | 9/2015 | Jarjour et al. | |
| 2016/0046700 A1 | 2/2016 | Foster et al. | |
| 2017/0283500 A1* | 10/2017 | Wiltzius .................. A61P 19/02 |
| 2017/0283504 A1* | 10/2017 | Wiltzius .................. A61P 35/00 |
| 2018/0280437 A1* | 10/2018 | Wiltzius .................. A61K 35/17 |
| 2018/0312588 A1* | 11/2018 | Wiltzius ............. C07K 14/7051 |
| 2018/0362940 A1* | 12/2018 | Shah ....................... A61P 35/00 |
| 2020/0108142 A1* | 4/2020 | Wiltzius ............... C07K 16/245 |
| 2020/0109209 A1* | 4/2020 | Wiltzius ................. A61K 45/06 |
| 2020/0115457 A1* | 4/2020 | Wiltzius ................. A61P 37/08 |
| 2020/0246382 A1* | 8/2020 | Perez ....................... A61P 35/02 |
| 2021/0163606 A1* | 6/2021 | Burman ............ A61K 39/3955 |
| 2021/0324350 A1* | 10/2021 | Shah ................ C07K 14/70592 |

FOREIGN PATENT DOCUMENTS

| | | |
|---|---|---|
| WO | WO-2008/081035 | 7/2008 |
| WO | WO-2012/031744 A1 | 3/2012 |
| WO | WO-2012/033885 | 3/2012 |
| WO | WO-2012/079000 | 6/2012 |
| WO | WO-2012/129514 | 9/2012 |

(Continued)

OTHER PUBLICATIONS

MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al. ((2007) Mol. Immunol. 44: 1075-1084).*
Chen et al. J. Mol. Bio. (1999) 293, 865-881.*
Wu et al. (J. Mol. Biol. (1999) 294, 151-162).*
Ward et al. (Nature 341:544-546 (1989)).*
Smith-Gill et al. (J. Immunol. 139:4135-4144 (1987)).*

(Continued)

*Primary Examiner* — Lynn A Bristol

(57) ABSTRACT

The disclosure provides a chimeric antigen receptor (CAR) comprising a modified hinge, transmembrane and/or intracellular domain disclosed herein. Some aspects of the disclosure relate to a polynucleotide encoding a chimeric antigen receptor (CAR) comprising the costimulatory domain disclosed herein. Other aspects of the disclosure relate to cells comprising the CAR and use in a T cell therapy.

6 Claims, 16 Drawing Sheets

Specification includes a Sequence Listing.

(56) References Cited

FOREIGN PATENT DOCUMENTS

| WO | WO-2014/127261 | 8/2014 |
|---|---|---|
| WO | WO-2014/186469 | 11/2014 |
| WO | WO-2015/080981 | 6/2015 |
| WO | WO-2015/090229 | 6/2015 |
| WO | WO-2015/142675 | 9/2015 |
| WO | WO-2016/014565 | 1/2016 |
| WO | WO-2016/044745 | 3/2016 |
| WO | WO-2016/090369 | 6/2016 |

OTHER PUBLICATIONS

Kumar et al. (J. Biol. Chem. 275:35129-35136 (2000)).*
Song et al. (Biochem Biophys Res Comm 268:390-394 (2000)).*
Alabanza et al (Mol. Ther. Nov. 1, 2017;25(11):2452-2465. Epub Jul. 27, 2017).*
Kunin et al. (American Univeristy Law Review 51(4): 609-638, Art. 2 (Apr. 2002)).*
Henry etal (Frontiers in Immunology 8:1-15 (Dec. 12, 2017).*
Kim etal. (Biochimica et Biophysica Acta 1844 (2014) 1983-2001).*
U.S. Appl. No. 62/167,750, Bot et al.
U.S. Appl. No. 62/262,143, Bot et al.
Al-Lazikani, B. et al., "Standard conformations for the canonical structures of immunoglobulins" Journal of Molecular Biology, 273(4): 927-948 (1997).
Bricogne, G. "Direct phase determination by entropy maximization and likelihood ranking: status report and perspectives", Acta Crystallogr D Biol Crystallogr 49(Pt 1): 37-60 (1993).
Bricogne, G. "[23] Bayesian statistical viewpoint on structure determination: Basic concepts and examples", Meth Enzymol, 276A: 361-423 (1997).
Champe, M. et al., "Monoclonal Antibodies That Block the Activity of Leukocyte Function-associated Antigen 1 Recognize Three Discrete Epitopes in the Inserted Domain of CD11a", J Biol Chem, 270(3): 1388-94 (1995).
Cheung et al., "Epitope-specific antibody response to the surface antigen of duck hepatitis B virus in infected ducks", Virology, 176(2): 546-552 (1990).
Chothia, C. et al., "Canonical structures for the hypervariable regions of immunoglobulins", J Mol Biol, 196: 901-917 (1987).
Chothia, C. et al., "Structural repertoire of the human VH segments" J Mol Biol, 227: 799-817 (1992).
Cunningham et al., "High-resolution epitope mapping of hGH-receptor interactions by alanine-scanning mutagenesis", Science 244(4908): 1081-85 (1989).
Dayhoff et al., "Atlas of Protein Sequence and Structure: A Model of Evolutionary Change in Proteins", 5: 345-352 (1978).
Devereux et al., "A comprehensive set of sequence analysis programs for the Vax", Nucl. Acid Res., 12: 387 (1984).
Eshhar et al., "Tumor-specific T-bodies: towards clinical application", Cancer Immunol Immunotherapy, 45(3-4): 131-136 (1997).
Fegan et al., "Chemically controlled protein assembly: techniques and applications", Chem. Rev., 110(6): 3315-3336 (2010).
Finney et al., "Chimeric receptors providing both primary and costimulatory signaling in T cells from a single gene product", Journal of Immunology, 161(6): 2791-2797 (1998).
Giege, R. et al., "Crystallogenesis of biological macromolecules: facts and perspectives", Acta Crystallogr D Biol Crystallogr, 50(Pt 4): 339-350 (1994).

Gross et al., "Therapeutic Potential of T Cell Chimeric Antigen Receptors (CARs) in Cancer Treatment: Counteracting Off-Tumor Toxicities for Safe CAR T Cell Therapy", Annu. Rev. Pharmacol. Toxicol., 56: 59-83 (2016).
Harlow and Lane, "Antibodies, A Laboratory Manual", Cold Spring Harbor Press (1988).
Henikoff et al., "Amino acid substitution matrices from protein blocks", Proc. Natl. Acad. Sci. U.S.A., 89(22): 10915-10919 (1992).
Kabat, EA. et al., "Attempts to locate complementarity-determining residues in the variable positions of light and heavy chains", Ann NY Acad Sci, 190: 382-391 (1971).
Kalos et al., "T cells with chimeric antigen receptors have potent antitumor effects and can establish memory in patients with advanced leukemia", Sci. Transl. Med., 3(95): 95ra73 (2011).
Kirkland, et al., "Analysis of the fine specificity and cross-reactivity of monoclonal anti-lipid A antibodies", J. Immunol. 137(11): 3614-3619 (1986).
Krause et al., "Antigen-dependent CD28 Signaling Selectively Enhances Survival and Proliferation in Genetically Modified Activated Human Primary T Lymphocytes", J. Exp. Med., 188(4): 619-626 (1998).
Mcpherson, A. "Crystallization of Proteins from Polyethylene Glycol", J Biol Chem, 251(20): 6300-6303 (1976).
Mcpherson, A. "Current approaches to macromolecular crystallization", Eur J Biochem, 189: 1-23 (1990).
Mendrola, et al. J Biol Chem, 277(7):4704-12, Epub (2002).
Moldenhauer, et al., "Identity of HML-1 antigen on intestinal intraepithelial T cells and of B-Iy7 antigen on hairy cell leukaemia", Scand. J. Immunol., 32(2): 77-82 (1990).
Morel et al., "Monoclonal antibodies to bovine serum albumin: affinity and specificity determinations", Molec. Immunol., 25(1): 7-15 (1988).
Porter et al., "Chimeric antigen receptor-modified T cells in chronic lymphoid leukemia", N. Engl. J. Med., 365(8): 725-33 (2011).
Roversi, P. et al., "Modelling prior distributions of atoms for macromolecular refinement and completion", Acta Crystallogr D Biol Crystallogr, 56(Pt 10): 1316-1323 (2000).
Sadelain, et al, "The Basic Principles of Chimeric Antigen Receptor Design", Cancer Discovery, 3: 388-398 (2013).
Song et al., "CD27 costimulation augments the survival and antitumor activity of redirected human T cells in vivo", Blood, 119(3): 696-706 (2012).
Stahli et al., "Distinction of epitopes by monoclonal antibodies", Methods in Enzymology, 92: 242-253 (1983).
Tramontano, A. et al., "Framework residue 71 is a major determinant of the position and conformation of the second hypervariable region in the VH domains of immunoglobulins" J Mol Biol, 215(1): 175-82 (1990).
Whitlow, et al., An Improved Linker for Single-Chain FV with Reduced Aggregation and Enhanced Proteolytic Stability, Protein Eng., 6(8):989-95 (1993).
Wu, et al., "Remote control of therapeutic T cells through a small molecule-gated chimeric receptor", Science, 350:6258 (2014).
Intl. Search Report-Written Opinion dated Feb. 12, 2019 for Intl. Appl. No. PCT/US2018/061331.
Evans, E.J. et al. (2005) "Crystal structure of a soluble CD28-Fab complex," Nature Immunology 6(3):271-279.
Pageon, S.V. et al. (2016) "Functional role of T-cell receptor nanoclusters in signal initiation and antigen discrimination," PNAS 113(37):E5454-E5463.
Van Der Merwe, P.A. et al. (2010) "Mechanisms for T cell receptor triggering," Nature Reviews Immunology 11(1):47-55.

* cited by examiner

| NAME | CRD1 | CRD2 | CRD3 |
|---|---|---|---|
| ANTI-BCMA HEAVY CHAIN | SYGMH | VISYDGSNKYYADSVKG | GPLQEPPYDYGMDV |
| ANTI-BCMA LIGHT CHAIN | RASQSVSSNLA | SASTRAT | QQHHVWPLT |

*FIG. 4A*

| NAME | CRD1 | CRD2 | CRD3 |
|---|---|---|---|
| ANTI-BCMA HEAVY CHAIN | GFTFSSY | SYDGSN | GPLQEPPYDYGMDV |
| ANTI-BCMA LIGHT CHAIN | RASQSVSSNLA | SASTRAT | QQHHVWPLT |

```
                                                                              1452 bp
          160         170         180         190
TATGGCATGCACTGGGTCCGTCAGGCTCCAGGCA
+++++++++++++++++++++++++++++++++++                                           190
 Y  G  M  H  W  V  R  Q  A  P  G

ACTGGCGTCAGGGGCCGTTGCAGGAGCCGCCATA
+++++++++++++++++++++++++++++++++++                                           380
             Y  C  V  K  G  P  L  Q  E  P  P  Y

AAGAGCCACCCTCCTGCAGGCCAGTCAGGAGT
+++++++++++++++++++++++++++++++++++                                           570
       R  A  T  L  S  C  R  A  S  Q  S

GAGAGATTTTGCAGTTATTACTGTCAGCAGCACC
+++++++++++++++++++++++++++++++++++                                           760
       E  D  F  A  V  Y  Y  C  Q  Q  H

CACTGATCATATTTGGTGTAATGGCTGGCGTCAT
+++++++++++++++++++++++++++++++++++                                           950
       [GLYCOPHORINA]
       T  L  I  F  G  V  M  A  G  V  I

GGTTGAGTTTTCAGATCGCAGATGCACCACCG
+++++++++++++++++++++++++++++++++++                                           1140
       V  K  F  S  R  S  A  D  A  P  A

GATAAGATGGCTGAAGCCTATTCTGAAATAGGCA
+++++++++++++++++++++++++++++++++++                                           1330
       D  K  M  A  E  A  Y  S  E  I  G

… # MODIFIED CHIMERIC ANTIGEN RECEPTORS AND METHODS OF USE

CROSS-REFERENCE TO RELATED APPLICATIONS

This application claims priority to U.S. Provisional Application No. 62/587,336, filed Nov. 16, 2017, which is incorporated by reference herein in its entirety.

FIELD OF THE INVENTION

The present disclosure relates generally to T cell therapies and more specifically to modified chimeric antigen receptors (CARs) that modulate T cell function.

SEQUENCE LISTING

The instant application contains a Sequence Listing which has been submitted electronically in ASCII format and is hereby incorporated by reference in its entirety. Said ASCII copy, created on Oct. 26, 2021, is named K1055US_ST25.txt and is 111,455 bytes in size.

BACKGROUND OF THE INVENTION

Human cancers by their nature comprise normal cells that have undergone a genetic or epigenetic conversion to become abnormal cancer cells. In doing so, cancer cells begin to express proteins and other antigens that are distinct from those expressed by normal cells. These aberrant tumor antigens may be used by the body's innate immune system to specifically target and kill cancer cells. However, cancer cells employ various mechanisms to prevent immune cells, such as T and B lymphocytes, from successfully targeting cancer cells.

Current therapies T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs), which comprise binding domains capable of interacting with a particular tumor antigen, allow T cells to target and kill cancer cells that express the particular tumor antigen.

A need exists for improved CARs for targeting and killing cancer cells.

SUMMARY OF THE INVENTION

As described in detail below, the present disclosure is based, in part, on the surprising discovery that introduction of residue or domain substitutions modulates CART cell function.

In one aspect, the present disclosure provides a polypeptide comprising a chimeric antigen receptor (CAR), wherein the CAR comprises an amino acid modification in the (i) hinge domain, (ii) transmembrane domain, and/or (iii) intracellular domain, wherein the amino acid modification modulates the activity of a CART cell.

In some embodiments, the hinge region is between the transmembrane domain and the antigen binding domain.

In some embodiments, the amino acid modification enhances oligomerization propensity of the CAR on the surface of a T cell relative to the CAR without the amino acid modification.

In some embodiments, the amino acid modification reduces oligomerization propensity of the CAR on the surface of a T cell relative to the CAR without the amino acid modification.

In some embodiments, the amino acid modification is present in an oligomerization interface of the CAR.

In some embodiments, the modification introduces or removes a salt bridge, a hydrophobic contact, an oligomerization domain, a leucine zipper, a disulfide bond, and/or a bulky side chain.

In some embodiments, the modification introduces a leucine zipper in the hinge/spacer domain. In some embodiments, the modification introduces a leucine zipper in the transmembrane domain. In some embodiments, the modification introduces a leucine zipper in the intracellular domain.

In some embodiments, the transmembrane domain comprises an inserted polypeptide from a protein known to be multimeric or monomeric. In some embodiments, the protein known to be multimeric comprises a GXXXG motif.

In some embodiments, the protein known to be multimeric comprises a receptor tyrosine kinase (RTK) selected from the group consisting of epidermal growth factor receptor (EGFR), erb-b2 receptor tyrosine kinase 2 (HER2), erb-b2 receptor tyrosine kinase 3 (HER3), erb-b2 receptor tyrosine kinase 4 (HER4), Insulin receptor (InsR), Insulin-like growth factor I receptor (IGF1R), Insulin receptor-related receptor (IRR), platelet derived growth factor receptor alpha (PDGFRα), platelet derived growth factor receptor beta (PDGFRβ), KIT proto-oncogene receptor tyrosine kinase (Kit), colony stimulating factor 1 receptor (CSFR), fms related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Axl), TYRO3 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A1 (EphA1), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphA10), EPH receptor B1 (EphB1), EPH receptor B2 (EphB2), EPH receptor B3 (EphB3), EPH receptor B4 (EphB4), EPH receptor B6 (EphB6), ret proto-oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmr1), lemur tyrosine kinase 2 (Lmr2), lemur tyrosine kinase 3 (Lmr3), leukocyte receptor tyrosine kinase (LTK), ALK receptor tyrosine kinase (ALK), serine/threonine/tyrosine kinase 1 (STYK1).

In some embodiments, the protein comprising a GXXXG motif is ErbB2 or glycophorin A (GpA).

In some embodiments, the hinge/spacer region comprises all or a fragment of IgG1, IgG2, IgG3, IgG4, IgA, IgD, IgE, IgM, CD28, or CD8 alpha. In some embodiments, the hinge/spacer region comprises all or a fragment of CD8 alpha. In some embodiments, the hinge/spacer region comprises all or a fragment of CD28.

In some embodiments, the hinge/spacer region comprises an amino acid substitution that modifies the glycosylation state of the polypeptide. In some embodiments, the hinge/spacer region comprises an amino acid substitution that modifies the glycosylation state of the polypeptide by removal of a putative N-linked glycosylation site. In some embodiments, the hinge/spacer region comprises an amino acid substitution that modifies the glycosylation state of the polypeptide by insertion of a putative N-linked glycosylation site. In some embodiments, the putative N-linked glycosylation site comprises the amino acid sequence NX[T/S], wherein X is not proline.

In some embodiments, the amino acid substitution comprises a substitution corresponding to N129Q and/or T131A substitutions in SEQ ID NO: 2.

In some embodiments, the hinge/spacer region and/or transmembrane region comprises an amino acid substitution or insertion that modifies the number of cysteine residues in the hinge/spacer region and/or transmembrane region. In some embodiments, a cysteine (C) residue is substituted with aspartic acid (D). In some embodiments, a cysteine (C) residue in the hinge/spacer domain is substituted with serine (S).

In some embodiments, a cysteine (C) residue in the transmembrane domain is substituted with alanine (A), valine (V), isoleucine (I), leucine (L), phenylalanine (F).

In some embodiments, the hinge/spacer and/or transmembrane domain comprises a substitution corresponding to C141S and/or C165A/V substitutions in SEQ ID NO:2.

In some embodiments, the transmembrane domain comprises a transmembrane domain of 4-1BB/CD137, an alpha chain of a T cell receptor, a beta chain of a T cell receptor, CD3 epsilon, CD4, CD5, CD8 alpha, CD8 beta, CD9, CD16, CD19, CD22, CD28, CD33, CD37, CD45, CD64, CD80, CD86, CD134, CD137, CD154, or a zeta chain of a T cell receptor, or any combination or fragment thereof.

In some embodiments, wherein the intracellular domain comprises a signaling region of 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CDIIa, CDIIb, CDIIc, CDIId, CDS, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulator (ICOS), integrins, ITGA4, ITGA4, ITGA6, ITGAD, ITGAE, ITGAL, ITGAM, ITGAX, ITGB2, ITGB7, ITGBI, KIRDS2, LAT, LFA-1, LFA-1, a ligand that specifically binds with CD83, LIGHT, LIGHT (tumor necrosis factor superfamily member 14; TNFSF14), LTBR, Ly9 (CD229), lymphocyte function-associated antigen-1 (LFA-1 (CDIIa/CD18), MHC class I molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Lyl08), SLAMF7, SLP-76, TNF receptor proteins, TNFR2, a Toll ligand receptor, TRANCE/RANKL, VLA1, or VLA-6, or a combination or fragment thereof.

In some embodiments, the intracellular domain comprises a 4-1BB/CD137 signaling region. In some embodiments, the polypeptide further comprises an antigen binding domain selected from the group consisting of scFv, Fab, Fab', Fv, F(ab')$_2$, dAb, and any combination thereof. In some embodiments, the antigen binding domain comprises an scFv. In some embodiments, the antigen binding domain comprises a heavy chain variable region (VH) and a light chain variable region (VL), wherein the VH comprises three complementarity determining regions (CDRs) and the VL comprises three CDRs.

In some embodiments, the antigen binding domain specifically binds an antigen selected from the group consisting of 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-IIRalpha, kappa chain, lambda chain, melanoma-associated antigen, mesothelin, MUC-1, mutated p53, mutated ras, prostate-specific antigen, ROR1, or VEGFR2, or a combination thereof.

In some embodiments, the antigen binding domain specifically binds BCMA.

In some embodiments, the polypeptide further comprises a leader peptide. In some embodiments, the polypeptide comprising a CAR is provided in Table C.

In one aspect, the present disclosure provides a polynucleotide encoding the polypeptide comprising a CAR described herein. In some embodiments, the polynucleotide encoding the polypeptide comprising a CAR is provided in Table C.

In one aspect, the present disclosure provides a vector comprising the polynucleotide encoding the polypeptide comprising a CAR described herein. In some embodiments, the vector is an adenoviral vector, an adenovirus-associated vector, a DNA vector, a lentiviral vector, a plasmid, a retroviral vector, or an RNA vector, or hybrid thereof.

In one aspect, the present disclosure provides a cell comprising the polypeptide, the polynucleotide, the vector, or any combination thereof. In some embodiments, the cell is a T cell.

In some embodiments, the T cell is an allogeneic T cell, an autologous T cell, an engineered autologous T cell (eACT), or a tumor-infiltrating lymphocyte (TIL). In some embodiments, the T cell is a CD4+ T cell. In some embodiments, the T cell is a CD8+ T cell. In some embodiments, the T cell is an in vitro cell. In some embodiments, the T cell is an autologous T cell.

In one aspect, the present disclosure provides a composition comprising (a) the polypeptide, the polynucleotide, the vector, the cells, or any combination thereof comprising the modified CAR described herein; and (b) a pharmaceutically-acceptable carrier or excipient. In some embodiments, the composition is formulated to be delivered to a subject. In some embodiments, the subject is a human.

In one aspect, the present disclosure provides a method of making a cell expressing a polypeptide described herein, comprising transducing a cell with a polynucleotide encoding the polypeptide suitable conditions. In some embodiments, the method further comprises isolating the transduced cell. In some embodiments, the method further comprises measuring a functional property of the transduced cell. In some embodiments, the functional property is proliferation, activation or cytokine release.

Any aspect or embodiment described herein may be combined with any other aspect or embodiment as disclosed herein. While the present invention has been described in conjunction with the detailed description thereof, the foregoing description is intended to illustrate and not limit the scope of the present invention, which is defined by the scope of the appended claims. Other aspects, advantages, and modifications are within the scope of the following claims.

Other features and advantages of the invention will be apparent from the Drawings and the following Detailed Description, including the Examples, and the claims.

BRIEF DESCRIPTION OF THE DRAWINGS

The above and further features will be more clearly appreciated from the following detailed description when taken in conjunction with the accompanying drawings. The drawings however are for illustration purposes only and not for limitation.

FIGS. 4A and 4B show the complementary determining region of exemplary anti-BCMA antigen binding molecules provided herein according to Kabat, and Clothia naming conventions, respectively. In each row from the top to the bottom, the CDR1, CDR2 and CDR3 sequences as shown have SEQ ID NOs of SEQ ID NO:55, 56, and 57 (anti-BCMA heavy chain), 58, 59, and 60 (anti-BCMA light chain), 61, 62, and 63 (anti-BCMA heavy chain), and 64, 65 and 66 (anti-BCMA light chain).

FIG. 5 shows a sequence map of an anti-BCMA CAR comprising disulfide bond mutations C292S and C316V (corresponding to C141S and C165V of CD28) (SEQ ID Nos: 41 and 42). The horizontal bars delineate CAR domains (e.g., leader peptide, heavy chain variable region, linker, light chain variable region, spacer, extracellular domain, transmembrane domain, and intracellular domain.

FIG. 6 shows a sequence map of an anti-BCMA CAR with a modified number of cysteines by introduction of a putative N-linked glycosylation site C292N and P293G (corresponding to C141N and P142G of CD28) (SEQ ID Nos: 43 and 44). The horizontal bars delineate CAR domains (e.g., leader peptide, heavy chain variable region, linker, light chain variable region, spacer, extracellular domain, transmembrane domain, and intracellular domain.

FIG. 7 shows a sequence map of an anti-BCMA CAR comprising disulfide bond mutation C292S (corresponding to C141S of CD28) and glycophorin A transmembrane domain substitution (SEQ ID Nos: 45 and 46). The horizontal bars delineate CAR domains (e.g., leader peptide, heavy chain variable region, linker, light chain variable region, spacer, extracellular domain, transmembrane domain, and intracellular domain.

FIG. 8 shows a sequence map of an anti-BCMA CAR comprising disulfide bond mutation C292S (corresponding to C141S of CD28) and glycophorin A monomeric transmembrane domain substitution G83I (SEQ ID Nos: 47 and 48). The horizontal bars delineate CAR domains (e.g., leader peptide, heavy chain variable region, linker, light chain variable region, spacer, extracellular domain, transmembrane domain, and intracellular domain.

FIG. 9 shows a sequence map of an anti-BCMA CAR comprising disulfide bond mutation C292S (corresponding to C141S of CD28) and ErbB2 transmembrane domain substitution (SEQ ID Nos: 49 and 50). The horizontal bars delineate CAR domains (e.g., leader peptide, heavy chain variable region, linker, light chain variable region, spacer, extracellular domain, transmembrane domain, and intracellular domain.

FIG. 10 shows a sequence map of an anti-BCMA CAR comprising disulfide bond mutation C292S (corresponding to C141S of CD28) and ErbB2 monomeric transmembrane domain substitution G83I (SEQ ID Nos: 51 and 52). The horizontal bars delineate CAR domains (e.g., leader peptide, heavy chain variable region, linker, light chain variable region, spacer, extracellular domain, transmembrane domain, and intracellular domain.

DETAILED DESCRIPTION OF THE INVENTION

Figure 1:
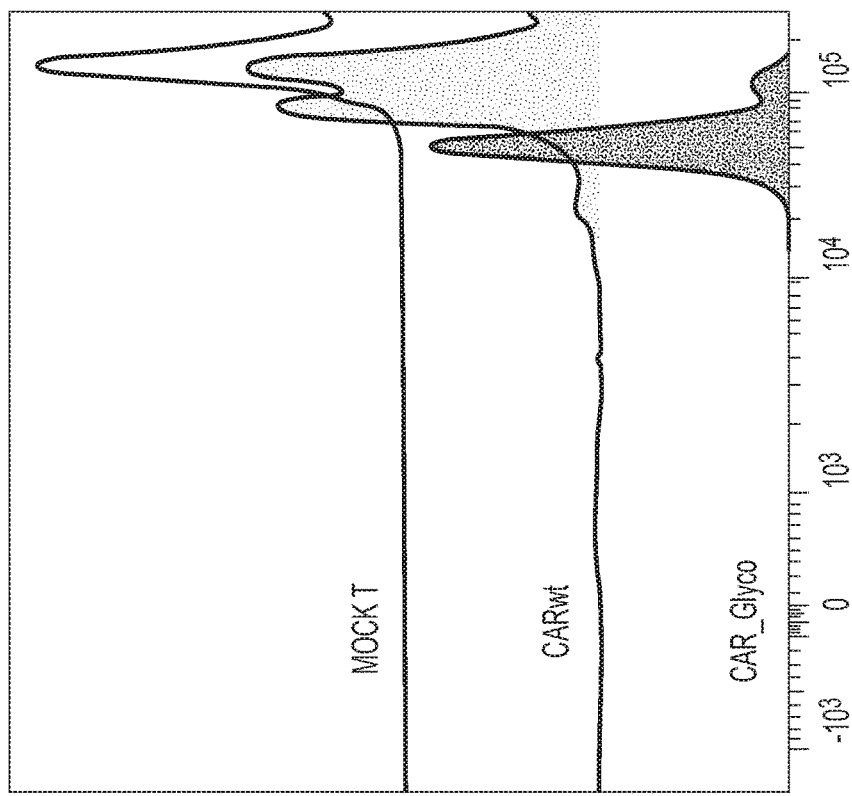
FIG. 1 shows proliferation of T cells expressing an anti-BCMA CAR with a CD28 hinge/spacer with an N-linked glycosylation site (CARwt) or with the N-linked glycosylation site removed (CARaGlyco) after 72 hours of co-culture with BCMA positive MM1S cells (left) or BCMA negative Eol-1 cells (right), as measured by flow cytometric analysis of carboxyfluorescein succinimidyl ester (CFSE) dilution. Mock transduced T cells (Mock T) are shown as a control.
Figure 1:
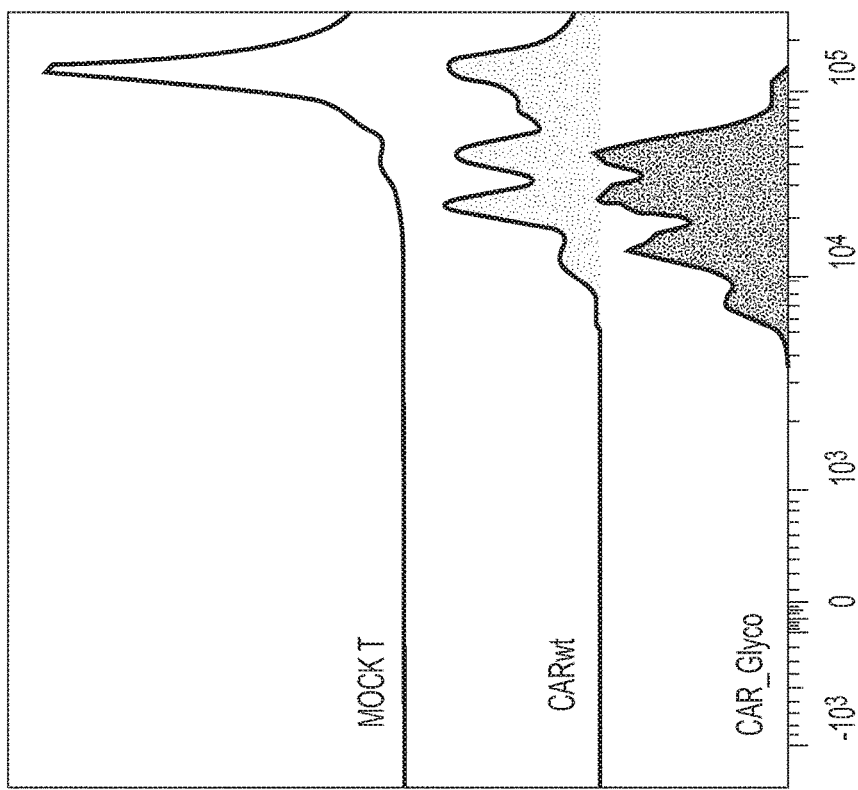

The present disclosure relates to novel chimeric antigen receptor (CAR) polypeptides comprising modified hinge/spacer, transmembrane and/or intracellular domains and polynucleotides encoding the same. The present disclosure also provides vectors (e.g., viral vectors) comprising such polynucleotides and compositions comprising such vectors. The present disclosure further provides polynucleotides encoding such CARs and compositions comprising such polynucleotides. The present disclosure additionally provides engineered cells (e.g., T cells) comprising such polynucleotides and/or transduced with such viral vectors and compositions comprising such engineered cells. The present disclosure provides compositions (e.g., pharmaceutical compositions) including a plurality of engineered T cells. The present disclosure provides methods for manufacturing such engineered T cells and compositions and uses (e.g., in treating a melanoma) of such engineered T cells and compositions. And, the present disclosure provides a method of inducing immunity against a tumor comprising administering to a subject an effective amount of a cell comprising the polynucleotide, the vector, or the polypeptide of the present disclosure. Other aspects of the disclosure relate to cells comprising the CAR and their use in a T cell therapy, e.g., an autologous cell therapy (eACT™), for the treatment of a patient suffering from a cancer.

A CAR may comprise, for example, an antigen-specific component ("antigen binding molecule"), (ii) one or more costimulatory domains (which includes a hinge/spacer domain), and (iii) one or more activating domains. Each domain may be heterogeneous, that is, comprised of sequences derived from different protein chains. CAR-expressing immune cells (such as T cells) may be used in various therapies, including cancer therapies.

The ability of a CAR construct to self-associate in the absence of an activation signal may have profound effects on the CAR activation threshold and, ultimately, the persistence of a CAR-T cell. The present disclosure describes the design of assorted hinge/spacer and transmembrane domain modifications intended to modulate the oligomeric state of CAR constructs to create tools to modulate the function of CAR T-cells. The presently described modifications in the hinge/spacer and transmembrane region of the CAR may affect the magnitude of CAR T-mediated immune response, especially in situations with extreme levels of target expression.

Next generation CART cells have been designed to modulate functionality based on the ability of the CAR molecule to associate on the cell surface affects function. Amino acid modifications described herein may affect (1) the glycosylation state of a protein by removal of an N-linked glycosylation site; (2) the presence of cysteine residues; (3) oligomerization propensity of the CAR on the surface of a T cell relative to the CAR without the amino acid modification.

As described in more detail below, including the Examples section, CARs comprising a modified extracellular, hinge/spacer, transmembrane and/or intracellular domain provide unexpectedly superior properties when compared to a CAR without the modifications described herein. Polynucleotides encoding such CARs may be transduced into T cells and the CARs are expressed in T cells, e.g., a patient's own T cells. When the transduced T cells are transplanted back to a patient, the CARs direct the T cells to recognize and bind an epitope present on the surface of cancer cells, thus, allowing binding of cancer cells rather than non-cancerous cells. This binding leads to activation of cytolytic mechanisms in the T cell that specifically kill the bound cancer cells. Prior to the present invention, it was unknown that modifications to the extracellular, hinge, or transmembrane regions of the CAR would modulate activity and/or proliferation of the T cell. Thus, the present invention satisfies an unmet need that exists for novel and improved therapies for treating cancer.

Examples of CART cell therapies and constructs are described in U.S. Patent Publication Nos. 2013/0287748, 2014/0227237, 2014/0099309, and 2014/0050708; International Patent Publications Nos. WO2012033885, WO2012079000, WO2014127261, WO2014186469, WO2015080981, WO2015142675, WO2016044745, and WO2016090369; and Sadelain et al, Cancer Discovery, 3: 388-398 (2013), each of which is incorporated by reference in its entirety.

Definitions

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" may mean within one or more than one standard deviation per the practice in the art. "About" or "comprising essentially of" may mean a range of up to 10% (i.e., ±10%). Thus, "about" may be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg may include any amount between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", 2nd ed., (2001), CRC Press; "The Dictionary of Cell & Molecular Biology", 5th ed., (2013), Academic Press; and "The Oxford Dictionary Of Biochemistry And Molecular Biology", Cammack et al. eds., 2nd ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering may also be performed, for example, once, a plurality of times, and/or over one or more extended periods.

The term "antibody" (Ab) includes, without limitation, a glycoprotein immunoglobulin which binds specifically to an antigen. In general, and antibody may comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies may include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In some embodiments, antibodies described herein refer to polyclonal antibody populations.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule may include the antigenic complementarity determining regions (CDRs). Examples of antibody fragments include, but are not limited to, Fab, Fab', F(ab')$_2$, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In some embodiments, the antigen binding molecule binds to BCMA. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

As used herein, the term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In some embodiments, the variable region is a human variable region. In some embodiments, the variable region comprises rodent or murine CDRs and human framework regions (FRs). In particular embodiments, the variable region is a primate (e.g., non-human primate) variable region. In some embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

CDR Numbering

| Loop | Kabat | AbM | Chothia | Contact |
|------|-------|-----|---------|---------|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody may be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally may include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody may be determined according to the Chothia numbering scheme, which refers to the location of immunoglobulin structural loops (see, e.g., Chothia C & Lesk A M, (1987), J Mol Biol 196: 901-917; A1-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which may exhibit various effector functions, such as interaction with the Fc receptor. The constant region of an immunoglobulin molecule generally has a more conserved amino acid sequence relative to an immunoglobulin variable domain.

As used herein, the terms "region" and "domain" are interchangeable and have a meaning common in the art.

As used herein, the term "heavy chain" when used in reference to an antibody may refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody may refer to any distinct type, e.g., kappa (κ) or lambda (λ) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the dissociation constant (KD or Kd). Affinity may be measured and/or expressed in a number of ways known in the art, including, but not limited to, equilibrium dissociation constant (KD), and equilibrium association constant (KA or Ka). The KD is calculated from the quotient of koff/kon, whereas KA is calculated from the quotient of kon/koff. kon refers to the association rate constant of, e.g., an antibody to an antigen, and koff refers to the dissociation of, e.g., an antibody to an antigen. The kon and koff may be determined by techniques known to one of ordinary skill in the art, such as BIACORE® or KinExA® instrument.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some embodiments, one or more amino acid residues within a CDR(s) or within a framework region(s) of an antibody or antigen-binding molecule thereof may be replaced with an amino acid residue with a similar side chain.

As, used herein, the term "heterologous" means from any source other than naturally occurring sequences. For example, a heterologous sequence included as a part of the costimulatory protein having the amino acid sequence of SEQ ID NO: 2, e.g., the corresponding human costimulatory protein, is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

As used herein, an "epitope" is a term in the art and refers to a localized region of an antigen to which an antibody may specifically bind. An epitope may be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In some embodiments, the epitope to which an antibody binds may be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition may be complete, e.g., binding of the binding molecule to the antigen completely blocks the ability of the reference binding molecule to bind the antigen, or it may be partial, e.g., binding of the binding molecule to the antigen reduces the ability of the reference binding molecule to bind the antigen. In some embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays may be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE® instrument, KinExA® 3000 instrument (Sapidyne Instruments, Boise, Id.), or other assays known in the art. In a specific embodiment, molecules that specifically bind to an antigen bind to the antigen with a KA that is at least 2 logs, 2.5 logs, 3 logs, 4 logs or greater than the KA when the molecules bind to another antigen.

In another embodiment, molecules that specifically bind to an antigen bind with a dissociation constant (Kd) of about $1\times10^{-7}$ M. In some embodiments, the antigen binding molecule specifically binds an antigen with "high affinity" when the Kd is about $1\times10^{-9}$ M to about $5\times10^{-9}$ M. In some embodiments, the antigen binding molecule specifically binds an antigen with "very high affinity" when the Kd is $1\times10^{-10}$ M to about $5\times10^{-10}$ M. In some embodiments, the antigen binding molecule has a Kd of $10^{-9}$ M. In some embodiments, the off-rate is less than about $1\times10^{-9}$. In other embodiments, the antigen binding molecule binds human BCMA with a Kd of between about $1\times10^{-7}$ M and about $1\times10^{-13}$ M. In yet another embodiment, the antigen binding molecule binds human BCMA with a Kd of about $1\times10^{-10}$ M to about $5\times10^{-10}$ M.

In a specific embodiment, provided herein is an antibody or an antigen binding molecule thereof that binds to a target human antigen, e.g., human BCMA or human CLL-1, with higher affinity than to another species of the target antigen, e.g., a non-human BCMA or a non-human CLL-1. In some embodiments, provided herein is an antibody or an antigen binding molecule t thereof that binds to the target human antigen, e.g., human BCMA or human CLL-1, with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, may serve as an antigen. An antigen may be endogenously expressed, i.e. expressed by genomic DNA, or may be recombinantly expressed. An antigen may be specific to a certain tissue, such as a cancer cell, or it may be broadly expressed. In addition, fragments of larger molecules may act as antigens. In some embodiments, antigens are tumor antigens. In some embodiments, the antigen is BCMA.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "BCMA" refers to B cell maturation antigen, which may include, but is not limited to, native BCMA, an isoform of BCMA, or an interspecies BCMA homolog of BCMA. BCMA (also known as TNFRSF17, CD269, and TNFRSF13A) is a member of the tumor necrosis factor (TNF)-receptor superfamily. BCMA is expressed on the surface of multiple myeloma cells, while highly restricted to plasma cells and a subset of mature B cells in healthy tissue. The amino acid sequence of human BCMA (hBCMA) is provided in NCBI Accession Q02223.2 (GI:313104029). As used herein, BCMA includes human BCMA and non-human BCMA homologs, as well as variants, fragments, or post-transnationally modified forms thereof, including, but not limited to, N- and O-linked glycosylated forms of BCMA. BCMA proteins may further include fragments comprising all or a portion of the extracellular domain of BCMA (e.g., all or a portion of amino acids 1-54 of hBCMA).

As used herein, the term "CLL-1" refers to C-type lectin-like molecule-1, which may include, but is not limited to native CLL-1, an isoform of CLL-1, or an interspecies CLL-1 homolog of CLL-1. CLL-1 (also known as C-type lectin domain family 12 member A, CLEC12A, dendritic cell-associated lectin 2, DCAL-2, myeloid inhibitory C-type lectin-like receptor, and MICL) is a cell surface receptor that modulates signaling cascades and mediates tyrosine phosphorylation of target MAP kinases. CLL-1 expression is observed, e.g., in acute myeloid leukemia (AML) cells. The amino acid sequence of human CLL-1 (hCLL-1) is provided in UniProtKB/Swiss-Prot Accession No. Q5QGZ9.3 (GI: 308153619). As used herein, CLL-1 includes human CLL-1 and non-human CLL-1 homologs, as well as variants, fragments, or post-transnationally modified forms thereof, including, but not limited to, N- and O-linked glycosylated forms of CLL-1.

As used herein, the term "FLT3" refers to Fms-like tyrosine kinase 3 (FLT-3), which may include, but is not limited to native FLT3, an isoform of FLT3, or an interspecies FLT3 homolog of FLT3. FLT3 (also known as Cluster of differentiation antigen 135 (CD135), receptor-type tyrosine-protein kinase FLT3, FMS-related tyrosine kinase 3, stem cell tyrosine kinase 1, FL cytokine receptor, growth factor receptor tyrosine kinase type III, STK1, or fetal liver kinase-2 (Flk2)) is a cytokine receptor which belongs to the receptor tyrosine kinase class III. CD135 is the receptor for the cytokine Flt3 ligand (FLT3L). FLT3 is expressed on the surface of various hematopoietic progenitor cells and on the surface of acute myeloid leukemia (AML) cells. The amino acid sequence of human FLT3 (hFLT3) is provided in UniProtKB/Swiss-Prot Accession No. P36888 (GI: 156630887). As used herein, FLT3 includes human FLT3 and non-human FLT3 homologs, as well as variants, fragments, or post-transnationally modified forms thereof, including, but not limited to, N- and O-linked glycosylated forms of FLT3.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" may include a tumor. Examples of cancers that may be treated by the methods disclosed herein include, but are not limited to, cancers of the immune system including lymphoma, leukemia, myeloma, and other leukocyte malignancies. In some embodiments, the methods disclosed herein may be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T cell lymphoma, environmentally induced cancers including those induced by asbestos, other B cell malignancies, and combinations of said cancers. In some embodiments, the cancer is multiple myeloma. The particular cancer may be responsive to chemo- or radiation therapy or the cancer may be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that may present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect may also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. "Cytokine" as used herein is meant to refer to proteins released by one cell population that act on another cell as intercellular mediators. A cytokine may be endogenously expressed by a cell or administered to a subject. Cytokines may be released by immune cells, including macrophages, B cells, T cells, and mast cells to propagate an immune response. Cytokines may induce various responses in the recipient cell. Cytokines may include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines may promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CART cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T cells play a major role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory TSCM cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory TCM cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which may either be obtained from a patient or a donor. The cell may be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy may include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which may be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells may be engineered to express, for example, chimeric antigen receptors (CAR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain may be derived from a naturally-occurring costimulatory domain, e.g., having the amino acid sequence of SEQ ID NO: 2, or a variant thereof, e.g., a variant having a SEQ ID NO: 27, and the activating domain may be derived from, e.g., CD3-zeta. In some embodiments, the CAR is designed to have two, three, four, or more costimulatory domains. The CAR scFv may be designed to target, for example, CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CART cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell may include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that may comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) may specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody, an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand," as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand may include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CDI-Ia, CDI-Ib, CDI-Ic, CDI-Id, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGBI, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CDI Ia/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Lyl08), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In some embodiments, "treatment" or "treating" includes a partial remission. In another embodiment, "treatment" or "treating" includes a complete remission.

To calculate percent identity, the sequences being compared are typically aligned in a way that gives the largest match between the sequences. One example of a computer program that may be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In some embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Various aspects of the invention are described in further detail in the following subsections.

I. Chimeric Antigen Receptors

Chimeric antigen receptors (CARs or CAR-Ts) are genetically engineered receptors. These engineered receptors may be readily inserted into and expressed by immune cells, including T cells in accordance with techniques known in the art. With a CAR, a single receptor may be programmed to both recognize a specific antigen and, when bound to that antigen, activate the immune cell to attack and destroy the cell bearing that antigen. When these antigens exist on tumor cells, an immune cell that expresses the CAR may target and kill the tumor cell.

One aspect of the present invention is directed to polypeptides comprising chimeric antigen receptors (CARs) comprising an amino acid modification that modulates the activity of a CAR T cell and engineered T cells comprising the same. The CAR may further comprise a hinge/spacer or extracellular domain, a transmembrane domain and/or an intracellular domain. In some embodiments, a CAR encoded by the polynucleotide disclosed hereinfurther comprises an antigen binding molecule or domain that specifically binds to a target antigen. In some embodiments, the CAR encoded by the polynucleotide further comprises an activating domain. In some embodiments, the CAR encoded by the polynucleotide comprises (i) an antigen binding molecule that specifically binds to a target antigen, (ii) a hinge domain, a transmembrane domain, and an intracellular domain, and (iii) an activating domain, wherein the hinge domain and/or transmembrane domain comprises, an amino acid modification described herein (e.g., relative to a CAR without the modification).

In some embodiments, an orientation of the CARs in accordance with the disclosure comprises an antigen binding domain (such as scFv) in tandem with a costimulatory domain and an activating domain. The costimulatory domain may comprise one or more of an extracellular portion, a transmembrane portion, and an intracellular portion. In other embodiments, multiple costimulatory domains may be utilized in tandem.

Costimulatory Domain

Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). The costimulatory protein having the amino acid sequence of SEQ ID NO: 2 is a costimulatory protein found naturally on T cells. The complete native amino acid sequence of this costimulatory protein is described in NCBI Reference Sequence: NP_006130.1. The complete native nucleic acid sequence of this costimulatory protein is described in NCBI Reference Sequence: NM_006139.1.

Extracellular or "Hinge" Domain

In some embodiments, a CAR of the instant disclosure comprises an "extracellular" or "hinge" or "spacer" domain or region, which terms are used interchangeably herein. The present disclosure demonstrates that modifications to the hinge/spacer domain may improve one or more properties of a CAR. In some embodiments, the hinge/spacer domain may comprise a truncated hinge/spacer domain (THD) the THD domain is a truncated version of a complete hinge/spacer domain ("CHD"). In some embodiments, an extracellular domain is from or derived from (e.g., comprises all or a fragment of) ErbB2, glycophorin A (GpA), CD2, CD3 delta, CD3 epsilon, CD3 gamma, CD4, CD7, CD8a, CD813, CD11a (ITGAL), CD11b (ITGAM), CD11c (ITGAX), CD11d (ITGAD), CD18 (ITGB2), CD19 (B4), CD27 (TN-FRSF7), CD28, CD28T, CD29 (ITGB1), CD30 (TN-FRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll ligand receptor, and fragments or combinations thereof. An "extracellular" or "hinge" or "spacer" domain or region may be derived either from a natural or from a synthetic source.

In some embodiments, an "extracellular" or "hinge" or "spacer" domain or region is positioned between an antigen binding molecule (e.g., an scFv) and a transmembrane domain. In this orientation, the hinge/spacer domain provides distance between the antigen binding molecule and the surface of a cell membrane on which the CAR is expressed. In some embodiments, an "extracellular" or "hinge" or "spacer" domain or region is from or derived from an immunoglobulin. In some embodiments, an "extracellular" or "hinge" or "spacer" domain or region is selected from the hinge/spacer regions of IgG1, IgG2, IgG3, IgG4, IgA, IgD, IgE, and IgM, or a fragment thereof. In some embodiments, an "extracellular" or "hinge" or "spacer" domain or region comprises, is from, or is derived from the hinge/spacer region of CD8 alpha. In some embodiments, an "extracellular" or "hinge" or "spacer" domain or region comprises, is from, or is derived from the hinge/spacer region of CD28. In some embodiments, an "extracellular" or "hinge" or "spacer" domain or region comprises a fragment of the hinge/spacer region of CD8 alpha or a fragment of the hinge/spacer region of CD28, wherein the fragment is anything less than the whole hinge/spacer region. In some embodiments, the fragment of the CD8 alpha hinge/spacer region or the fragment of the CD28 hinge/spacer region comprises an amino acid sequence that excludes at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 amino acids at the N-terminus or C-Terminus, or both, of the CD8 alpha hinge/spacer region, or of the CD28 hinge/spacer region.

In some embodiments, an "extracellular" or "hinge" or "spacer" domain or region comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence SEQ ID NO: 2 or a fragment thereof. In some embodiments, an "extracellular" or "hinge" or "spacer" domain or region comprises the amino acid sequence of SEQ ID NO: 2 or a fragment thereof.

In some embodiments, an "extracellular" or "hinge" or "spacer" domain or region comprises an amino acid substitution that modifies the glycosylation state of the polypeptide. In some embodiments, the hinge/spacer region comprises an amino acid substitution that modifies the glycosylation state of the polypeptide by removal of an N-linked glycosylation site. In some embodiments, the amino acid substation comprises N129Q and/or T131A substitutions in SEQ ID NO: 2. In some embodiments, the hinge/spacer region comprises an amino acid substitution or insertion that modifies the number of cysteine residues in the hinge/spacer region and/or transmembrane region. In some embodiments, a cysteine (C) residue is substituted with aspartic acid (D) or a serine (S) or another residue. In some embodiments, a cysteine (C) residue is substituted with an aasparagine (N) followed by a residue that is not proline (P), followed by a seriene (S) or threonine (T), thereby introducing a putative N-liked glycosylation site. In some embodiments, the hinge/spacer domain comprises C141S substitutions in SEQ ID NO: 2.

In some embodiments, the CD28 domain is derived from a human CD28 hinge/spacer region, and may comprise SEQ ID NO: 2. In other embodiments, the CD28 domain is derived from a rodent, murine, or primate (e.g., non-human primate) CD28 hinge/spacer region. In some embodiments, the CD28 domain is derived from a chimeric CD28 hinge/spacer region.

In some embodiments, an "extracellular" or "hinge" or "spacer" domain or region comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence of the CD8 extracellular domain and transmembrane domain set forth in AAALSNSIMYFSHFVPVFL-PAKPTTTPAPRPPTPAPTIASQPLSLRPEACR-PAAGGAVHTRGLDFACDIYIWAPLAGTCG VLLLSLVITLYCNHRN (SEQ ID NO: 54) or a fragment thereof. In some embodiments, an "extracellular" or "hinge" or "spacer" domain or region comprises the amino acid sequence of SEQ ID NO: 54 or a fragment thereof.

In some embodiments, an "extracellular" or "hinge" or "spacer" domain or region comprises an amino acid substitution that modifies the glycosylation state of the polypeptide. In some embodiments, the hinge/spacer region comprises an amino acid substitution that modifies the glycosylation state of the polypeptide by removal of an N-linked glycosylation site. In some embodiments, the hinge/spacer region comprises an amino acid substitution or insertion that modifies the number of cysteine residues in the hinge/spacer region and/or transmembrane region. In some embodiments, a cysteine (C) residue is substituted with aspartic acid (D) or a serine (S) or another residue. In some embodiments, a cysteine (C) residue is substituted with an aasparagine (N) followed by a residue that is not proline (P), followed by a seriene (S) or threonine (T), thereby introducing a putative N-liked glycosylation site.

In some embodiments, the CD8 domain is derived from a human CD8 hinge/spacer region, and may comprise SEQ ID NO: 54 or a fragment thereof. In other embodiments, the CD8 domain is derived from a rodent, murine, or primate (e.g., non-human primate) CD8 hinge/spacer region. In some embodiments, the CD8 domain is derived from a chimeric CD8 hinge/spacer region.

In some embodiments, an extracellular domain comprises some or all of a member of the immunoglobulin family such as IgG1, IgG2, IgG3, IgG4, IgA, IgD, IgE, IgM, or a fragment thereof.

In some embodiments, a short peptide or polypeptide linker, preferably between 2 and 10 amino acids in length may form the linkage between the hinge/spacer domain and the antigen binding domain, or between the hinge/spacer domain and a transmembrane domain of a CAR. In some embodiments, a short oligo- or polypeptide linker, preferably between 2 and 10 amino acids in length may form the linkage. A glycine-serine doublet (GS), glycine-serine-glycine triplet (GSG), Gly-Gly-Gly-Gly-Ser (G4S)z where z is 1, 2, 3, 4, 5, 6 or 7, or an alanine-alanine-alanine (AAA) triplet provides a particularly suitable linker.

Transmembrane Domain

The CAR of the present disclosure may further comprise a transmembrane domain and/or an intracellular signaling domain. The transmembrane domain may be designed to be fused to the extracellular domain of the CAR. It may similarly be fused to the intracellular domain of the CAR. In some embodiments, the transmembrane domain that naturally is associated with one of the domains in a CAR is used. In some instances, the transmembrane domain may be selected or modified (e.g., by an amino acid substitution) to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein.

In some embodiments, the transmembrane domain may be modified by the introduction of a salt bridge, a hydrophobic contact, and/or a multimerization domain, including a leucine zipper. In some embodiments, the transmembrane domain may be modified with repulsive elements which may include bulky side chains and like charges (e.g., by introducing a substitution like C141D). In some embodiments, the transmembrane region may be substituted with segments from proteins known to self associate or stay monomeric. In some embodiments, the amino acid modification enhances oligomerization propensity of the CAR on the surface of a T cell relative to the CAR without the amino acid modification. In some embodiments, the amino acid modification reduces oligomerization propensity of the CAR on the surface of a T cell relative to the CAR without the amino acid modification. In some embodiments, the amino acid modification is present in an oligomerization interface of the CAR.

Transmembrane regions may be derived from (i.e., comprise) a receptor tyrosine kinase (e.g., ErbB2), glycophorin A (GpA), 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CDI Ia, CDI Ib, CDI Ic, CDI Id, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGBI, KIRDS2, LAT, LFA-1, LFA-1, a ligand that specifically binds with CD83, LIGHT, LIGHT, LTBR, Ly9 (CD229), lymphocyte function-associated antigen-1 (LFA-1; CDI-Ia/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Lyl08), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, a receptor tyrosine kinase may be derived from (e.g., comprise) Insulin receptor (InsR), Insulin-like growth factor I receptor (IGF1R), Insulin receptor-related receptor (IRR), platelet derived growth factor receptor alpha (PDGFRα), platelet derived growth factor receptor beta (PDGFRβ), KIT proto-oncogene receptor tyrosine kinase (Kit), colony stimulating factor 1 receptor (CSFR), fms related tyrosine kinase 3 (FLT3), fms related tyrosine kinase 1 (VEGFR-1), kinase insert domain receptor (VEGFR-2), fms related tyrosine kinase 4 (VEGFR-3), fibroblast growth factor receptor 1 (FGFR1), fibroblast growth factor receptor 2 (FGFR2), fibroblast growth factor receptor 3 (FGFR3), fibroblast growth factor receptor 4 (FGFR4), protein tyrosine kinase 7 (CCK4), neurotrophic receptor tyrosine kinase 1 (trkA), neurotrophic receptor tyrosine kinase 2 (trkB), neurotrophic receptor tyrosine kinase 3 (trkC), receptor tyrosine kinase like orphan receptor 1 (ROR1), receptor tyrosine kinase like orphan receptor 2 (ROR2), muscle associated receptor tyrosine kinase (MuSK), MET proto-oncogene, receptor tyrosine kinase (MET), macrophage stimulating 1 receptor (Ron), AXL receptor tyrosine kinase (Axl), TYRO3 protein tyrosine kinase (Tyro3), MER proto-oncogene, tyrosine kinase (Mer), tyrosine kinase with immunoglobulin like and EGF like domains 1 (TIE1), TEK receptor tyrosine kinase (TIE2), EPH receptor A1 (EphA1), EPH receptor A2 (EphA2), (EPH receptor A3) EphA3, EPH receptor A4 (EphA4), EPH receptor A5 (EphA5), EPH receptor A6 (EphA6), EPH receptor A7 (EphA7), EPH receptor A8 (EphA8), EPH receptor A10 (EphA10), EPH receptor B1 (EphB1), EPH receptor B2 (EphB2), EPH receptor B3 (EphB3), EPH receptor B4 (EphB4), EPH receptor B6 (EphB6), ret proto-oncogene (Ret), receptor-like tyrosine kinase (RYK), discoidin domain receptor tyrosine kinase 1 (DDR1), discoidin domain receptor tyrosine kinase 2 (DDR2), c-ros oncogene 1, receptor tyrosine kinase (ROS), apoptosis associated tyrosine kinase (Lmr1), lemur tyrosine kinase 2 (Lmr2), lemur tyrosine kinase 3 (Lmr3), leukocyte receptor tyrosine kinase (LTK), ALK receptor tyrosine kinase (ALK), or serine/threonine/tyrosine kinase 1 (STYK1).

In some embodiments, short linkers may form linkages between any or some of the extracellular, transmembrane, and intracellular domains of the CAR. In some embodiments, the amino acid sequence of the costimulatory protein's transmembrane domain is set forth in SEQ ID NO: 2. In some embodiments, the transmembrane region comprises an amino acid substitution that modifies the glycosylation state of the polypeptide by removal of an N-linked glycosylation site. In some embodiments, the transmembrane region comprises an amino acid substitution or insertion that modifies the number of cysteine residues in the hinge/spacer region and/or transmembrane region. In some embodiments, a cysteine (C) residue is substituted with aspartic acid (D) or a serine (S). In some embodiments, a cysteine (C) residue in the transmembrane domain is substituted with alanine (A), valine (V), isoleucine (I), leucine (L), phenylalanine (F).

In some embodiments, wherein the hinge/spacer and/or transmembrane domain comprises C141S and/or C165A substitutions in SEQ ID NO: 2.

In some embodiments, the transmembrane domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of 2.

In some embodiments, the transmembrane domain is derived from (e.g., comprises) CD8. In some embodiments, the transmembrane domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of the CD8 transmembrane domain.

Intracellular (Signaling) Domain:

The intracellular (signaling) domain of the engineered T cells disclosed hereinmay provide signaling to an activating domain, which then activates at least one of the normal effector functions of the immune cell. Effector function of a T cell, for example, may be cytolytic activity or helper activity including the secretion of cytokines.

In some embodiments, suitable intracellular signaling domain include (e.g., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CDI Ia, CDI Ib, CDI Ic, CDI Id, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGBI, KIRDS2, LAT, LFA-1, LFA-1, ligand that specifically binds with CD83, LIGHT, LIGHT, LTBR, Ly9 (CD229), Lyl08), lymphocyte function-associated antigen-1 (LFA-1; CDI-Ia/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Activating Domain

CD3 is an element of the T cell receptor on native T cells, and has been shown to be an important intracellular activating element in CARs. In some embodiments, the CD3 is CD3 zeta.

In some embodiments, the activating domain comprises an amino acid sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 27.

The amino acid of intracellular CD3 zeta is set forth in SEQ ID NO: 27:

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

Antigen Binding Molecules

CARs may be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment ("scFv"). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they may be engineered to be expressed as part of a single chain along with the other CAR components. Id. See also Krause et al., J. Exp. Med., Volume 188, No. 4, 1998 (619-626); Finney et al., Journal of Immunology, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

In some embodiments, the polynucleotide encodes a CAR comprising a modified hinge/spacer domain disclosed herein and an antigen binding molecule that specifically binds to a target antigen. In some embodiments, the target antigen is a tumor antigen. In some embodiments, the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CSPG4, CTLA-4, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGFI)-1, intestinal carboxyl esterase, kappa chain, LAGA-Ia, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostase specific antigen (PSA), prostate-carcinoma tumor antigen-1 (PCTA-1), prostate-specific antigen, prostein, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C(TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers. In some embodiments, the antigen binding molecule specifically binds to BCMA. In one embodiment the antigen binding molecule that specifically binds to BCMA is encoded by the nucleic sequence:

(SEQ ID NO: 10)
CAGGTGCAGCTGGTGGAGTCTGGGGGAGGCGTGGTCCAGCCTGGGAGGTC

CCTGAGACTCTCCTGTGCAGCGTCTGGATTCACCTTCAGTAGCTATGGCA

TGCACTGGGTCCGCCAGGCTCCAGGCAAGGGGCTGGAGTGGGTGGCAGTT

ATATCGTATGATGGAAGTAATAAATACTATGCAGACTCCGTGAAGGGCCG

ATTCACCATCTCCAGAGACAATTCCAAGAACACGCTGTATCTGCAAATGA

ACAGCCTGAGAGCCGAGGACACGGCGGTGTACTACTGCGTCAAGGGGCCG

TTGCAGGAGCCGCCATACGATTATGGAATGGACGTATGGGGCCAGGGAAC

AACTGTCACCGTCTCCTCAGGGTCTACATCCGGCTCCGGGAAGCCCGGAA

GTGGCGAAGGTAGTACAAAGGGGGAAATAGTGATGACGCAGTCTCCAGCC

ACCCTGTCTGTGTCTCCAGGGGAAAGAGCCACCCTCTCCTGCAGGGCCAG

TCAGAGTGTTAGCAGCAACTTAGCCTGGTACCAGCAGAAACCTGGCCAGG

CTCCCAGGCTCCTCATCTATAGCGCATCCACCAGGGCCACTGGTATCCCA

GCCAGGTTCAGTGGCAGTGGGTCTGGGACAGAGTTCACTCTCACCATCAG

CAGCCTGCAGTCTGAAGATTTTGCAGTTTATTACTGTCAGCAGCACCACG

TCTGGCCTCTCACTTTTGGCGGAGGGACCAAGGTTGAGATCAAACGG and comprises the amino acid sequence:

(SEQ ID NO: 11)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCVKGP

LQEPPYDYGMDVWGQGTTVTVSSGSTSGSGKPGSGEGSTKGEIVMTQSPA

TLSVSPGERATLSCRASQSVSSNLAWYQQKPGQAPRLLIYSASTRATGIP

ARFSGSGSGTEFTLTISSLQSEDFAVYYCQQHHVWPLTFGGGTKVEIKR

In some embodiments, the antigen binding molecule specifically binds BCMA. In some embodiments, the antigen binding molecule comprises (a) a VH CDR1 comprising an amino acid sequence selected from SEQ ID NOs: 17 or 20; (b) a VH CDR2 comprising an amino acid sequence selected from SEQ ID NOs: 18 or 21; (c) a VH CDR3 comprising an amino acid sequence selected from SEQ ID NO: 19; (d) a VL CDR1 comprising an amino acid sequence selected from SEQ ID NO: 14; (e) a VL CDR2 comprising an amino acid sequence selected from SEQ ID NO: 15; and/or (f) a VL CDR3 comprising an amino acid sequence selected from SEQ ID NO: 16.

In some embodiments, the antigen binding molecule comprises a VH comprising an amino acid sequence selected from the group consisting of SEQ ID NO: 13 and a VL comprising an amino acid sequence selected from the group consisting of SEQ ID NO: 12.

In some embodiments, the polynucleotide disclosed herein comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 28, 29, 31, 33, 35, 37, 39, 41, 43, 45, 47, 49, and 51.

Other known anti-BCMA antibodies or antigen binding molecules thereof may be used as antigen binding molecules of a CAR disclosed herein. Non-limiting examples of such anti-BCMA antibodies or antigen binding molecule thereof include antibodies or antigen binding molecules described in, e.g., published applications US20170283504 and WO2016014565, the entirety of which is hereby incorporated by reference.

The antigen binding molecule encoded by the polynucleotide disclosed hereinmay be single chained or double chained. In some embodiments, the antigen binding molecule is single chained. In some embodiments, the antigen binding molecule is selected from the group consisting of an scFv, an Fab, an Fab', an Fv, an F(ab')2, a dAb, and any combination thereof. In some embodiments, the antigen binding molecule comprises an scFv.

In some embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises at least about 18 amino acids. In some embodiments, the linker comprises an amino acid sequence that is at least about 75%, at least about 85%, at least about 85%, at least about 90%, at least about 95%, at least about 96%, at least about 97%, at least about 98%, at least about 99%, or 100% identical to the amino acid sequence GSTSGSGKPGSGEGSTKG (SEQ ID NO: 26) or the amino acid sequence GGGGSGGGGSGGGGS (SEQ ID NO: 25). In some embodiments, the linker is a Whitlow linker (Whitlow et al., Protein Eng. 1993 November; 6(8): 989-95). In some embodiments, the binding molecule comprises a single chain, wherein the heavy chain variable region and the light chain variable region are connected by a linker, wherein the linker comprises the amino acid sequence of SEQ ID NO: 26.

In some embodiments, the antigen binding molecule binds a target antigen (e.g., human BCMA) with a KD of less than $1\times10^{-6}$ M, less than $1\times10^{-7}$ M, less than $1\times10^{-8}$ M, or less than $1\times10^{-9}$ M. In some embodiments, the antigen binding molecule binds a target antigen (e.g., human BCMA) with a KD of less than $1\times10^{-7}$ M. In another embodiment, the antigen binding molecule binds a target antigen (e.g., human BCMA) with a KD of less than $1\times10^{-8}$ M. In some embodiments, the antigen binding molecule binds a target antigen (e.g., human BCMA) with a KD of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. In some embodiments, the KD is calculated as the quotient of koff/kon, and the kon and koff are determined using a monovalent antibody, such as a Fab fragment, as measured by, e.g., BIAcore® surface plasmon resonance technology. In other embodiments, the KD is calculated as the quotient of koff/kon, and the kon and koff are determined using a bivalent antibody, such as a Fab fragment, as measured by, e.g., BIAcore® surface plasmon resonance technology.

In some embodiments, the antigen binding molecule binds a target antigen (e.g., human BCMA) with an association rate (kon) of less than $1\times10^{-4}$ $M^{-1}$ $s^{-1}$, less than $2\times10^{-4}$ $M^{-1}$ $s^{-1}$, less than $3\times10^{-4}$ $M^{-1}$ $s^{-1}$, less than $4\times10^{-4}$ $M^{-1}$ $s^{-1}$, less than $5\times10^{-4}$ M-1 $s^{-1}$, less than $6\times10^{-4}$ M-1 $s^{-1}$, less than $7\times10^{-4}$ $M^{-1}$ $s^{-1}$, less than $8\times10^{-4}$ $M^{-1}$ $s^{-1}$, less than $9\times10^{-4}$ $M^{-1}$ $s^{-1}$, less than $1\times10^{-5}$ $M^{-1}$ $s^{-1}$, less than $2\times10^{-5}$ $M^{-1}$ $s^{-1}$, less than $3\times10^{-5}$ $M^{-1}$ $s^{-1}$, less than $4\times10^{-5}$ $M^{-1}$ $s^{-1}$, less than $5\times10^{-5}$ $M^{-1}$ $s^{-1}$, less than $6\times10^{-5}$ $M^{-1}$ $s^{-1}$, less than $7\times10^{-5}$ $M^{-1}$ $s^{-1}$, less than $8\times10^{-5}$ $M^{-1}$ $s^{-1}$, less than $9\times10^{-5}$ $M^{-1}$ $s^{-1}$, less than $1\times10^{-6}$ $M^{-1}$ $s^{-1}$, less than $2\times10^{-6}$ $M^{-1}$ $s^{-1}$, less than $3\times10^{-6}$ $M^{-1}$ $s^{-1}$, less than $4\times10^{-6}$ $M^{-1}$ $s^{-1}$, less than $5\times10^{-6}$ $M^{-1}$ $s^{-1}$, less than $6\times10^{-6}$ $M^{-1}$ $s^{-1}$, less than $7\times10^{-6}$ $M^{-1}$ $s^{-1}$, less than $8\times10^{-6}$ $M^{-1}$ $s^{-1}$, less than $9\times10^{-6}$ $M^{-1}$ $s^{-1}$, or less than $1\times10^{-7}$ $M^{-1}$ $s^{-1}$. In some embodiments, the kon is determined using a monovalent antibody, such as a Fab fragment, as measured by, e.g., BIAcore® surface plasmon resonance technology. In other embodiments, the kon is determined using a bivalent antibody as measured by, e.g., BIAcore® surface plasmon resonance technology.

In some embodiments, the antigen binding molecule binds a target antigen (e.g., human BCMA) with an dissociation rate (koff) of less than $1\times10^{-2}$ $s^{-1}$, less than $2\times10^{-2}$ $s^{-1}$, less than $3\times10^{-2}$ $s^{-1}$, less than $4\times10^{-2}$ $s^{-1}$, less than $5\times10^{-2}$ $s^{-1}$, less than $6\times10^{-2}$ $s^{-1}$, less than $7\times10^{-2}$ $s^{-1}$, less than $8\times10^{-2}$ $s^{-1}$, less than $9\times10^{-2}$ $s^{-1}$, less than $1\times10^{-3}$ $s^{-1}$, less than $2\times10^{-3}$ $s^{-1}$, less than $3\times10^{-3}$ $s^{-1}$, less than $4\times10^{-3}$ $s^{-1}$, less than $5\times10^{-3}$ $s^{-1}$, less than $6\times10^{-3}$ $s^{-1}$, less than $7\times10^{-3}$ $s^{-1}$, less than $8\times10^{-3}$ $s^{-1}$, less than $9\times10^{-3}$ $s^{-1}$, less than $1\times10^{-4}$ $s^{-1}$, less than $2\times10^{-4}$ $s^{-1}$, less than $3\times10^{-4}$ $s^{-1}$, less than $4\times10^{-4}$ $s^{-1}$, less than $5\times10^{-4}$ $s^{-1}$, less than $6\times10^{-4}$ $s^{-1}$, less than $7\times10^{-4}$ $s^{-1}$, less than $8\times10^{-4}$ $s^{-1}$, less than $9\times10^{-4}$ $s^{-1}$, less than $1\times10^{-4}$ $s^{-1}$, or less than $5\times10^{-4}$ $s^{-1}$. In some embodiments, the koff is determined using a monovalent antibody, such as a Fab fragment, as measured by, e.g., BIAcore® surface plasmon resonance technology. In other embodiments, the koff is determined using a bivalent antibody as measured by, e.g., BIAcore® surface plasmon resonance technology.

Switch Domain

It will be appreciated that adverse events may be minimized by transducing the immune cells (containing one or more CARs) with a suicide gene. It may also be desired to incorporate an inducible "on" or "accelerator" switch into the immune cells. Suitable techniques include use of inducible caspase-9 (U.S. Pub. No. 2011/0286980) or a thymidine kinase, before, after or at the same time, as the cells are transduced with the CAR construct of the present invention. Additional methods for introducing suicide genes and/or "on" switches include TALENS, meganucleases, zinc fingers, RNAi, siRNA, shRNA, antisense technology, and other techniques known in the art.

In accordance with the disclosure, additional on-off or other types of control switch techniques may be incorporated herein. These techniques may employ the use of dimerization domains and optional activators of such domain dimerization. These techniques include, e.g., those described by Wu et al. (2014) Science. 350 6258, utilizing FKBP/Rapalog dimerization systems in certain cells, the contents of which are incorporated by reference herein in their entirety. Additional dimerization technology is described in, e.g., Fegan et al. (2010) Chem. Rev. 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology may be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

Leader Peptide

In some embodiments, the polypeptide disclosed herein comprising a CAR may further comprise a leader peptide (also referred to herein as a "signal peptide"). In some embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequences MALPVTALLLPLALLLHAARP (CD8a; SEQ ID NO: 22) or MLLLVTSLLLCELPHPAFLLIP (GM-CSF; SEQ ID NO: 23) or MDMRVPAQLLGLLLLWLRGARC (IgG kappa light chain; SEQ ID NO: 24). In some embodiments, the leader peptide comprises the amino acid sequence of SEQ ID NO: 22.

In some embodiments, the polypeptide disclosed herein comprises a CAR, wherein the CAR comprises a leader peptide (P), an antigen binding molecule (B), a costimulatory protein's extracellular domain (E), a transmembrane domain (T), a costimulatory region (C), and an activation domain (A), wherein the CAR is configured according to the following: P-B-E-T-C-A. In some embodiments, the antigen binding molecule comprises a VH and a VL, wherein the CAR is configured according to the following: P-VH-VL-E-T-C-A or P-VL-VH-E-T-C-A. In some embodiments, the VH and the VL are connected by a linker (L), wherein the CAR is configured according to the following, from N-terminus to C-terminus: P-VH-L-VL-E-T-C-A or P-VH-L-VL-E-T-C-A.

II. Vectors, Cells, and Pharmaceutical Compositions

In certain aspects, provided herein are vectors comprising a polynucleotide described in the present disclosure. In some embodiments, the present disclosure is directed to a vector or a set of vectors comprising a polynucleotide encoding a CAR comprising amino acid modifications in the (i) hinge/spacer domain, (ii) transmembrane domain, and/or (iii) intracellular domain, wherein the amino acid modification modulates the activity of a CART cell, as described above.

Any vector known in the art may be used. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In some aspects, provided herein are cells comprising a polynucleotide or a vector of the present disclosure. In some embodiments, the present disclosure is directed to cells, e.g., in vitro cells, comprising a polynucleotide encoding a CAR comprising an amino acid modification in the (i) hinge/spacer domain, (ii) transmembrane domain, and/or (iii) intracellular domain, wherein the amino acid modification modulates the activity of a CART cell described herein. In some embodiments, the present disclosure is directed to cells, e.g., in vitro cells, comprising a polypeptide encoded by a CAR comprising an amino acid modification in the (i) hinge/spacer domain, (ii) transmembrane domain, and/or (iii) intracellular domain, wherein the amino acid modification modulates the activity of a CAR T cell described herein.

Any cell may be used as a host cell for the polynucleotides, the vectors, or the polypeptides of the present disclosure. In some embodiments, the cell may be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In some embodiments, the immune cell is a T cell. In another embodiment, the immune cell is an NK cell. In some embodiments, the T cell is a tumor-infiltrating lymphocyte (TIL), autologous T cell, engineered autologous T cell (eACTN, an allogeneic T cell, a heterologous T cell, or any combination thereof.

The cell of the present disclosure may be obtained through any source known in the art. For example, T cells may be differentiated in vitro from a hematopoietic stem cell population, or T cells may be obtained from a subject. T cells may be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. In some embodiments, the cells collected by apheresis are washed to remove the plasma fraction, and placed in an appropriate buffer or media for subsequent processing. In some embodiments, the cells are washed with PBS. As will be appreciated, a washing step may be used, such as by using a semiautomated flowthrough centrifuge, e.g., the Cobe™ 2991 cell processor, the Baxter CytoMate™, or the like. In some embodiments, the washed cells are resuspended in one or more biocompatible buffers, or other saline solution with or without buffer. In some embodiments, the undesired components of the apheresis sample are removed. Additional methods of isolating T cells for a T cell therapy are disclosed in U.S. Patent Pub. No. 2013/0287748, which is herein incorporated by references in its entirety.

In some embodiments, T cells are isolated from PBMCs by lysing the red blood cells and depleting the monocytes, e.g., by using centrifugation through a PERCOLL™ gradient. In some embodiments, a specific subpopulation of T cells, such as CD4+, CD8+, CD28+, CD45RA+, and CD45RO+ T cells is further isolated by positive or negative selection techniques known in the art. For example, enrichment of a T cell population by negative selection may be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected may be used. For example, to enrich for CD4+ cells by negative selection, a monoclonal antibody cocktail typically includes antibodies to CD8, CD11b, CD14, CD16, CD20, and HLA-DR. In some embodiments, flow cytometry and cell sorting are used to isolate cell populations of interest for use in the present disclosure.

In some embodiments, PBMCs are used directly for genetic modification with the immune cells (such as CARs) using methods as described herein. In some embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, CD8+ cells are further sorted into naive, central memory, and effector cells by identifying cell surface antigens that are associated with each of these types of CD8+ cells. In some embodiments, the expression of phenotypic markers of central memory T cells includes CCR7, CD3, CD28, CD45RO, CD62L, and CD127 and are negative for granzyme B. In some embodiments, central memory T cells are CD8+, CD45RO+, and CD62L+ T cells. In some embodiments, effector T cells are negative for CCR7, CD28, CD62L, and CD127 and positive for granzyme B and perforin. In some embodiments, CD4+ T cells are further sorted into subpopulations. For example, CD4+T helper cells may be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In some embodiments, the T cells are obtained from a donor subject. In some embodiments, the donor subject is human patient afflicted with a cancer or a tumor. In some embodiments, the donor subject is a human patient not afflicted with a cancer or a tumor.

Some aspects of the present disclosure are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In some embodiments, the composition comprises a polynucleotide encoding a CAR comprising a modified costumulatory domain described herein. In some embodiments, the composition comprises a CAR comprising a modified costumulatory domain encoded by a polynucleotide disclosed herein. In some embodiments, the composition comprises a T cell comprising a CAR comprising a modified costumulatory domain described herein.

In some embodiments, the composition is selected for parenteral delivery, for inhalation, or for delivery through the digestive tract, such as orally. The preparation of such pharmaceutically acceptable compositions is within the ability of one skilled in the art. In some embodiments, buffers are used to maintain the composition at physiological pH or at a slightly lower pH, typically within a pH range of from about 5 to about 8. In some embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In some embodiments, the vehicle for parenteral injection is sterile distilled water in which composition described herein, with or without at least one additional therapeutic agent, is formulated as a sterile, isotonic solution, properly preserved. In some embodiments, the preparation involves the formulation of the desired molecule with polymeric compounds (such as polylactic acid or polyglycolic acid), beads or liposomes, that provide for the controlled or sustained release of the product, which are then be delivered via a depot injection. In some embodiments, implantable drug delivery devices are used to introduce the desired molecule.

III. Methods of Making and Using the Compositions

One aspect of the disclosure is directed to a method of making a cell expressing a CAR comprising transducing a cell with a polynucleotide encoding the CAR with a modified costumulatory domain disclosed herein under suitable conditions. In some embodiments, the method comprises transducing a cell with a polynucleotide encoding a CAR, as disclosed herein. In some embodiments, the method comprises transducing a cell with a vector comprising the polynucleotide encoding a CAR.

In one aspect of the present disclosure provides a method of inducing immunity against a tumor comprising administering to a subject an effective amount of a cell comprising a polynucleotide described herein, a vector described herein, or a CAR described herein. In some embodiments, the method comprises administering to a subject an effective amount of a cell comprising a polynucleotide encoding a CAR disclosed herein. In some embodiments, the method comprises administering to a subject an effective amount of a cell comprising a vector comprising a polynucleotide encoding a CAR disclosed herein. In some embodiments, the method comprises administering to a subject an effective amount of a cell comprising a CAR encoded by a polynucleotide disclosed herein.

Another aspect of the present disclosure is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR, wherein the CAR comprises a modified costumulatory domain described in the present disclosure. In some embodiments, the target cell is a tumor cell.

Another aspect of the present disclosure is directed to a method for treating or preventing a malignancy, the method comprising administering to a subject in need thereof an effective amount of at least one immune cell, wherein the immune cell comprises at least one CAR, and wherein the CAR comprises a modified costumulatory domain described herein.

Another aspect of the present disclosure is directed to a method of treating a cancer in a subject in need thereof comprising administering to the subject a polynucleotide, a vector, a CAR, a cell, or a composition disclosed herein. In some embodiments, the method comprises administering a polynucleotide encoding a CAR. In some embodiments, the method comprises administering a vector comprising a polynucleotide encoding a CAR. In some embodiments, the method comprises administering a CAR encoded by a polynucleotide disclosed herein. In another embodiment, the method comprises administering a cell comprising the polynucleotide, or a vector comprising the polynucleotide, encoding a CAR.

In some embodiments, the methods of treating a cancer in a subject in need thereof comprise a T cell therapy. In some embodiments, the T cell therapy disclosed herein is engineered Autologous Cell Therapy (eACT™). According to this embodiment, the method may include collecting blood cells from the patient. The isolated blood cells (e.g., T cells) may then be engineered to express a CAR or a TCR disclosed herein. In a particular embodiment, the CART cells or the TCR T cells are administered to the patient. In some embodiments, the CART cells or the TCR T cells treat a tumor or a cancer in the patient. In some embodiments, the CART cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

The T cells may be administered at a therapeutically effective amount. For example, a therapeutically effective amount of the T cells may be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In some embodiments, the therapeutically effective amount of the CART cells or the TCR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

IV. Cancer Treatment

The methods disclosed herein may be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In some embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In some embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CML), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, Waldenstrom macroglobulinemia, or a combination thereof.

In some embodiments, the cancer is a myeloma. In some embodiments, the cancer is multiple myeloma. In some embodiments, the cancer is a leukemia. In some embodiments, the cancer is acute myeloid leukemia.

In some embodiments, the methods further comprise administering a chemotherapeutic. In some embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m²/day and 2000 mg/m²/day) and specified doses of fludarabine (between 20 mg/m²/day and 900 mg/m²/day). One such dose regimen involves treating a patient comprising administering daily to the patient about 500 mg/m²/day of cyclophosphamide and about 60 mg/m²/day of fludarabine for three days prior to administration of a therapeutically effective amount of engineered T cells to the patient.

In some embodiments, the antigen binding molecule, transduced (or otherwise engineered) cells (such as CARs), and the chemotherapeutic agent are administered each in an amount effective to treat the disease or condition in the subject.

In some embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche).

Additional therapeutic agents suitable for use in combination with the compositions and methods disclosed herein include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR immune cells are administered with an anti-inflammatory agent. Anti-inflammatory agents or drugs may include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), non-steroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In some embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

All publications, patents, patent applications, and references, including GenBank or other database sequences, that are mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

EXAMPLES

The present invention is further illustrated by the following examples which should not be construed as further limiting.

Example 1: Modifications to the N-Linked Glycosylation Site

CART cells transduced with anti-BCMA CAR constructs comprising a CD28 hinge/spacer with an N-linked glycosylation site (CARwt) or a hinge/spacer without the N-linked glycosylation site (CAR_aGlyco) were co-cultured with target cells including EoL-1 (Sigma; BCMA negative), and MM.1S (Molecular Imaging; BCMA positive). T cells expressing an anti-BCMA CAR with a CD28 hinge/spacer show different levels of proliferation when the hinge/spacer has an N-linked glycosylation site or with the N-linked glycosylation site removed. As shown in FIG. 1, proliferation after 72 hours in a co-culture with MMIS cells (BCMA-expressing cells). Compared to mock-transduced T cells, the anti-BCMA CAR constructs show a number of replications, as seen in the left shift of the cell trace violet dye. The construct with the glycan removed shows even more proliferation. This trend is also observed in the absence of antigen, as seen when the T cells were co-cultured with Eol-1 cells, which do not express BCMA. The construct without the N-linked glycan shows more target-independent proliferation when compared to mock- or wild-type anti-BCMA CAR-transduced T cells. T cell proliferation was assessed by flow cytometric analysis of CellTrace™ Violet dye (ThermoFisher Scientific) dilution.

Example 2: Oligomerization Propensity Modulates T Cell Proliferation

Figure 2:
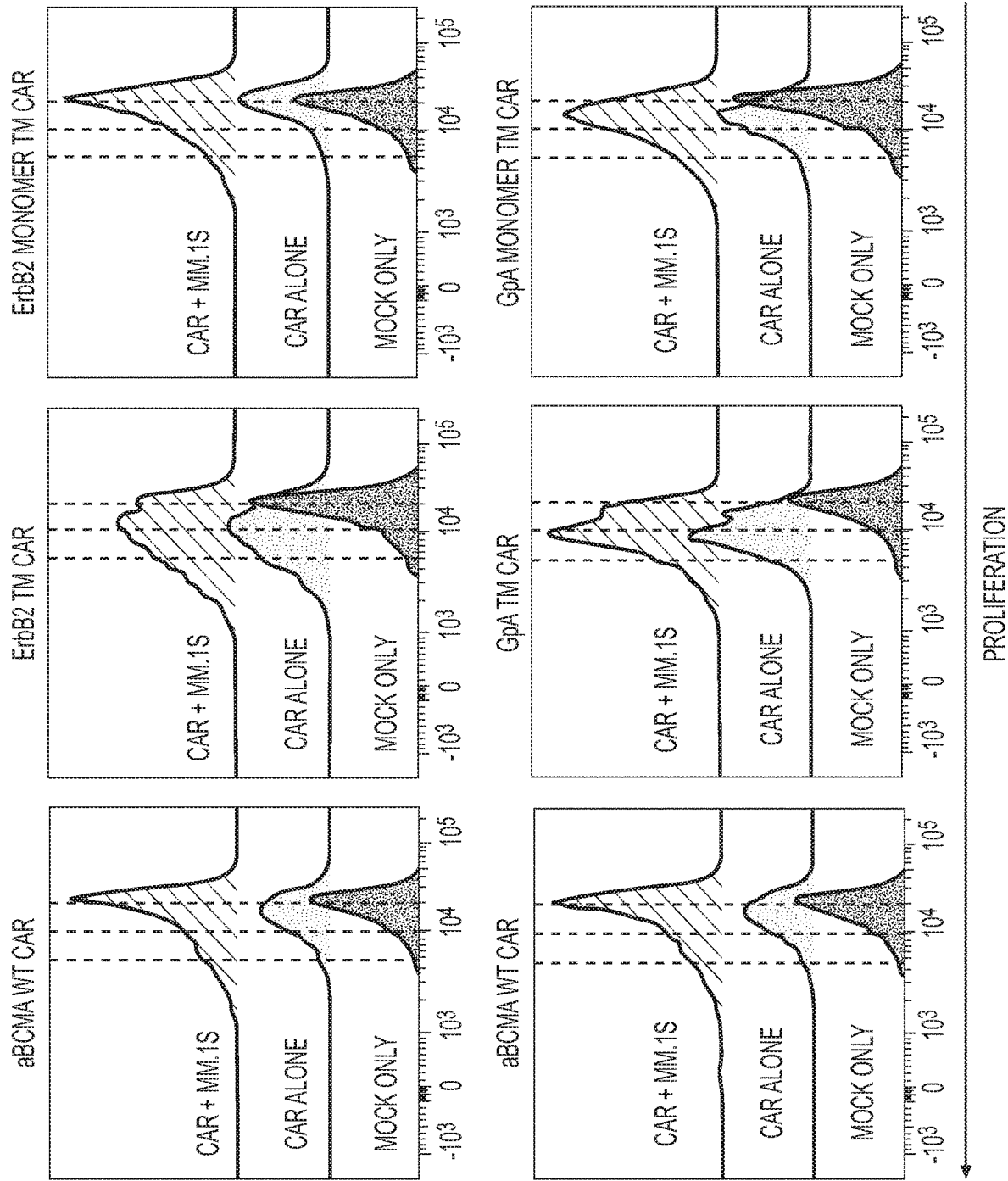
FIG. 2 shows proliferation of as measured using the CellTrace™ Violet Cell Proliferation Kit (ThermoFisher Scientific). Anti-BCMA CAR expressing T cells (CAR alone), control mock-transduced T cells (Mock only) or anti-BCMA CAR expressing T cells co-cultured with BCMA-positive MM1S cells (CAR+MM.1S) are shown. On the left (top and bottom), anti-BCMA CAR expressing T cell proliferation is shown compared to mock-transduced T cells. Domain swap with known dimerization domains or their monomeric constructs are shown (ErbB2, top and GpA, bottom).

Changing the transmembrane region of a CAR has a large effect on the ability of the CAR to self-associate on the surface of a cell. ErbB2 and glycophorin A (GpA) are examples of proteins known to dimerize on the surface of a cell. These proteins (e.g., receptor tyrosine kinases (RTK), GpA) include a single pass transmembrane segment that interact through a GXXXG motif. The transmembrane regions of ErbB2 and GpA have been mutated to eliminate this dimerization (Lemmon et al. J Biol Chem. 1992 Apr. 15; 267(11):7683-9; Mendrola et al. J Biol Chem. 2002 Feb. 15; 277(7):4704-12. Epub 2001 Dec. 10, 2002). Comparing CAR constructs with an anti-BCMA scFv, varying only the transmembrane (TM) segment allows characterization of the effect of a dimeric versus a monomeric CAR. Proliferation is increased when the dimeric construct is used versus the monomeric construct as shown in FIG. 2.

Introducing dimeric transmembrane segments into a CAR leads to increased proliferation of CART cells when grown alone or cultured with BCMA-positive MM.1S cells. As shown in FIG. 2, on the left (top and bottom), anti-BCMA CAR expressing T cell proliferation is shown compared to mock-transduced T cells. In the presence of BCMA expressing MM1S cells, proliferation increases. ErbB2 and GpA constructs are expected to dimerize on the cell surface and show increased antigen-independent proliferation. Introducing mutations to force these to form monomeric CARs leads to reduced antigen-independent proliferation as seen in the right plots (ErbB2, top and GpA, bottom). T cell proliferation was assessed by flow cytometric analysis of Cell-Trace™ Violet dye (ThermoFisher Scientific) dilution.

Example 3: Modified Transmembrane Domains Modulate Cytokine Levels

Figure 3A:
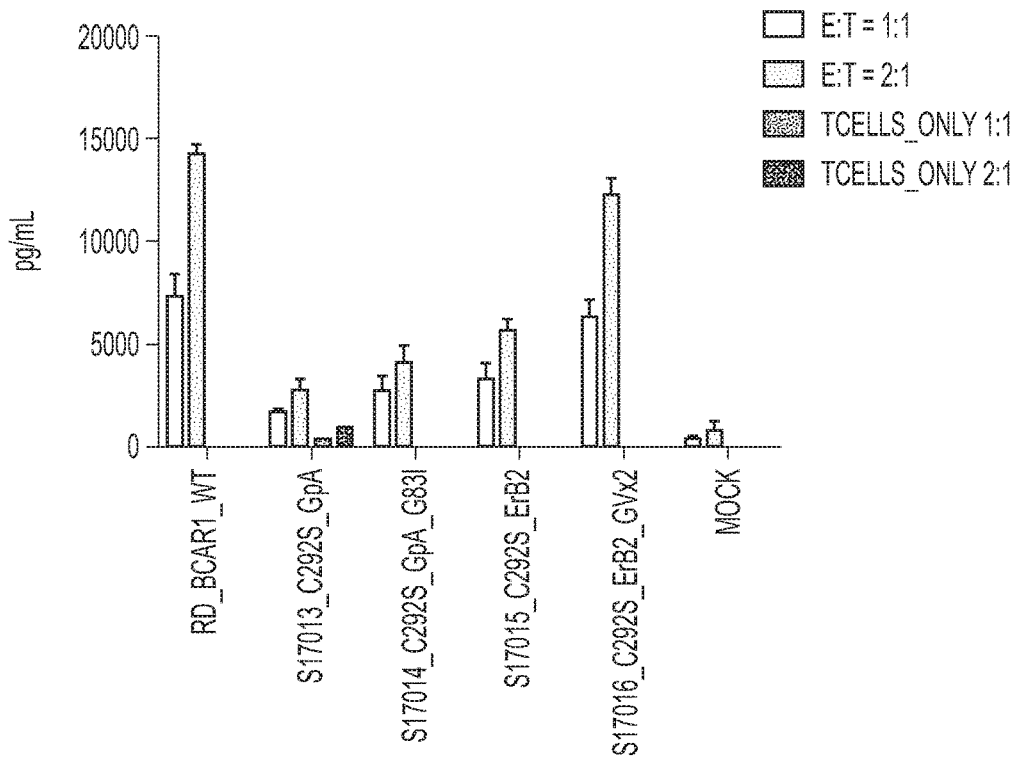
FIGS. 3A and 3B show cytokine production by anti-BCMA CAR expressing T cells as measured by Meso Scale Discovery (MSD) multiplex assay.
Figure 3B:
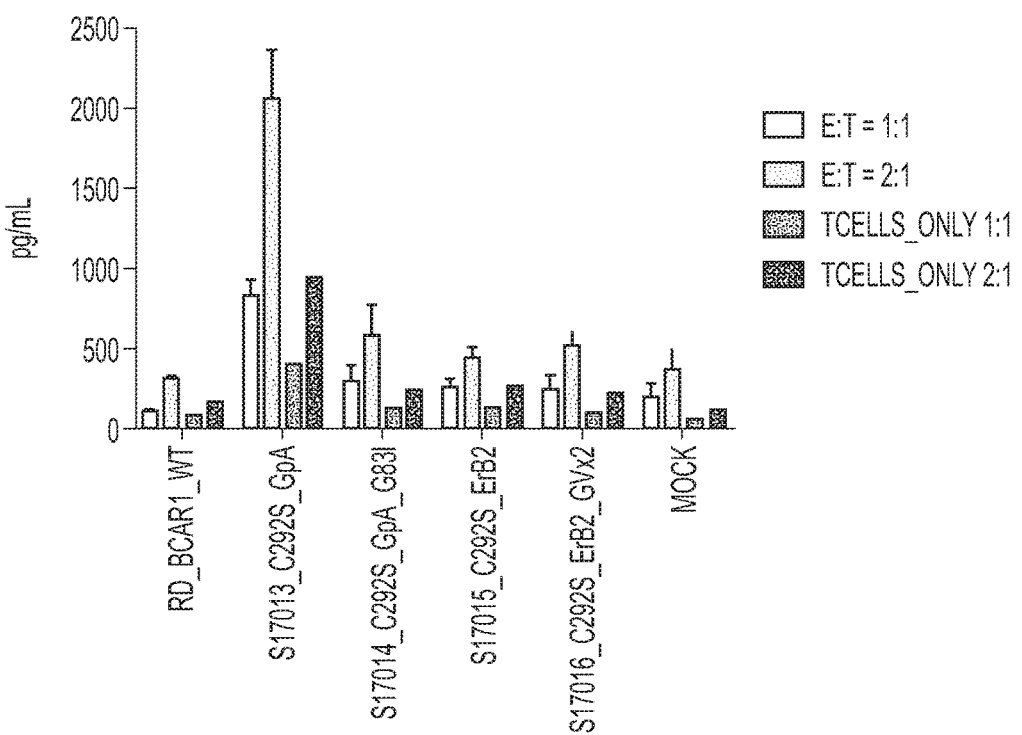

Changing the transmembrane (TM) region of a CAR may also modulate cytokine levels. Anti-BCMA CART cells with modified transmembrane domains including C292S substitution in the CD28 hinge, GpA, ErbB2, and their respective monomeric variants were co-cultured with target cells (e.g., EoL-1 (Sigma; BCMA negative) (FIG. 3B), MM.1S (Molecular Imaging; BCMA positive) (FIG. 3A)) at a 1:1 or 2:1 effector cell to target cell (E:T) ratio. The post-co-culture, supernatants were analyzed by Meso Scale Discovery (MSD) multiplex assay. As shown in FIGS. 3A and 3B, introduction of TM substitutions leads to reduced cytokine production compared to the CAR construct with the CD28 TM domain. Observed target-independent cytokine production was very low, except for the construct with the GpA dimer TM, though this was still at levels well below that seen in the presence of BCMA expressing cells.

Sequences and Seq Id Numbers

The instant disclosure comprises a number of nucleic acid and polypeptide sequences. For convenience, Table C below correlates each sequence with its appropriate SEQ ID NO.

TABLE C

| SEQ ID NO | SEQUENCE |
|---|---|
| SEQ ID NO: 1 | M A L P V T A L L L P L A L L L H A A R P Q V Q L V E S<br>G G G V V Q P G R S L R L S C A A S G F T F S S Y<br>G M H W V R Q A P G K G L E W V A V I S Y D G S N K<br>Y Y A D S V K G R F T I S R D N S K N T L Y L Q M N S L<br>R A E D T A V Y Y C V K G P L Q E P P Y D Y G M D V<br>W G Q G T T V T V S S G S T S G S G K P G S G E G S T<br>K G E I V M T Q S P A T L S V S P G E R A T L S C R A S<br>Q S V S S N L A W Y Q Q K P G Q A P R L L I Y S A S T R<br>A T G I P A R F S G S G S G T E F T L T I S S L Q S E D F<br>A V Y Y C Q Q H H V W P L T F G G G T K V E I K R A A<br>A L D N E K S N G T I I H V K G K H L C P S P L F P G P<br>S K P F W V L V V V G G V L A C Y S L L V T V A F I I F<br>W V R S K R S R L L H S D Y M N M T P R R P G P T R K<br>H Y Q P Y A P P R D F A A Y R S R V K F S R S A D A P A<br>Y Q Q G Q N Q L Y N E L N L G R R E E Y D V L D K R R<br>G R D P E M G G K P R R K N P Q E G L Y N E L Q K D<br>K M A E A Y S E I G M K G E  R R R G K G H D G L Y Q G<br>L S T A T K D T Y D A L H M Q A L P P R |
| SEQ ID NO: 2 | MLRLLLALNL FPSIQVTGNK ILVKQSPMLV<br>AYDNAVNLSC KYSYNLFSRE<br>FRASLHKGLDSAVEVCVVYG NYSQQLQVYS<br>KTGFNCDGKL GNESVTFYLQ NLYVNQTDIY<br>FCKIEVMYPPPYLDNEKSNG TIIHVKGKHL CPSPLFPGPS<br>KPFWVLVVVG GVLACYSLLV<br>TVAFIIFWVRSKRSRLLHSD YMNMTPRRPG<br>PTRKHYQPYA PPRDFAAYRS |
| SEQ ID NO: 3 | MLRLLLALNL FPSIQVTGNK ILVKQSPMLV<br>AYDNAVNLSC KYSYNLFSRE<br>FRASLHKGLDSAVEVCVVYG NYSQQLQVYS<br>KTGFNCDGKL GNESVTFYLQ NLYVNQTDIY<br>FCKIEVMYPPPYLDNEKSQG AIIHVKGKHL CPSPLFPGPS<br>KPFWVLVVVG GVLACYSLLV<br>TVAFIIFWVRSKRSRLLHSD YMNMTPRRPG<br>PTRKHYQPYA PPRDFAAYRS |
| SEQ ID NO: 4 | MLRLLLALNL FPSIQVTGNK ILVKQSPMLV<br>AYDNAVNLSC KYSYNLFSRE<br>FRASLHKGLDSAVEVCVVYG NYSQQLQVYS<br>KTGFNCDGKL GNESVTFYLQ NLYVNQTDIY<br>FCKIEVMYPPPYLDNEKSQGTIIHVKGKHL CPSPLFPGPS<br>KPFWVLVVVG GVLACYSLLV<br>TVAFIIFWVRSKRSRLLHSD YMNMTPRRPG<br>PTRKHYQPYA PPRDFAAYRS |
| SEQ ID NO: 5 | MLRLLLALNL FPSIQVTGNK ILVKQSPMLV<br>AYDNAVNLSC KYSYNLFSRE<br>FRASLHKGLDSAVEVCVVYG NYSQQLQVYS<br>KTGFNCDGKL GNESVTFYLQ NLYVNQTDIY<br>FCKIEVMYPPPYLDNEKSNG AIIHVKGKHL CPSPLFPGPS<br>KPFWVLVVVG GVLACYSLLV<br>TVAFIIFWVRSKRSRLLHSD YMNMTPRRPG<br>PTRKHYQPYA PPRDFAAYRS |
| SEQ ID NO: 6 | MLRLLLALNL FPSIQVTGNK ILVKQSPMLV<br>AYDNAVNLSC KYSYNLFSRE<br>FRASLHKGLDSAVEVCVVYG NYSQQLQVYS<br>KTGFNCDGKL GNESVTFYLQ NLYVNQTDIY<br>FCKIEVMYPPPYLDNEKSNGTIIHVKGKHL SPSPLFPGPS<br>KPFWVLVVVG GVLACYSLLV<br>TVAFIIFWVRSKRSRLLHSD YMNMTPRRPG<br>PTRKHYQPYA PPRDFAAYRS |
| SEQ ID NO: 7 | MLRLLLALNL FPSIQVTGNK ILVKQSPMLV<br>AYDNAVNLSC KYSYNLFSRE<br>FRASLHKGLDSAVEVCVVYG NYSQQLQVYS<br>KTGFNCDGKL GNESVTFYLQ NLYVNQTDIY<br>FCKIEVMYPPPYLDNEKSNG TIIHVKGKHL SPSPLFPGPS<br>KPFWVLVVVG GVLAAYSLLV |

TABLE C-continued

| SEQ ID NO | SEQUENCE |
|---|---|
| | TVAFIIFWVRSKRSRLLHSD YMNMTPRRPG PTRKHYQPYA PPRDFAAYRS |
| SEQ ID NO: 8 | MLRLLLALNL FPSIQVTGNK ILVKQSPMLV AYDNAVNLSC KYSYNLFSRE FRASLHKGLDSAVEVCVVYG NYSQQLQVYS KTGFNCDGKL GNESVTFYLQ NLYVNQTDIY FCKIEVMYPPPYLDNEKSNG TIIHVKGKHL CPSPLFPGPS KPFWVLVVVG GVLAAYSLLV TVAFIIFWVRSKRSRLLHSD YMNMTPRRPG PTRKHYQPYA PPRDFAAYRS |
| SEQ ID NO: 9 | MLRLLLALNL FPSIQVTGNK ILVKQSPMLV AYDNAVNLSC KYSYNLFSRE FRASLHKGLDSAVEVCVVYG NYSQQLQVYS KTGFNCDGKL GNESVTFYLQ NLYVNQTDIY FCKIEVMYPPPYLDNEKSNG TIIHVKGKHL CPSPLFPGPS KPFWVLVVVG GVLAVYSLLV TVAFIIFWVRSKRSRLLHSD YMNMTPRRPG PTRKHYQPYA PPRDFAAYRS |
| SEQ ID NO: 10 | CAGGTGCAGCTGGTGGAGTCTGGGGGAGGCGTGGTC CAGCCTGGGAGGTCCCTGAGACTCTCCTGTGCAGCGT CTGGATTCACCTTCAGTAGCTATGGCATGCACTGGGTC CGCCAGGCTCCAGGCAAGGGGCTGGAGTGGGTGGCA GTTATATCGTATGATGGAAGTAATAAATACTATGCAGA CTCCGTGAAGGGCCGATTCACCATCTCCAGAGACAATT CCAAGAACACGCTGTATCTGCAAATGAACAGCCTGAG AGCCGAGGACACGGCGGTGTACTACTGCGTCAAGGG GCCGTTGCAGGAGCCGCCATACGATTATGGAATGGAC GTATGGGGCCAGGGAACAACTGTCACCGTCTCCTCAG GGTCTACATCCGGCTCCGGGAAGCCCGGAAGTGGCGA AGGTAGTACAAAGGGGGAAATAGTGATGACGCAGTC TCCAGCCACCCTGTCTGTGTCTCCAGGGGAAAGAGCC ACCCTCTCCTGCAGGGCCAGTCAGAGTGTTAGCAGCA ACTTAGCCTGGTACCAGCAGAAACCTGGCCAGGCTCC CAGGCTCCTCATCTATAGCGCATCCACCAGGGCCACTG GTATCCCAGCCAGGTTCAGTGGCAGTGGGTCTGGGAC AGAGTTCACTCTCACCATCAGCAGCCTGCAGTCTGAAG ATTTTGCAGTTTATTACTGTCAGCAGCACCACGTCTGG CCTCTCACTTTTGGCGGAGGGACCAAGGTTGAGATCA AACGG |
| SEQ ID NO: 11 | QVQLVESGGGVVQPGRSLRLSCAASGFTFSSYGMHWV RQAPGKGLEWVAVISYDGSNKYYADSVKGRFTISRDNSK NTLYLQMNSLRAEDTAVYYCVKGPLQEPPYDYGMDVW GQGTTVTVSSGSTSGSGKPGSGEGSTKGEIVMTQSPATL SVSPGERATLSCRASQSVSSNLAWYQQKPGQAPRLLIYS ASTRATGIPARFSGSGSGTEFTLTISSLQSEDFAVYYCQQH HVWPLTFGGGTKVEIKR |
| SEQ ID NO: 12 | EIVMTQSPATLSVSPGERATLSCRASQSVSSNLAW YQQKPGQAPRLLIYSASTRATGIPARFSGSGSGTEF TLTISSLQSEDFAVYYCQQHHVWPLTFGGGTKVEI K |
| SEQ ID NO: 13 | QVQLVESGGGVVQPGRSLRLSCAASGFTFSSYGM HWVRQAPGKGLEWVAVISYDGSNKYYADSVKGR FTISRDNSKNTLYLQMNSLRAEDTAVYYCVKGPL QEPPYDYGMDVWGQGTTVTVSS |
| SEQ ID NO: 14 | RASQSVSSNLA |
| SEQ ID NO: 15 | SASTRAT |
| SEQ ID NO: 16 | QQHHVWPLT |
| SEQ ID NO: 17 | SYGMH |
| SEQ ID NO: 18 | VISYDGSNKYYADSVKG |
| SEQ ID NO: 19 | GPLQEPPYDYGMDV |
| SEQ ID NO: 20 | GFTFSSY |
| SEQ ID NO: 21 | SYDGSN |
| SEQ ID NO: 22 | MALPVTALLLPLALLLHAARP |

TABLE C-continued

| SEQ ID NO | SEQUENCE |
| --- | --- |
| SEQ ID NO: 23 | MLLLVTSLLLCELPHPAFLLIP |
| SEQ ID NO: 24 | MDMRVPAQLLGLLLLWLRGARC |
| SEQ ID NO: 25 | GGGGSGGGGSGGGGS |
| SEQ ID NO: 26 | GSTSGSGKPGSGEGSTKG |
| SEQ ID NO: 27 | RVKFSRSADAPAYQQGQNQLYNELNLGRREEYDVLDKR RGRDPEMGGKPRRKNPQEGLYNELQKDKMAEAYSEIG MKGERRRGKGHDGLYQGLSTATKDTYDALHMQALPPR |
| SEQ ID NO: 28 | ATGGCACTCCCCGTAACTGCTCTGCTGCTGCCGTTGGC ATTGCTCCTGCACGCCGCACGCCCGCAGGTGCAGCTG GTGGAGTCTGGGGGAGGCGTGGTCCAGCCTGGGAGG TCCCTGAGACTCTCCTGTGCAGCGTCTGGATTCACCTT CAGTAGCTATGGCATGCACTGGGTCCGCCAGGCTCCA GGCAAGGGGCTGGAGTGGGTGGCAGTTATATCGTAT GATGGAAGTAATAAATACTATGCAGACTCCGTGAAGG GCCGATTCACCATCTCCAGAGACAATTCCAAGAACACG CTGTATCTGCAAATGAACAGCCTGAGAGCCGAGGACA CGGCGGTGTACTACTGCGTCAAGGGGCCGTTGCAGGA GCCGCCATACGATTATGGAATGGACGTATGGGGCCAG GGAACAACTGTCACCGTCTCCTCAGGGTCTACATCCGG CTCCGGGAAGCCCGGAAGTGGCGAAGGTAGTACAAA GGGGGAAATAGTGATGACGCAGTCTCCAGCCACCCTG TCTGTGTCTCCAGGGGAAAGAGCCACCCTCTCCTGCAG GGCCAGTCAGAGTGTTAGCAGCAACTTAGCCTGGTAC CAGCAGAAACCTGGCCAGGCTCCCAGGCTCCTCATCTA TAGCGCATCCACCAGGGCCACTGGTATCCCAGCCAGG TTCAGTGGCAGTGGGTCTGGGACAGAGTTCACTCTCA CCATCAGCAGCCTGCAGTCTGAAGATTTTGCAGTTTAT TACTGTCAGCAGCACCACGTCTGGCCTCTCACTTTTGG CGGAGGGACCAAGGTTGAGATCAAACGGGCCGCTGC CCTTGATAATGAAAAGTCAAACGGAACAATCATTCACG TGAAGGGCAAGCACCTCTGTCCGTCACCCTTGTTCCCT GGTCCATCCAAGCCATTCTGGGTGTTGGTCGTAGTGG GTGGAGTCCTCGCTTGTTACTCTCTGCTCGTCACCGTG GCTTTTATAATCTTCTGGGTTAGATCCAAAAGAAGCCG CCTGCTCCATAGCGATTACATGAATATGACTCCACGCC GCCCTGGCCCCACAAGGAAACACTACCAGCCTTACGC ACCACCTAGAGATTTCGCTGCCTATCGGAGCAGGGTG AAGTTTTCCAGATCTGCAGATGCACCAGCGTATCAGCA GGGCCAGAACCAACTGTATAACGAGCTCAACCTGGGA CGCAGGGAAGAGTATGACGTTTTGGACAAGCGCAGA GGACGGGACCCTGAGATGGGTGGCAAACCAAGACGA AAAAACCCCCAGGAGGGTCTCTATAATGAGCTGCAGA AGGATAAGATGGCTGAAGCCTATTCTGAAATAGGCAT GAAAGGAGAGCGGAGAAGGGGAAAAGGGCACGACG GTTTGTACCAGGGACTCAGCACTGCTACGAAGGATAC TTATGACGCTCTCCACATGCAAGCCCTGCCACCTAGGT AG |
| SEQ ID NO: 29 | ATGGCACTCCCCGTAACTGCTCTGCTGCTGCCGTTGGC ATTGCTCCTGCACGCCGCACGCCCGCAGGTGCAGCTG GTGGAGTCTGGGGGAGGCGTGGTCCAGCCTGGGAGG TCCCTGAGACTCTCCTGTGCAGCGTCTGGATTCACCTT CAGTAGCTATGGCATGCACTGGGTCCGCCAGGCTCCA GGCAAGGGGCTGGAGTGGGTGGCAGTTATATCGTAT GATGGAAGTAATAAATACTATGCAGACTCCGTGAAGG GCCGATTCACCATCTCCAGAGACAATTCCAAGAACACG CTGTATCTGCAAATGAACAGCCTGAGAGCCGAGGACA CGGCGGTGTACTACTGCGTCAAGGGGCCGTTGCAGGA GCCGCCATACGATTATGGAATGGACGTATGGGGCCAG GGAACAACTGTCACCGTCTCCTCAGGGTCTACATCCGG CTCCGGGAAGCCCGGAAGTGGCGAAGGTAGTACAAA GGGGGAAATAGTGATGACGCAGTCTCCAGCCACCCTG TCTGTGTCTCCAGGGGAAAGAGCCACCCTCTCCTGCAG GGCCAGTCAGAGTGTTAGCAGCAACTTAGCCTGGTAC CAGCAGAAACCTGGCCAGGCTCCCAGGCTCCTCATCTA TAGCGCATCCACCAGGGCCACTGGTATCCCAGCCAGG TTCAGTGGCAGTGGGTCTGGGACAGAGTTCACTCTCA CCATCAGCAGCCTGCAGTCTGAAGATTTTGCAGTTTAT TACTGTCAGCAGCACCACGTCTGGCCTCTCACTTTTGG CGGAGGGACCAAGGTTGAGATCAAACGGGCCGCTGC CCTTGATAATGAAAAGTCACAGGGAACAATCATTCAC GTGAAGGGCAAGCACCTCTGTCCGTCACCCTTGTTCCC |

TABLE C-continued

| SEQ ID NO | SEQUENCE |
|---|---|
|  | TGGTCCATCCAAGCCATTCTGGGTGTTGGTCGTAGTGG<br>GTGGAGTCCTCGCTTGTTACTCTCTGCTCGTCACCGTG<br>GCTTTTATAATCTTCTGGGTTAGATCCAAAAGAAGCCG<br>CCTGCTCCATAGCGATTACATGAATATGACTCCACGCC<br>GCCCTGGCCCCACAAGGAAACACTACCAGCCTTACGC<br>ACCACCTAGAGATTTCGCTGCCTATCGGAGCAGGGTG<br>AAGTTTTCCAGATCTGCAGATGCACCAGCGTATCAGCA<br>GGGCCAGAACCAACTGTATAACGAGCTCAACCTGGGA<br>CGCAGGGAAGAGTATGACGTTTTGGACAAGCGCAGA<br>GGACGGGACCCTGAGATGGGTGGCAAACCAAGACGA<br>AAAAACCCCCAGGAGGGTCTCTATAATGAGCTGCAGA<br>AGGATAAGATGGCTGAAGCCTATTCTGAAATAGGCAT<br>GAAAGGAGAGCGGAGAAGGGGAAAAGGGCACGACG<br>GTTTGTACCAGGGACTCAGCACTGCTACGAAGGATAC<br>TTATGACGCTCTCCACATGCAAGCCCTGCCACCTAGGT<br>AG |
| SEQ ID NO: 30 | M A L P V T A L L L P L A L L L H A A R P Q V Q L V E S<br>G G G V V Q P G R S L R L S C A A S G F T F S S Y<br>G M H W V R Q A P G K G L E W V A V I S Y D G S N K<br>Y Y A D S V K G R F T I S R D N S K N T L Y L Q M N S L<br>R A E D T A V Y Y C V K G P L Q E P P Y D Y G M D V<br>W G Q G T T V T V S S G S T S G S G K P G S G E G S T<br>K G E I V M T Q S P A T L S V S P G E R A T L S C R A S<br>Q S V S S N L A W Y Q Q K P G Q A P R L L I Y S A S T R<br>A T G I P A R F S G S G S G T E F T L T I S S L Q S E D F<br>A V Y Y C Q Q H H V W P L T F G G G T K V E I K R A A<br>A L D N E K S Q G T I I H V K G K H L C P S P L F P G P<br>S K P F W V L V V V G G V L A C Y S L L V T V A F I I F<br>W V R S K R S R L L H S D Y M N M T P R R P G P T R K<br>H Y Q P Y A P P R D F A A Y R S R V K F S R S A D A P A<br>Y Q Q G Q N Q L Y N E L N L G R R E E Y D V L D K R R<br>G R D P E M G G K P R R K N P Q E G L Y N E L Q K D<br>K M A E A Y S E I G M K G E R R G K G H D G L Y Q G<br>L S T A T K D T Y D A L H M Q A L P P R |
| SEQ ID NO: 31 | ATGGCACTCCCCGTAACTGCTCTGCTGCTGCCGTTGGC<br>ATTGCTCCTGCACGCCGCACGCCCGCAGGTGCAGCTG<br>GTGGAGTCTGGGGGAGGCGTGGTCCAGCCTGGGAGG<br>TCCCTGAGACTCTCCTGTGCAGCGTCTGGATTCACCTT<br>CAGTAGCTATGGCATGCACTGGGTCCGCCAGGCTCCA<br>GGCAAGGGGCTGGAGTGGGTGGCAGTTATATCGTAT<br>GATGGAAGTAATAAATACTATGCAGACTCCGTGAAGG<br>GCCGATTCACCATCTCCAGAGACAATTCCAAGAACACG<br>CTGTATCTGCAAATGAACAGCCTGAGAGCCGAGGACA<br>CGGCGGTGTACTACTGCGTCAAGGGGCCGTTGCAGGA<br>GCCGCCATACGATTATGGAATGGACGTATGGGGCCAG<br>GGAACAACTGTCACCGTCTCCTCAGGGTCTACATCCGG<br>CTCCGGGAAGCCCGGAAGTGGCGAAGGTAGTACAAA<br>GGGGGAAATAGTGATGACGCAGTCTCCAGCCACCCTG<br>TCTGTGTCTCCAGGGGAAAGAGCCACCCTCTCCTGCAG<br>GGCCAGTCAGAGTGTTAGCAGCAACTTAGCCTGGTAC<br>CAGCAGAAACCTGGCCAGGCTCCCAGGCTCCTCATCTA<br>TAGCGCATCCACCAGGGCCACTGGTATCCCAGCCAGG<br>TTCAGTGGCAGTGGGTCTGGGACAGAGTTCACTCTCA<br>CCATCAGCAGCCTGCAGTCTGAAGATTTTGCAGTTTAT<br>TACTGTCAGCAGCACCACGTCTGGCCTCTCACTTTTGG<br>CGGAGGGACCAAGGTTGAGATCAAACGGGCCGCTGC<br>CCTTGATAATGAAAAGTCAAACGGAGCCATCATTCACG<br>TGAAGGGCAAGCACCTCTGTCCGTCACCCTTGTTCCCT<br>GGTCCATCCAAGCCATTCTGGGTGTTGGTCGTAGTGG<br>GTGGAGTCCTCGCTTGTTACTCTCTGCTCGTCACCGTG<br>GCTTTTATAATCTTCTGGGTTAGATCCAAAAGAAGCCG<br>CCTGCTCCATAGCGATTACATGAATATGACTCCACGCC<br>GCCCTGGCCCCACAAGGAAACACTACCAGCCTTACGC<br>ACCACCTAGAGATTTCGCTGCCTATCGGAGCAGGGTG<br>AAGTTTTCCAGATCTGCAGATGCACCAGCGTATCAGCA<br>GGGCCAGAACCAACTGTATAACGAGCTCAACCTGGGA<br>CGCAGGGAAGAGTATGACGTTTTGGACAAGCGCAGA<br>GGACGGGACCCTGAGATGGGTGGCAAACCAAGACGA<br>AAAAACCCCCAGGAGGGTCTCTATAATGAGCTGCAGA<br>AGGATAAGATGGCTGAAGCCTATTCTGAAATAGGCAT<br>GAAAGGAGAGCGGAGAAGGGGAAAAGGGCACGACG<br>GTTTGTACCAGGGACTCAGCACTGCTACGAAGGATAC<br>TTATGACGCTCTCCACATGCAAGCCCTGCCACCTAGGT<br>AG |

TABLE C-continued

| SEQ ID NO | SEQUENCE |
| --- | --- |
| SEQ ID NO: 32 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I<br>V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y<br>C Q Q H H V W P L T F G G G T K V E I K R A A A L D N<br>E K S N G A I I H V K G K H L C P S P L F P G P S K P F<br>W V L V V V G G V L A C Y S L L V T V A F I I F W V R S<br>K R S R L L H S D Y M N M T P R R P G P T R K H Y Q P<br>Y A P P R D F A A Y R S R V K F S R S A D A P A Y Q Q<br>G Q N Q L Y N E L N L G R R E E Y D V L D K R R G R D<br>P E M G G K P R R K N P Q E G L Y N E L Q K D K M A<br>E A Y S E I G M K G E R R R G K G H D G L Y Q G L S T<br>A T K D T Y D A L H M Q A L P P R |
| SEQ ID NO: 33 | ATGGCACTCCCCGTAACTGCTCTGCTGCTGCCGTTGGC<br>ATTGCTCCTGCACGCCGCACGCCCGCAGGTGCAGCTG<br>GTGGAGTCTGGGGGAGGCGTGGTCCAGCCTGGGAGG<br>TCCCTGAGACTCTCCTGTGCAGCGTCTGGATTCACCTT<br>CAGTAGCTATGGCATGCACTGGGTCCGCCAGGCTCCA<br>GGCAAGGGGCTGGAGTGGGTGGCAGTTATATCGTAT<br>GATGGAAGTAATAAATACTATGCAGACTCCGTGAAGG<br>GCCGATTCACCATCTCCAGAGACAATTCCAAGAACACG<br>CTGTATCTGCAAATGAACAGCCTGAGAGCCGAGGACA<br>CGGCGGTGTACTACTGCGTCAAGGGGCCGTTGCAGGA<br>GCCGCCATACGATTATGGAATGGACGTATGGGGCCAG<br>GGAACAACTGTCACCGTCTCCTCAGGGTCTACATCCGG<br>CTCCGGGAAGCCCGGAAGTGGCGAAGGTAGTACAAA<br>GGGGGAAATAGTGATGACGCAGTCTCCAGCCACCCTG<br>TCTGTGTCTCCAGGGGAAAGAGCCACCCTCTCCTGCAG<br>GGCCAGTCAGAGTGTTAGCAGCAACTTAGCCTGGTAC<br>CAGCAGAAACCTGGCCAGGCTCCCAGGCTCCTCATCTA<br>TAGCGCATCCACCAGGGCCACTGGTATCCCAGCCAGG<br>TTCAGTGGCAGTGGGTCTGGGACAGAGTTCACTCTCA<br>CCATCAGCAGCCTGCAGTCTGAAGATTTTGCAGTTTAT<br>TACTGTCAGCAGCACCACGTCTGGCCTCTCACTTTTGG<br>CGGAGGGACCAAGGTTGAGATCAAACGGGCCGCTGC<br>CCTTGATAATGAAAAGTCAAACGGAACAATCATTCACG<br>TGAAGGGCAAGCACCTCTCCCCGTCACCCTTGTTCCCT<br>GGTCCATCCAAGCCATTCTGGGTGTTGGTCGTAGTGG<br>GTGGAGTCCTCGCTTGTTACTCTCTGCTCGTCACCGTG<br>GCTTTTATAATCTTCTGGGTTAGATCCAAAAGAAGCCG<br>CCTGCTCCATAGCGATTACATGAATATGACTCCACGCC<br>GCCCTGGCCCCACAAGGAAACACTACCAGCCTTACGC<br>ACCACCTAGAGATTTCGCTGCCTATCGGAGCAGGGTG<br>AAGTTTTCCAGATCTGCAGATGCACCAGCGTATCAGCA<br>GGGCCAGAACCAACTGTATAACGAGCTCAACCTGGGA<br>CGCAGGGAAGAGTATGACGTTTTGGACAAGCGCAGA<br>GGACGGGACCCTGAGATGGGTGGCAAACCAAGACGA<br>AAAAACCCCCAGGAGGGTCTCTATAATGAGCTGCAGA<br>AGGATAAGATGGCTGAAGCCTATTCTGAAATAGGCAT<br>GAAAGGAGAGCGGAGAAGGGGAAAAGGGCACGACG<br>GTTTGTACCAGGGACTCAGCACTGCTACGAAGGATAC<br>TTATGACGCTCTCCACATGCAAGCCCTGCCACCTAGGT<br>AG |
| SEQ ID NO: 34 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I<br>V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y<br>C Q Q H H V W P L T F G G G T K V E I K R A A A L D N<br>E K S N G T I I H V K G K H L S P S P L F P G P S K P F<br>W V L V V V G G V L A C Y S L L V T V A F I I F W V R S<br>K R S R L L H S D Y M N M T P R R P G P T R K H Y Q P<br>Y A P P R D F A A Y R S R V K F S R S A D A P A Y Q Q<br>G Q N Q L Y N E L N L G R R E E Y D V L D K R R G R D |

TABLE C-continued

| SEQ ID NO | SEQUENCE |
|---|---|
| | P E M G G K P R R K N P Q E G L Y N E L Q K D K M A<br>E A Y S E I G M K G E R R R G K H D G L Y Q G L S T<br>A T K D T Y D A L H M Q A L P P R |
| SEQ ID NO: 35 | ATGGCACTCCCCGTAACTGCTCTGCTGCTGCCGTTGGC<br>ATTGCTCCTGCACGCCGCACGCCCGCAGGTGCAGCTG<br>GTGGAGTCTGGGGGAGGCGTGGTCCAGCCTGGGAGG<br>TCCCTGAGACTCTCCTGTGCAGCGTCTGGATTCACCTT<br>CAGTAGCTATGGCATGCACTGGGTCCGCCAGGCTCCA<br>GGCAAGGGGCTGGAGTGGGTGGCAGTTATATCGTAT<br>GATGAAGTAATAAATACTATGCAGACTCCGTGAAGG<br>GCCGATTCACCATCTCCAGAGACAATTCCAAGAACACG<br>CTGTATCTGCAAATGAACAGCCTGAGAGCCGAGGACA<br>CGGCGGTGTACTACTGCGTCAAGGGGCCGTTGCAGGA<br>GCCGCCATACGATTATGGAATGGACGTATGGGCCAG<br>GGAACAACTGTCACCGTCTCCTCAGGGTCTACATCCGG<br>CTCCGGGAAGCCCGGAAGTGGCGAAGGTAGTACAAA<br>GGGGGAAATAGTGATGACGCAGTCTCCAGCCACCCTG<br>TCTGTGTCTCCAGGGGAAAGAGCCACCCTCTCCTGCAG<br>GGCCAGTCAGAGTGTTAGCAGCAACTTAGCCTGGTAC<br>CAGCAGAAACCTGGCCAGGCTCCCAGGCTCCTCATCTA<br>TAGCGCATCCACCAGGGCCACTGGTATCCCAGCCAGG<br>TTCAGTGGCAGTGGGTCTGGGACAGAGTTCACTCTCA<br>CCATCAGCAGCCTGCAGTCTGAAGATTTTGCAGTTTAT<br>TACTGTCAGCAGCACCACGTCTGGCCTCTCACTTTTGG<br>CGGAGGGACCAAGGTTGAGATCAAACGGGCCGCTGC<br>CCTTGATAATGAAAAGTCAAACGGAACAATCATTCACG<br>TGAAGGGCAAGCACCTCGACCCGTCACCCTTGTTCCCT<br>GGTCCATCCAAGCCATTCTGGGTGTTGGTCGTAGTGG<br>GTGGAGTCCTCGCTTGTTACTCTCTGCTCGTCACCGTG<br>GCTTTTATAATCTTCTGGGTTAGATCCAAAAGAAGCCG<br>CCTGCTCCATAGCGATTACATGAATATGACTCCACGCC<br>GCCCTGGCCCCACAAGGAAACACTACCAGCCTTACGC<br>ACCACCTAGAGATTTCGCTGCCTATCGGAGCAGGGTG<br>AAGTTTTCCAGATCTGCAGATGCACCAGCGTATCAGCA<br>GGGCCAGAACCAACTGTATAACGAGCTCAACCTGGGA<br>CGCAGGGAAGAGTATGACGTTTTGGACAAGCGCAGA<br>GGACGGGACCCTGAGATGGGTGGCAAACCAAGACGA<br>AAAAACCCCCAGGAGGGTCTCTATAATGAGCTGCAGA<br>AGGATAAGATGGCTGAAGCCTATTCTGAAATAGGCAT<br>GAAAGGAGAGCGGAGAAGGGGAAAAGGGCACGACG<br>GTTTGTACCAGGGACTCAGCACTGCTACGAAGGATAC<br>TTATGACGCTCTCCACATGCAAGCCCTGCCACCTAGGT<br>AG |
| SEQ ID NO: 36 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I<br>V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y<br>C Q Q H H V W P L T F G G G T K V E I K R A A A L D N<br>E K S N G T I I H V K G K H L D P S P L F P G P S K P F<br>W V L V V V G G V L A C Y S L L V T V A F I I F W V R S<br>K R S R L L H S D Y M N M T P R R P G P T R K H Y Q P<br>Y A P P R D F A A Y R S R V K F S R S A D A P A Y Q Q<br>G Q N Q L Y N E L N L G R R E E Y D V L D K R R G R D<br>P E M G G K P R R K N P Q E G L Y N E L Q K D K M A<br>E A Y S E I G M K G E R R R G K H D G L Y Q G L S T<br>A T K D T Y D A L H M Q A L P P R |
| SEQ ID NO: 37 | ATGGCACTCCCCGTAACTGCTCTGCTGCTGCCGTTGGC<br>ATTGCTCCTGCACGCCGCACGCCCGCAGGTGCAGCTG<br>GTGGAGTCTGGGGGAGGCGTGGTCCAGCCTGGGAGG<br>TCCCTGAGACTCTCCTGTGCAGCGTCTGGATTCACCTT<br>CAGTAGCTATGGCATGCACTGGGTCCGCCAGGCTCCA<br>GGCAAGGGGCTGGAGTGGGTGGCAGTTATATCGTAT<br>GATGAAGTAATAAATACTATGCAGACTCCGTGAAGG<br>GCCGATTCACCATCTCCAGAGACAATTCCAAGAACACG<br>CTGTATCTGCAAATGAACAGCCTGAGAGCCGAGGACA<br>CGGCGGTGTACTACTGCGTCAAGGGGCCGTTGCAGGA<br>GCCGCCATACGATTATGGAATGGACGTATGGGCCAG<br>GGAACAACTGTCACCGTCTCCTCAGGGTCTACATCCGG<br>CTCCGGGAAGCCCGGAAGTGGCGAAGGTAGTACAAA<br>GGGGGAAATAGTGATGACGCAGTCTCCAGCCACCCTG |

TABLE C-continued

| SEQ ID NO | SEQUENCE |
| --- | --- |
| | TCTGTGTCTCCAGGGGAAAGAGCCACCCTCTCCTGCAG GGCCAGTCAGAGTGTTAGCAGCAACTTAGCCTGGTAC CAGCAGAAACCTGGCCAGGCTCCCAGGCTCCTCATCTA TAGCGCATCCACCAGGGCCACTGGTATCCCAGCCAGG TTCAGTGGCAGTGGGTCTGGGACAGAGTTCACTCTCA CCATCAGCAGCCTGCAGTCTGAAGATTTTGCAGTTTAT TACTGTCAGCAGCACCACGTCTGGCCTCTCACTTTTGG CGGAGGGACCAAGGTTGAGATCAAACGGGCCGCTGC CCTTGATAATGAAAAGTCAAACGGAACAATCATTCACG TGAAGGGCAAGCACCTCTGTCCGTCACCCTTGTTCCCT GGTCCATCCAAGCCATTCTGGGTGTTGGTCGTAGTGG GTGGAGTCCTCGCTGCTTACTCTCTGCTCGTCACCGTG GCTTTTATAATCTTCTGGGTTAGATCCAAAAGAAGCCG CCTGCTCCATAGCGATTACATGAATATGACTCCACGCC GCCCTGGCCCCACAAGGAAACACTACCAGCCTTACGC ACCACCTAGAGATTTCGCTGCCTATCGGAGCAGGGTG AAGTTTTCCAGATCTGCAGATGCACCAGCGTATCAGCA GGGCCAGAACCAACTGTATAACGAGCTCAACCTGGGA CGCAGGGAAGAGTATGACGTTTTGGACAAGCGCAGA GGACGGGACCCTGAGATGGGTGGCAAACCAAGACGA AAAAACCCCCAGGAGGGTCTCTATAATGAGCTGCAGA AGGATAAGATGGCTGAAGCCTATTCTGAAATAGGCAT GAAAGGAGAGCGGAGAAGGGGAAAAGGGCACGACG GTTTGTACCAGGGACTCAGCACTGCTACGAAGGATAC TTATGACGCTCTCCACATGCAAGCCCTGCCACCTAGGT AG |
| SEQ ID NO: 38 | M A L P V T A L L L P L A L L L H A A R P Q V Q L V E S G G G V V Q P G R S L R L S C A A S G F T F S S Y G M H W V R Q A P G K G L E W V A V I S Y D G S N K Y Y A D S V K G R F T I S R D N S K N T L Y L Q M N S L R A E D T A V Y Y C V K G P L Q E P P Y D Y G M D V W G Q G T T V T V S S G S T S G S G K P G S G E G S T K G E I V M T Q S P A T L S V S P G E R A T L S C R A S Q S V S S N L A W Y Q Q K P G Q A P R L L I Y S A S T R A T G I P A R F S G S G S G T E F T L T I S S L Q S E D F A V Y Y C Q Q H H V W P L T F G G G T K V E I K R A A A L D N E K S N G T I I H V K G K H L C P S P L F P G P S K P F W V L V V V G G V L A A Y S L L V T V A F I I F W V R S K R S R L L H S D Y M N M T P R R P G P T R K H Y Q P Y A P P R D F A A Y R S R V K F S R S A D A P A Y Q Q G Q N Q L Y N E L N L G R R E E Y D V L D K R R G R D P E M G G K P R R K N P Q E G L Y N E L Q K D K M A E A Y S E I G M K G E R R R G K G H D G L Y Q G L S T A T K D T Y D A L H M Q A L P P R |
| SEQ ID NO: 39 | ATGGCACTCCCCGTAACTGCTCTGCTGCTGCCGTTGGC ATTGCTCCTGCACGCCGCACGCCCGCAGGTGCAGCTG GTGGAGTCTGGGGGAGGCGTGGTCCAGCCTGGGAGG TCCCTGAGACTCTCCTGTGCAGCGTCTGGATTCACCTT CAGTAGCTATGGCATGCACTGGGTCCGCCAGGCTCCA GGCAAGGGGCTGGAGTGGGTGGCAGTTATATCGTAT GATGGAAGTAATAAATACTATGCAGACTCCGTGAAGG GCCGATTCACCATCTCCAGAGACAATTCCAAGAACACG CTGTATCTGCAAATGAACAGCCTGAGAGCCGAGGACA CGGCGGTGTACTACTGCGTCAAGGGGCCGTTGCAGGA GCCGCCATACGATTATGGAATGGACGTATGGGGCCAG GGAACAACTGTCACCGTCTCCTCAGGGTCTACATCCGG CTCCGGGAAGCCCGGAAGTGGCGAAGGTAGTACAAA GGGGGAAATAGTGATGACGCAGTCTCCAGCCACCCTG TCTGTGTCTCCAGGGGAAAGAGCCACCCTCTCCTGCAG GGCCAGTCAGAGTGTTAGCAGCAACTTAGCCTGGTAC CAGCAGAAACCTGGCCAGGCTCCCAGGCTCCTCATCTA TAGCGCATCCACCAGGGCCACTGGTATCCCAGCCAGG TTCAGTGGCAGTGGGTCTGGGACAGAGTTCACTCTCA CCATCAGCAGCCTGCAGTCTGAAGATTTTGCAGTTTAT TACTGTCAGCAGCACCACGTCTGGCCTCTCACTTTTGG CGGAGGGACCAAGGTTGAGATCAAACGGGCCGCTGC CCTTGATAATGAAAAGTCAAACGGAACAATCATTCACG TGAAGGGCAAGCACCTCGACCCGTCACCCTTGTTCCCT GGTCCATCCAAGCCATTCTGGGTGTTGGTCGTAGTGG GTGGAGTCCTCGCTGCTTACTCTCTGCTCGTCACCGTG GCTTTTATAATCTTCTGGGTTAGATCCAAAAGAAGCCG CCTGCTCCATAGCGATTACATGAATATGACTCCACGCC GCCCTGGCCCCACAAGGAAACACTACCAGCCTTACGC ACCACCTAGAGATTTCGCTGCCTATCGGAGCAGGGTG AAGTTTTCCAGATCTGCAGATGCACCAGCGTATCAGCA GGGCCAGAACCAACTGTATAACGAGCTCAACCTGGGA |

TABLE C-continued

| SEQ ID NO | SEQUENCE |
|---|---|
| | CGCAGGGAAGAGTATGACGTTTTGGACAAGCGCAGA<br>GGACGGGACCCTGAGATGGGTGGCAAACCAAGACGA<br>AAAAACCCCCAGGAGGGTCTCTATAATGAGCTGCAGA<br>AGGATAAGATGGCTGAAGCCTATTCTGAAATAGGCAT<br>GAAAGGAGAGCGGAGAAGGGGAAAAGGGCACGACG<br>GTTTGTACCAGGGACTCAGCACTGCTACGAAGGATAC<br>TTATGACGCTCTCCACATGCAAGCCCTGCCACCTAGGT<br>AG |
| SEQ ID NO: 40 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I<br>V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y<br>C Q Q H H V W P L T F G G G T K V E I K R A A A L D N<br>E K S N G T I I H V K G K H L D P S P L F P G P S K P F<br>W V L V V V G G V L A A Y S L L V T V A F I I F W V R S<br>K R S R L L H S D Y M N M T P R R P G P T R K H Y Q P<br>Y A P P R D F A A Y R S R V K F S R S A D A P A Y Q Q<br>G Q N Q L Y N E L N L G R R E E Y D V L D K R R G R D<br>P E M G G K P R R K N P Q E G L Y N E L Q K D K M A<br>E A Y S E I G M K G E R R R G K G H D G L Y Q G L S T<br>A T K D T Y D A L H M Q A L P P R |
| SEQ ID NO: 41 | ATGGCACTCCCCGTAACTGCTCTGCTGCTGCCGTTGGC<br>ATTGCTCCTGCACGCCGCACGCCCGCAGGTGCAGCTG<br>GTGGAGTCTGGGGGAGGCGTGGTCCAGCCTGGGAGG<br>TCCCTGAGACTCTCCTGTGCAGCGTCTGGATTCACCTT<br>CAGTAGCTATGGCATGCACTGGGTCCGCCAGGCTCCA<br>GGCAAGGGGCTGGAGTGGGTGGCAGTTATATCGTAT<br>GATGGAAGTAATAAATACTATGCAGACTCCGTGAAGG<br>GCCGATTCACCATCTCCAGAGACAATTCCAAGAACACG<br>CTGTATCTGCAAATGAACAGCCTGAGAGCCGAGGACA<br>CGGCCGTGTACTACTGCGTCAAGGGGCCGTTGCAGGA<br>GCCGCCATACGATTATGGAATGGACGTATGGGGCCAG<br>GGAACAACTGTCACCGTCTCCTCAGGGTCTACATCCGG<br>CTCCGGGAAGCCCGGAAGTGGCGAAGGTAGTACAAA<br>GGGGGAAATAGTGATGACGCAGTCTCCAGCCACCCTG<br>TCTGTGTCTCCAGGGGAAAGAGCCACCCTCTCCTGCAG<br>GGCCAGTCAGAGTGTTAGCAGCAACTTAGCCTGGTAC<br>CAGCAGAAACCTGGCCAGGCTCCCAGGCTCCTCATCTA<br>TAGCGCATCCACCAGGGCCACTGGTATCCCAGCCAGG<br>TTCAGTGGCAGTGGGTCTGGGACAGAGTTCACTCTCA<br>CCATCAGCAGCCTGCAGTCTGAAGATTTTGCAGTTTAT<br>TACTGTCAGCAGCACCACGTCTGGCCTCTCACTTTTGG<br>CGGAGGGACCAAGGTTGAGATCAAACGGGCCGCTGC<br>CCTTGATAATGAAAAGTCAAACGGAACAATCATTCACG<br>TGAAGGGCAAGCACCTCTCCCCGTCACCCTTGTTCCCT<br>GGTCCATCCAAGCCATTCTGGGTGTTGGTCGTAGTGG<br>GTGGAGTCCTCGCTGTATACTCTCTGCTCGTCACCGTG<br>GCTTTTATAATCTTCTGGGTTAGATCCAAAAGAAGCCG<br>CCTGCTCCATAGCGATTACATGAATATGACTCCACGCC<br>GCCCTGGCCCCACAAGGAAACACTACCAGCCTTACGC<br>ACCACCTAGAGATTTCGCTGCCTATCGGAGCAGGGTG<br>AAGTTTTCCAGATCTGCAGATGCACCAGCGTATCAGCA<br>GGGCCAGAACCAACTGTATAACGAGCTCAACCTGGGA<br>CGCAGGGAAGAGTATGACGTTTTGGACAAGCGCAGA<br>GGACGGGACCCTGAGATGGGTGGCAAACCAAGACGA<br>AAAAACCCCCAGGAGGGTCTCTATAATGAGCTGCAGA<br>AGGATAAGATGGCTGAAGCCTATTCTGAAATAGGCAT<br>GAAAGGAGAGCGGAGAAGGGGAAAAGGGCACGACG<br>GTTTGTACCAGGGACTCAGCACTGCTACGAAGGATAC<br>TTATGACGCTCTCCACATGCAAGCCCTGCCACCTAGGT<br>AG |
| SEQ ID NO: 42 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I<br>V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y |

TABLE C-continued

| SEQ ID NO | SEQUENCE |
|---|---|
| | C Q Q H H V W P L T F G G G T K V E I K R A A A L D N E K S N G T I I H V K G K H L S P S P L F P G P S K P F W V L V V V G G V L A V Y S L L V T V A F I I F W V R S K R S R L L H S D Y M N M T P R R P G P T R K H Y Q P Y A P P R D F A A Y R S R V K F S R S A D A P A Y Q Q G Q N Q L Y N E L N L G R R E E Y D V L D K R R G R D P E M G G K P R R K N P Q E G L Y N E L Q K D K M A E A Y S E I G M K G E R R R G K H D G L Y Q G L S T A T K D T Y D A L H M Q A L P P R |
| SEQ ID NO: 43 | ATGGCACTCCCCGTAACTGCTCTGCTGCTGCCGTTGGC ATTGCTCCTGCACGCCGCACGCCCGCAGGTGCAGCTG GTGGAGTCTGGGGGAGGCGTGGTCCAGCCTGGGAGG TCCCTGAGACTCTCCTGTGCAGCGTCTGGATTCACCTT CAGTAGCTATGGCATGCACTGGGTCCGCCAGGCTCCA GGCAAGGGGCTGGAGTGGGTGGCAGTTATATCGTAT GATGGAAGTAATAAATACTATGCAGACTCCGTGAAGG GCCGATTCACCATCTCCAGAGACAATTCCAAGAACACG CTGTATCTGCAAATGAACAGCCTGAGAGCCGAGGACA CGGCCGGTGTACTACTGCGTCAAGGGGCCGTTGCAGGA GCCGCCATACGATTATGGAATGGACGTATGGGGCCAG GGAACAACTGTCACCGTCTCCTCAGGGTCTACATCCGG CTCCGGGAAGCCCGGAAGTGGCGAAGGTAGTACAAA GGGGGAAATAGTGATGACGCAGTCTCCAGCCACCCTG TCTGTGTCTCCAGGGGAAAGAGCCACCCTCTCCTGCAG GGCCAGTCAGAGTGTTAGCAGCAACTTAGCCTGGTAC CAGCAGAAACCTGGCCAGGCTCCCAGGCTCCTCATCTA TAGCGCATCCACCAGGGCCACTGGTATCCCAGCCAGG TTCAGTGGCAGTGGGTCTGGGACAGAGTTCACTCTCA CCATCAGCAGCCTGCAGTCTGAAGATTTTGCAGTTTAT TACTGTCAGCAGCACCACGTCTGGCCTCTCACTTTTGG CGGAGGGACCAAGGTTGAGATCAAACGGGCCGCTGC CCTTGATAATGAAAAGTCAAACGGAACAATCATTCACG TGAAGGGCAAGCACCTCAACGGGTCAGCCTTGTTCCC TGGTCCATCCAAGCCATTCTGGGTGTTGGTCGTAGTGG GTGGAGTCCTCGCTGTATACTCTCTGCTCGTCACCGTG GCTTTTATAATCTTCTGGGTTAGATCAAAAGAAGCCG CCTGCTCCATAGCGATTACATGAATATGACTCCACGCC GCCCTGGCCCCACAAGGAAACACTACCAGCCTTACGC ACCACCTAGAGATTTCGCTGCCTATCGGAGCAGGGTG AAGTTTTCCAGATCTGCAGATGCACCAGCGTATCAGCA GGGCCAGAACCAACTGTATAACGAGCTCAACCTGGGA CGCAGGGAAGAGTATGACGTTTTGGACAAGCGCAGA GGACGGGACCCTGAGATGGGTGGCAAACCAAGACGA AAAAACCCCCAGGAGGGTCTCTATAATGAGCTGCAGA AGGATAAGATGGCTGAAGCCTATTCTGAAATAGGCAT GAAAGGAGAGCGGAGAAGGGGAAAAGGGCACGACG GTTTGTACCAGGGACTCAGCACTGCTACGAAGGATAC TTATGACGCTCTCCACATGCAAGCCCTGCCACCTAGGT AG |
| SEQ ID NO: 44 | M A L P V T A L L L P L A L L L H A A R P Q V Q L V E S G G G V V Q P G R S L R L S C A A S G F T F S S Y G M H W V R Q A P G K G L E W V A V I S Y D G S N K Y Y A D S V K G R F T I S R D N S K N T L Y L Q M N S L R A E D T A V Y Y C V K G P L Q E P P Y D Y G M D V W G Q G T T V T V S S G S T S G S G K P G S G E G S T K G E I V M T Q S P A T L S V S P G E R A T L S C R A S Q S V S S N L A W Y Q Q K P G Q A P R L L I Y S A S T R A T G I P A R F S G S G S G T E F T L T I S S L Q S E D F A V Y Y C Q Q H H V W P L T F G G G T K V E I K R A A A L D N E K S N G T I I H V K G K H L N G S A L F P G P S K P F W V L V V V G G V L A V Y S L L V T V A F I I F W V R S K R S R L L H S D Y M N M T P R R P G P T R K H Y Q P Y A P P R D F A A Y R S R V K F S R S A D A P A Y Q Q G Q N Q L Y N E L N L G R R E E Y D V L D K R R G R D P E M G G K P R R K N P Q E G L Y N E L Q K D K M A E A Y S E I G M K G E R R R G K H D G L Y Q G L S T A T K D T Y D A L H M Q A L P P R |
| SEQ ID NO: 45 | ATGGCACTCCCCGTAACTGCTCTGCTGCTGCCGTTGGC ATTGCTCCTGCACGCCGCACGCCCGCAGGTGCAGCTG GTGGAGTCTGGGGGAGGCGTGGTCCAGCCTGGGAGG TCCCTGAGACTCTCCTGTGCAGCGTCTGGATTCACCTT CAGTAGCTATGGCATGCACTGGGTCCGCCAGGCTCCA GGCAAGGGGCTGGAGTGGGTGGCAGTTATATCGTAT GATGGAAGTAATAAATACTATGCAGACTCCGTGAAGG GCCGATTCACCATCTCCAGAGACAATTCCAAGAACACG |

TABLE C-continued

| SEQ ID NO | SEQUENCE |
| --- | --- |
| | CTGTATCTGCAAATGAACAGCCTGAGAGCCGAGGACA |
| | CGGCGGTGTACTACTGCGTCAAGGGGCCGTTGCAGGA |
| | GCCGCCATACGATTATGGAATGGACGTATGGGGCCAG |
| | GGAACAACTGTCACCGTCTCCTCAGGGTCTACATCCGG |
| | CTCCGGGAAGCCCGGAAGTGGCGAAGGTAGTACAAA |
| | GGGGGAAATAGTGATGACGCAGTCTCCAGCCACCCTG |
| | TCTGTGTCTCCAGGGGAAAGAGCCACCCTCTCCTGCAG |
| | GGCCAGTCAGAGTGTTAGCAGCAACTTAGCCTGGTAC |
| | CAGCAGAAACCTGGCCAGGCTCCCAGGCTCCTCATCTA |
| | TAGCGCATCCACCAGGGCCACTGGTATCCCAGCCAGG |
| | TTCAGTGGCAGTGGGTCTGGGACAGAGTTCACTCTCA |
| | CCATCAGCAGCCTGCAGTCTGAAGATTTTGCAGTTTAT |
| | TACTGTCAGCAGCACCACGTCTGGCCTCTCACTTTTGG |
| | CGGAGGGACCAAGGTTGAGATCAAACGGGCCGCTGC |
| | CCTTGATAATGAAAAGTCAAACGGAACAATCATTCACG |
| | TGAAGGGCAAGCACCTCTCCCCGTCACCCTTGTTCCCT |
| | GGTCCATCCAAGCCAGAAATCACACTGATCATATTTGG |
| | TGTAATTGCTGGCGTCATAGGGACCATTCTTTTGATCA |
| | GTTACGGAATTAGATCCAAAAGAAGCCGCCTGCTCCAT |
| | AGCGATTACATGAATATGACTCCACGCCGCCCTGGCCC |
| | CACAAGGAAACACTACCAGCCTTACGCACCACCTAGA |
| | GATTTCGCTGCCTATCGGAGCAGGGTGAAGTTTTCCA |
| | GATCTGCAGATGCACCAGCGTATCAGCAGGGCCAGAA |
| | CCAACTGTATAACGAGCTCAACCTGGGACGCAGGGAA |
| | GAGTATGACGTTTTGGACAAGCGCAGAGGACGGGAC |
| | CCTGAGATGGGTGGCAAACCAAGACGAAAAAACCCCC |
| | AGGAGGGTCTCTATAATGAGCTGCAGAAGGATAAGAT |
| | GGCTGAAGCCTATTCTGAAATAGGCATGAAAGGAGAG |
| | CGGAGAAGGGGAAAAGGGCACGACGGTTTGTACCAG |
| | GGACTCAGCACTGCTACGAAGGATACTTATGACGCTCT |
| | CCACATGCAAGCCCTGCCACCTAGGTAG |
| SEQ ID NO: 46 | M A L P V T A L L L P L A L L L H A A R P Q V Q L V E S |
| | G G G V V Q P G R S L R L S C A A S G F T F S S Y G M |
| | H W V R Q A P G K G L E W V A V I S Y D G S N K Y Y A |
| | D S V K G R F T I S R D N S K N T L Y L Q M N S L R A E |
| | D T A V Y Y C V K G P L Q E P P Y D Y G M D V W G Q |
| | G T T V T V S S G S T S G S G K P G S G E G S T K G E I |
| | V M T Q S P A T L S V S P G E R A T L S C R A S Q S V S |
| | S N L A W Y Q Q K P G Q A P R L L I Y S A S T R A T G I |
| | P A R F S G S G S G T E F T L T I S S L Q S E D F A V Y Y |
| | C Q Q H H V W P L T F G G G T K V E I K R A A A L D N |
| | E K S N G T I I H V K G K H L S P S P L F P G P S K P E I |
| | T L I I F G V I A G V I G T I L L I S Y G I R S K R S R L L H |
| | S D Y M N M T P R R P G P T R K H Y Q P Y A P P R D F |
| | A A Y R S R V K F S R S A D A P A Y Q Q G Q N Q L Y N |
| | E L N L G R R E E Y D V L D K R R G R D P E M G G K P |
| | R R K N P Q E G L Y N E L Q K D K M A E A Y S E I G M |
| | K G E R R R G K G H D G L Y Q G L S T A T K D T Y D A |
| | L H M Q A L P P R |
| SEQ ID NO: 47 | ATGGCACTCCCCGTAACTGCTCTGCTGCTGCCGTTGGC |
| | ATTGCTCCTGCACGCCGCACGCCCGCAGGTGCAGCTG |
| | GTGGAGTCTGGGGGAGGCGTGGTCCAGCCTGGGAGG |
| | TCCCTGAGACTCTCCTGTGCAGCGTCTGGATTCACCTT |
| | CAGTAGCTATGGCATGCACTGGGTCCGCCAGGCTCCA |
| | GGCAAGGGGCTGGAGTGGGTGGCAGTTATATCGTAT |
| | GATGGAAGTAATAAATACTATGCAGACTCCGTGAAGG |
| | GCCGATTCACCATCTCCAGAGACAATTCCAAGAACACG |
| | CTGTATCTGCAAATGAACAGCCTGAGAGCCGAGGACA |
| | CGGCGGTGTACTACTGCGTCAAGGGGCCGTTGCAGGA |
| | GCCGCCATACGATTATGGAATGGACGTATGGGGCCAG |
| | GGAACAACTGTCACCGTCTCCTCAGGGTCTACATCCGG |
| | CTCCGGGAAGCCCGGAAGTGGCGAAGGTAGTACAAA |
| | GGGGGAAATAGTGATGACGCAGTCTCCAGCCACCCTG |
| | TCTGTGTCTCCAGGGGAAAGAGCCACCCTCTCCTGCAG |
| | GGCCAGTCAGAGTGTTAGCAGCAACTTAGCCTGGTAC |
| | CAGCAGAAACCTGGCCAGGCTCCCAGGCTCCTCATCTA |
| | TAGCGCATCCACCAGGGCCACTGGTATCCCAGCCAGG |
| | TTCAGTGGCAGTGGGTCTGGGACAGAGTTCACTCTCA |
| | CCATCAGCAGCCTGCAGTCTGAAGATTTTGCAGTTTAT |
| | TACTGTCAGCAGCACCACGTCTGGCCTCTCACTTTTGG |
| | CGGAGGGACCAAGGTTGAGATCAAACGGGCCGCTGC |
| | CCTTGATAATGAAAAGTCAAACGGAACAATCATTCACG |
| | TGAAGGGCAAGCACCTCTCCCCGTCACCCTTGTTCCCT |
| | GGTCCATCCAAGCCAGAAATCACACTGATCATATTTGG |
| | TGTAATTGCTATAGTCATAGGGACCATTCTTTTGATCA |
| | GTTACGGAATTAGATCCAAAAGAAGCCGCCTGCTCCAT |

TABLE C-continued

| SEQ ID NO | SEQUENCE |
|---|---|
| | AGCGATTACATGAATATGACTCCACGCCGCCCTGGCCC<br>CACAAGGAAACACTACCAGCCTTACGCACCACCTAGA<br>GATTTCGCTGCCTATCGGAGCAGGGTGAAGTTTTCCA<br>GATCTGCAGATGCACCAGCGTATCAGCAGGGCCAGAA<br>CCAACTGTATAACGAGCTCAACCTGGGACGCAGGGAA<br>GAGTATGACGTTTTGGACAAGCGCAGAGGACGGGAC<br>CCTGAGATGGGTGGCAAACCAAGACGAAAAAACCCCC<br>AGGAGGGTCTCTATAATGAGCTGCAGAAGGATAAGAT<br>GGCTGAAGCCTATTCTGAAATAGGCATGAAAGGAGAG<br>CGGAGAAGGGGAAAAGGGCACGACGGTTTGTACCAG<br>GGACTCAGCACTGCTACGAAGGATACTTATGACGCTCT<br>CCACATGCAAGCCCTGCCACCTAGGTAG |
| SEQ ID NO: 48 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I<br>V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y<br>C Q Q H H V W P L T F G G G T K V E I K R A A A L D N<br>E K S N G T I I H V K G K H L S P S P L F P G P S K P E I<br>T L I I F G V M A I V I G T I L L I S Y G I R S K R S R L L H<br>S D Y M N M T P R R P G P T R K H Y Q P Y A P P R D F<br>A A Y R S R V K F S R S A D A P A Y Q Q G Q N Q L Y N<br>E L N L G R R E E Y D V L D K R R G R D P E M G G K P<br>R R K N P Q E G L Y N E L Q K D K M A E A Y S E I G M<br>K G E R R R G K G H D G L Y Q G L S T A T K D T Y D A<br>L H M Q A L P P R |
| SEQ ID NO: 49 | ATGGCACTCCCCGTAACTGCTCTGCTGCTGCCGTTGGC<br>ATTGCTCCTGCACGCCGCACGCCCGCAGGTGCAGCTG<br>GTGGAGTCTGGGGGAGGCGTGGTCCAGCCTGGGAGG<br>TCCCTGAGACTCTCCTGTGCAGCGTCTGGATTCACCTT<br>CAGTAGCTATGGCATGCACTGGGTCCGCCAGGCTCCA<br>GGCAAGGGGCTGGAGTGGGTGGCAGTTATATCGTAT<br>GATGGAAGTAATAAATACTATGCAGACTCCGTGAAGG<br>GCCGATTCACCATCTCCAGAGACAATTCCAAGAACACG<br>CTGTATCTGCAAATGAACAGCCTGAGAGCCGAGGACA<br>CGGCCGTGTACTACTGCGTCAAGGGGCCGTTGCAGGA<br>GCCGCCATACGATTATGGAATGGACGTATGGGGCCAG<br>GGAACAACTGTCACCGTCTCCTCAGGGTCTACATCCGG<br>CTCCGGGAAGCCCGGAAGTGGCGAAGGTAGTACAAA<br>GGGGGAAATAGTGATGACGCAGTCTCCAGCCACCCTG<br>TCTGTGTCTCCAGGGGAAAGAGCCACCCTCTCCTGCAG<br>GGCCAGTCAGAGTGTTAGCAGCAACTTAGCCTGGTAC<br>CAGCAGAAACCTGGCCAGGCTCCCAGGCTCCTCATCTA<br>TAGCGCATCCACCAGGGCCACTGGTATCCCAGCCAGG<br>TTCAGTGGCAGTGGGTCTGGGACAGAGTTCACTCTCA<br>CCATCAGCAGCCTGCAGTCTGAAGATTTTGCAGTTTAT<br>TACTGTCAGCAGCACCACGTCTGGCCTCTCACTTTTGG<br>CGGAGGGACCAAGGTTGAGATCAAACGGGCCGCTGC<br>CCTTGATAATGAAAAGTCAAACGGAACAATCATTCACG<br>TGAAGGGCAAGCACCTCTCCCCGTCACCCTTGTTCCCT<br>GGTCCATCCAAGCCACTTACGAGCATAATCTCTGCCGT<br>TGTAGGCATACTTCTGGTGGTTGTGCTTGGAGTTGTAT<br>TCGGTATCCTTATAAAAAGATCCAAAAGAAGCCGCCTG<br>CTCCATAGCGATTACATGAATATGACTCCACGCCGCCC<br>TGGCCCCACAAGGAAACACTACCAGCCTTACGCACCAC<br>CTAGAGATTTCGCTGCCTATCGGAGCAGGGTGAAGTT<br>TTCCAGATCTGCAGATGCACCAGCGTATCAGCAGGGC<br>CAGAACCAACTGTATAACGAGCTCAACCTGGGACGCA<br>GGGAAGAGTATGACGTTTTGGACAAGCGCAGAGGAC<br>GGGACCCTGAGATGGGTGGCAAACCAAGACGAAAAA<br>ACCCCCAGGAGGGTCTCTATAATGAGCTGCAGAAGGA<br>TAAGATGGCTGAAGCCTATTCTGAAATAGGCATGAAA<br>GGAGAGCGGAGAAGGGGAAAAGGGCACGACGGTTT<br>GTACCAGGGACTCAGCACTGCTACGAAGGATACTTAT<br>GACGCTCTCCACATGCAAGCCCTGCCACCTAGGTAG |
| SEQ ID NO: 50 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I |

TABLE C-continued

| SEQ ID NO | SEQUENCE |
|---|---|
|  | V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y<br>C Q Q H H V W P L T F G G G T K V E I K R A A A L D N<br>E K S N G T I I H V K G K H L S P S P L F P G P S K P L T<br>S I I S A V V G I L L V V V L G V V F G I L I K R S K R S R<br>L L H S D Y M N M T P R R P G P T R K H Y Q P Y A P P<br>R D F A A Y R S R V K F S R S A D A P A Y Q Q G Q N Q<br>L Y N E L N L G R R E E Y D V L D K R R G R D P E M G<br>G K P R R K N P Q E G L Y N E L Q K D K M A E A Y S E<br>I G M K G E R R R G K G H D G L Y Q G L S T A T K D T<br>Y D A L H M Q A L P P R |
| SEQ ID NO: 51 | ATGGCACTCCCCGTAACTGCTCTGCTGCTGCCGTTGGC<br>ATTGCTCCTGCACGCCGCACGCCCGCAGGTGCAGCTG<br>GTGGAGTCTGGGGGAGGCGTGGTCCAGCCTGGGAGG<br>TCCCTGAGACTCTCCTGTGCAGCGTCTGGATTCACCTT<br>CAGTAGCTATGGCATGCACTGGGTCCGCCAGGCTCCA<br>GGCAAGGGGCTGGAGTGGGTGGCAGTTATATCGTAT<br>GATGGAAGTAATAAATACTATGCAGACTCCGTGAAGG<br>GCCGATTCACCATCTCCAGAGACAATTCCAAGAACACG<br>CTGTATCTGCAAATGAACAGCCTGAGAGCCGAGGACA<br>CGGCGGTGTACTACTGCGTCAAGGGGCCGTTGCAGGA<br>GCCGCCATACGATTATGGAATGGACGTATGGGGCCAG<br>GGAACAACTGTCACCGTCTCCTCAGGGTCTACATCCGG<br>CTCCGGGAAGCCCGGAAGTGGCGAAGGTAGTACAAA<br>GGGGGAAATAGTGATGACGCAGTCTCCAGCCACCCTG<br>TCTGTGTCTCCAGGGGAAAGAGCCACCCTCTCCTGCAG<br>GGCCAGTCAGAGTGTTAGCAGCAACTTAGCCTGGTAC<br>CAGCAGAAACCTGGCCAGGCTCCCAGGCTCCTCATCTA<br>TAGCGCATCCACCAGGGCCACTGGTATCCCAGCCAGG<br>TTCAGTGGCAGTGGGTCTGGGACAGAGTTCACTCTCA<br>CCATCAGCAGCCTGCAGTCTGAAGATTTTGCAGTTTAT<br>TACTGTCAGCAGCACCACGTCTGGCCTCTCACTTTTGG<br>CGGAGGGACCAAGGTTGAGATCAAACGGGCCGCTGC<br>CCTTGATAATGAAAAGTCAAACGGAACAATCATTCACG<br>TGAAGGGCAAGCACCTCTCCCCGTCACCCTTGTTCCCT<br>GGTCCATCCAAGCCACTTACGAGCATAATCTCTGCCGT<br>TGTAGTGATACTTCTGGTGGTTGTGCTTGGAGTTGTAT<br>TCGTTATCCTTATAAAAAGATCCAAAAGAAGCCGCCTG<br>CTCCATAGCGATTACATGAATATGACTCCACGCCGCCC<br>TGGCCCCACAAGGAAACACTACCAGCCTTACGCACCAC<br>CTAGAGATTTCGCTGCCTATCGGAGCAGGGTGAAGTT<br>TTCCAGATCTGCAGATGCACCAGCGTATCAGCAGGGC<br>CAGAACCAACTGTATAACGAGCTCAACCTGGGACGCA<br>GGGAAGAGTATGACGTTTTGGACAAGCGCAGAGGAC<br>GGGACCCTGAGATGGGTGGCAAACCAAGACGAAAAA<br>ACCCCCAGGAGGGTCTCTATAATGAGCTGCAGAAGGA<br>TAAGATGGCTGAAGCCTATTCTGAAATAGGCATGAAA<br>GGAGAGCGGAGAAGGGGAAAAGGGCACGACGGTTTT<br>GTACCAGGGACTCAGCACTGCTACGAAGGATACTTAT<br>GACGCTCTCCACATGCAAGCCCTGCCACCTAGGTAG |
| SEQ ID NO: 52 | M A L P V T A L L L P L A L L L H A A R P Q V Q L V E S<br>G G G V V Q P G R S L R L S C A A S G F T F S S Y G M<br>H W V R Q A P G K G L E W V A V I S Y D G S N K Y Y A<br>D S V K G R F T I S R D N S K N T L Y L Q M N S L R A E<br>D T A V Y Y C V K G P L Q E P P Y D Y G M D V W G Q<br>G T T V T V S S G S T S G S G K P G S G E G S T K G E I<br>V M T Q S P A T L S V S P G E R A T L S C R A S Q S V S<br>S N L A W Y Q Q K P G Q A P R L L I Y S A S T R A T G I<br>P A R F S G S G S G T E F T L T I S S L Q S E D F A V Y Y<br>C Q Q H H V W P L T F G G G T K V E I K R A A A L D N<br>E K S N G T I I H V K G K H L S P S P L F P G P S K P L T<br>S I I S A V V V I L L V V V L G V V F V I L I K R S K R S R<br>L L H S D Y M N M T P R R P G P T R K H Y Q P Y A P P<br>R D F A A Y R S R V K F S R S A D A P A Y Q Q G Q N Q<br>L Y N E L N L G R R E E Y D V L D K R R G R D P E M G<br>G K P R R K N P Q E G L Y N E L Q K D K M A E A Y S E<br>I G M K G E R R R G K G H D G L Y Q G L S T A T K D T<br>Y D A L H M Q A L P P R |
| SEQ ID NO: 53 | GCTGCAGCATTGAGCAACTCAATAATGTATTTTAGTCA<br>CTTTTGTACCAGTGTTCTTGCCGGCTAAGCCTACTACCA<br>CACCCGCTCCACGGCCACCTACCCCAGCTCCTACCATC<br>GCTTCACAGCCTCTGTCCCTGCGCCCAGAGGCTTGCCG<br>ACCGGCCGCAGGGGCGCTGTTCATACCAGAGGACTG<br>GATTTCGCCTGCGATATCTATATCTGGGCACCCCTGGC |

TABLE C-continued

| SEQ ID NO | SEQUENCE |
|---|---|
|  | CGGAACCTGCGGCGTACTCCTGCTGTCCCTGGTCATCA CGCTCTATTGTAATCACAGGAAC. |
| SEQ ID NO: 54 | A A A L S N S I M Y F S H F V P V F L P A K P T T T P A P R P P T P A P T I A S Q P L S L R P E A C R P A A G G A V H T R G L D F A C D I Y I W A P L A G T C G V L L L S L V I T L Y C N H R N |

SEQUENCE LISTING

<160> NUMBER OF SEQ ID NOS: 68

<210> SEQ ID NO 1
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 1

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
```

```
            275                 280                 285
Lys His Leu Cys Pro Ser Pro Leu Phe Pro Gly Pro Ser Lys Pro Phe
290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                    325                 330                 335

Leu Leu His Ser Asp Tyr Met Asn Met Thr Pro Arg Arg Pro Gly Pro
                340                 345                 350

Thr Arg Lys His Tyr Gln Pro Tyr Ala Pro Pro Arg Asp Phe Ala Ala
                355                 360                 365

Tyr Arg Ser Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
                435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 2
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 2

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
                35                  40                  45

Arg Glu Phe Arg Ala Ser Leu His Lys Gly Leu Asp Ser Ala Val Glu
50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
                115                 120                 125

Asn Gly Thr Ile Ile His Val Lys Gly Lys His Leu Cys Pro Ser Pro
                130                 135                 140

Leu Phe Pro Gly Pro Ser Lys Pro Phe Trp Val Leu Val Val Val Gly
145                 150                 155                 160
```

```
Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
    210                 215                 220

<210> SEQ ID NO 3
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 3

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
            85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Gln Gly Ala Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
    210                 215                 220

<210> SEQ ID NO 4
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 4

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
```

```
            20                  25                  30
Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Gln Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 5
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 5

Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Ala Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
```

165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
        210                 215                 220

<210> SEQ ID NO 6
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 6

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Ser Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 7
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 7

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

-continued

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                    85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
                115                 120                 125

Asn Gly Thr Ile Ile His Val Lys Gly Lys His Leu Ser Pro Ser Pro
        130                 135                 140

Leu Phe Pro Gly Pro Ser Lys Pro Phe Trp Val Leu Val Val Val Gly
145                 150                 155                 160

Gly Val Leu Ala Ala Tyr Ser Leu Leu Val Thr Val Ala Phe Ile Ile
                    165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
                195                 200                 205

Tyr Ala Pro Pro Arg Asp Phe Ala Ala Tyr Arg Ser
        210                 215                 220

<210> SEQ ID NO 8
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 8

Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
 50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                    85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
                115                 120                 125

Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Ala Tyr Ser Leu Leu Val Thr Val Ala Phe Ile Ile
                    165                 170                 175

```
              Phe Trp Val Arg Ser Lys Arg Ser Arg Leu Leu His Ser Asp Tyr Met
                          180                 185                 190

Asn Met Thr Pro Arg Arg Pro Gly Pro Thr Arg Lys His Tyr Gln Pro
                      195                 200                 205

Tyr Ala Pro Pro Arg Asp Phe Ala Ala Tyr Arg Ser
                  210                 215                 220

<210> SEQ ID NO 9
<211> LENGTH: 220
<212> TYPE: PRT
<213> ORGANISM: Artificial Sequence
<220> FEATURE:
<223> OTHER INFORMATION: POLYPEPTIDE

<400> SEQUENCE: 9

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Val Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 10
<211> LENGTH: 747
<212> TYPE: DNA
<213> ORGANISM: Artificial Sequence
<220> FEATURE:
<223> OTHER INFORMATION: POLYPEPTIDE

<400> SEQUENCE: 10
caggtgcagc tggtggagtc tgggggaggc gtggtccagc ctggaggtc cctgagactc      60 tcctgtgcag cgtctggatt caccttcagt agctatggca tgcactgggt ccgccaggct     120
ccaggcaagg ggctggagtg ggtggcagtt atatcgtatg atggaagtaa taaatactat     180
gcagactccg tgaagggccg attcaccatc tccagagaca attccaagaa cacgctgtat     240
```

-continued

```
ctgcaaatga acagcctgag agccgaggac acggcggtgt actactgcgt caagggccgc    300
ttgcaggagc cgccatacga ttatggaatg gacgtatggg gccagggaac aactgtcacc    360
gtctcctcag gtctacatc cggctccggg aagcccggaa gtggcgaagg tagtacaaag    420
ggggaaatag tgatgacgca gtctccagcc accctgtctg tgtctccagg ggaaagagcc    480 acccctctcct gcagggccag tcagagtgtt agcagcaact tagcctggta ccagcagaaa    540
cctggccagg ctcccaggct cctcatctat agcgcatcca ccagggccac tggtatccca    600
gccaggttca gtggcagtgg gtctgggaca gagttcactc tcaccatcag cagcctgcag    660
tctgaagatt ttgcagttta ttactgtcag cagcaccacg tctggcctct cactttggc    720 ggagggacca aggttgagat caaacgg                                        747
```

<210> SEQ ID NO 11
<211> LENGTH: 249
<212> TYPE: PRT
<213> ORGANISM: Artificial Sequence
<220> FEATURE:
<223> OTHER INFORMATION: POLYPEPTIDE

<400> SEQUENCE: 11

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

Trp Gly Gln Gly Thr Thr Val Thr Val Ser Ser Gly Ser Thr Ser Gly
        115                 120                 125

Ser Gly Lys Pro Gly Ser Gly Glu Gly Ser Thr Lys Gly Glu Ile Val
    130                 135                 140

Met Thr Gln Ser Pro Ala Thr Leu Ser Val Ser Pro Gly Glu Arg Ala
145                 150                 155                 160

Thr Leu Ser Cys Arg Ala Ser Gln Ser Val Ser Ser Asn Leu Ala Trp
                165                 170                 175

Tyr Gln Gln Lys Pro Gly Gln Ala Pro Arg Leu Leu Ile Tyr Ser Ala
            180                 185                 190

Ser Thr Arg Ala Thr Gly Ile Pro Ala Arg Phe Ser Gly Ser Gly Ser
        195                 200                 205

Gly Thr Glu Phe Thr Leu Thr Ile Ser Ser Leu Gln Ser Glu Asp Phe
    210                 215                 220

Ala Val Tyr Tyr Cys Gln Gln His His Val Trp Pro Leu Thr Phe Gly
225                 230                 235                 240

Gly Gly Thr Lys Val Glu Ile Lys Arg
                245
```

<210> SEQ ID NO 12
<211> LENGTH: 107

<212> TYPE: PRT
<213> ORGANISM: Artificial Sequence
<220> FEATURE:
<223> OTHER INFORMATION: POLYPEPTIDE

<400> SEQUENCE: 12

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys
            100                 105

<210> SEQ ID NO 13
<211> LENGTH: 123
<212> TYPE: PRT
<213> ORGANISM: Artificial Sequence
<220> FEATURE:
<223> OTHER INFORMATION: POLYPEPTIDE

<400> SEQUENCE: 13

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

Trp Gly Gln Gly Thr Thr Val Thr Val Ser Ser
        115                 120

<210> SEQ ID NO 14
<211> LENGTH: 11
<212> TYPE: PRT
<213> ORGANISM: Artificial Sequence
<220> FEATURE:
<223> OTHER INFORMATION: POLYPEPTIDE

<400> SEQUENCE: 14

Arg Ala Ser Gln Ser Val Ser Ser Asn Leu Ala
1               5                   10

<210> SEQ ID NO 15
<211> LENGTH: 7
<212> TYPE: PRT

```
<213> ORGANISM: Artificial Sequence
<220> FEATURE:
<223> OTHER INFORMATION: POLYPEPTIDE

<400> SEQUENCE: 15

Ser Ala Ser Thr Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: POLYPEPTIDE

<400> SEQUENCE: 16

Gln Gln His His Val Trp Pro Leu Thr
1               5

<210> SEQ ID NO 17
<211> LENGTH: 5
<212> TYPE: PRT
<213> ORGANISM: Artificial Sequence
<220> FEATURE:
<223> OTHER INFORMATION: POLYPEPTIDE

<400> SEQUENCE: 17

Ser Tyr Gly Met His
1               5

<210> SEQ ID NO 18
<211> LENGTH: 17
<212> TYPE: PRT
<213> ORGANISM: Artificial Sequence
<220> FEATURE:
<223> OTHER INFORMATION: POLYPEPTIDE

<400> SEQUENCE: 18

Val Ile Ser Tyr Asp Gly Ser Asn Lys Tyr Tyr Ala Asp Ser Val Lys
1               5                   10                  15

Gly

<210> SEQ ID NO 19
<211> LENGTH: 14
<212> TYPE: PRT
<213> ORGANISM: Artificial Sequence
<220> FEATURE:
<223> OTHER INFORMATION: POLYPEPTIDE

<400> SEQUENCE: 19

Gly Pro Leu Gln Glu Pro Pro Tyr Asp Tyr Gly Met Asp Val
1               5                   10

<210> SEQ ID NO 20
<211> LENGTH: 7
<212> TYPE: PRT
<213> ORGANISM: Artificial Sequence
<220> FEATURE:
<223> OTHER INFORMATION: POLYPEPTIDE

<400> SEQUENCE: 20

Gly Phe Thr Phe Ser Ser Tyr
1               5

<210> SEQ ID NO 21
<211> LENGTH: 6
```

```
<212> TYPE: PRT
<213> ORGANISM: Artificial Sequence
<220> FEATURE:
<223> OTHER INFORMATION: POLYPEPTIDE

<400> SEQUENCE: 21

Ser Tyr Asp Gly Ser Asn
1               5

<210> SEQ ID NO 22
<211> LENGTH: 21
<212> TYPE: PRT
<213> ORGANISM: Artificial Sequence
<220> FEATURE:
<223> OTHER INFORMATION: POLYPEPTIDE

<400> SEQUENCE: 22

Met Ala Leu Pro Val Thr Ala Leu Leu Leu Pro Leu Ala Leu Leu Leu
1               5                   10                  15

His Ala Ala Arg Pro
            20

<210> SEQ ID NO 23
<211> LENGTH: 22
<212> TYPE: PRT
<213> ORGANISM: Artificial Sequence
<220> FEATURE:
<223> OTHER INFORMATION: POLYPEPTIDE

<400> SEQUENCE: 23

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 24
<211> LENGTH: 22
<212> TYPE: PRT
<213> ORGANISM: Artificial Sequence
<220> FEATURE:
<223> OTHER INFORMATION: POLYPEPTIDE

<400> SEQUENCE: 24

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 25
<211> LENGTH: 15
<212> TYPE: PRT
<213> ORGANISM: Artificial Sequence
<220> FEATURE:
<223> OTHER INFORMATION: POLYPEPTIDE

<400> SEQUENCE: 25

Gly Gly Gly Gly Ser Gly Gly Gly Ser Gly Gly Gly Gly Ser
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: POLYPEPTIDE
```

<400> SEQUENCE: 26

Gly Ser Thr Ser Gly Ser Gly Lys Pro Gly Ser Gly Glu Gly Ser Thr
1               5                   10                  15

Lys Gly

<210> SEQ ID NO 27
<211> LENGTH: 112
<212> TYPE: PRT
<213> ORGANISM: Artificial Sequence
<220> FEATURE:
<223> OTHER INFORMATION: POLYPEPTIDE

<400> SEQUENCE: 27

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 28
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 28
atggcactcc ccgtaactgc tctgctgctg ccgttggcat tgctcctgca cgccgcacgc     60
ccgcaggtgc agctggtgga gtctggggga ggcgtggtcc agcctgggag gtccctgaga    120
ctctcctgtg cagcgtctgg attcaccttc agtagctatg catgcactgg gtccgccag    180 gctccaggca aggggctgga gtgggtggca gttatatcgt atgatggaag taataaatac    240
tatgcagact ccgtgaaggg ccgattcacc atctccagag acaattccaa gaacacgctg    300
tatctgcaaa tgaacagcct gagagccgag gacacggcgg tgtactactg cgtcaagggg    360
ccgttgcagg agccgccata cgattatgga atggacgtat ggggccaggg aacaactgtc    420
accgtctcct cagggtctac atccggctcc gggaagcccg gaagtggcga aggtagtaca    480
aagggggaaa tagtgatgac gcagtctcca gccacccctgt ctgtgtctcc aggggaaaga    540
gccaccctct cctgcagggc cagtcagagt gttagcagca acttagcctg gtaccagcag    600
aaacctggcc aggctcccag gctcctcatc tatagcgcat ccaccagggc cactggtatc    660
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg ccgctgccc ttgataatga aaagtcaaac    840
ggaacaatca ttcacgtgaa gggcaagcac ctctgtccgt caccccttgtt ccctggtcca    900 tccaagccat tctgggtgtt ggtcgtagtg ggtggagtcc tcgcttgtta ctctctgctc    960

```
gtcaccgtgg cttttataat cttctgggtt agatccaaaa gaagccgcct gctccatagc    1020
gattacatga atatgactcc acgccgccct ggccccacaa ggaaacacta ccagccttac    1080
gcaccaccta gagatttcgc tgcctatcgg agcagggtga agttttccag atctgcagat    1140
gcaccagcgt atcagcaggg ccagaaccaa ctgtataacg agctcaacct gggacgcagg    1200
gaagagtatg acgttttgga caagcgcaga ggacgggacc ctgagatggg tggcaaacca    1260
agacgaaaaa accccagga gggtctctat aatgagctgc agaaggataa gatggctgaa    1320
gcctattctg aaataggcat gaaaggagag cggagaaggg gaaaagggca cgacggtttg    1380
taccagggac tcagcactgc tacgaaggat acttatgacg ctctccacat gcaagccctg    1440
ccacctaggt ag                                                        1452

<210> SEQ ID NO 29
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 29
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg gcatgcactg ggtccgccag     180
gctccaggca aggggctgga gtgggtggca gttatatcgt atgatggaag taataaatac     240
tatgcagact ccgtgaaggg ccgattcacc atctccagag acaattccaa gaacacgctg     300
tatctgcaaa tgaacagcct gagagccgag gacacggcgg tgtactactg cgtcaagggg     360
ccgttgcagg agccgccata cgattatgga atggacgtat ggggccaggg aacaactgtc     420
accgtctcct cagggtctac atccggctcc gggaagcccg aagtggcga aggtagtaca     480 aagggggaaa tagtgatgac gcagtctcca gccaccctgt ctgtgtctcc aggggaaaga     540
gccaccctct cctgcagggc cagtcagagt gttagcagca acttagcctg gtaccagcag     600
aaacctggcc aggctcccag gctcctcatc tatagcgcat ccaccagggc cactggtatc     660
ccagccaggt tcagtggcag tgggtctggg acagagttca ctctcaccat cagcagcctg     720
cagtctgaag attttgcagt ttattactgt cagcagcacc acgtctggcc tctcactttt     780
ggcggaggga ccaaggttga gatcaaacgg ccgctgccc ttgataatga aaagtcacag     840
ggaacaatca ttcacgtgaa gggcaagcac ctctgtccgt cacccttgtt ccctggtcca     900
tccaagccat tctgggtgtt ggtcgtagtg ggtggagtcc tgcttgtta ctctctgctc     960 gtcaccgtgg cttttataat cttctgggtt agatccaaaa gaagccgcct gctccatagc    1020
gattacatga atatgactcc acgccgccct ggccccacaa ggaaacacta ccagccttac    1080
gcaccaccta gagatttcgc tgcctatcgg agcagggtga agttttccag atctgcagat    1140
gcaccagcgt atcagcaggg ccagaaccaa ctgtataacg agctcaacct gggacgcagg    1200
gaagagtatg acgttttgga caagcgcaga ggacgggacc ctgagatggg tggcaaacca    1260
agacgaaaaa accccagga gggtctctat aatgagctgc agaaggataa gatggctgaa    1320
gcctattctg aaataggcat gaaaggagag cggagaaggg gaaaagggca cgacggtttg    1380
taccagggac tcagcactgc tacgaaggat acttatgacg ctctccacat gcaagccctg    1440
ccacctaggt ag                                                        1452
```

```
<210> SEQ ID NO 30
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 30

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Gln Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365
```

```
Tyr Arg Ser Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Gly Arg Asp Pro Glu Met
            405                 410                 415

Gly Gly Lys Pro Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 31
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 31
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg gcatgcactg ggtccgccag     180
gctccaggca aggggctgga gtgggtggca gttatatcgt atgatggaag taataaatac     240
tatgcagact ccgtgaaggg ccgattcacc atctccagag acaattccaa gaacacgctg     300
tatctgcaaa tgaacagcct gagagccgag gacacggcgg tgtactactg cgtcaagggg     360
ccgttgcagg agccgccata cgattatgga atggacgtat ggggccaggg aacaactgtc     420
accgtctcct cagggtctac atccggctcc gggaagcccg aagtggcga aggtagtaca     480
aagggggaaa tagtgatgac gcagtctcca gccaccctgt ctgtgtctcc aggggaaaga     540
gccaccctct cctgcagggc cagtcagagt gttagcagca acttagcctg gtaccagcag     600
aaacctggcc aggctcccag gctcctcatc tatagcgcat ccaccagggc cactggtatc     660
ccagccaggt tcagtggcag tgggtctggg acagagttca ctctcaccat cagcagcctg     720
cagtctgaag attttgcagt ttattactgt cagcagcacc acgtctggcc tctcactttt     780
ggcggaggga ccaaggttga gatcaaacgg ccgctgccc ttgataatga aaagtcaaac     840
ggagccatca ttcacgtgaa gggcaagcac ctctgtccgt cacccttgtt ccctggtcca     900
tccaagccat tctgggtgtt ggtcgtagtg ggtggagtcc tcgcttgtta ctctctgctc     960
gtcaccgtgg cttttataat cttctgggtt agatccaaaa gaagccgcct gctccatagc    1020
gattacatga atatgactcc acgccgccct ggccccacaa ggaaacacta ccagccttac    1080
gcaccaccta gagatttcgc tgcctatcgg agcagggtga gttttccag atctgcagat    1140
gcaccagcgt atcagcaggg ccagaaccaa ctgtataacg agctcaacct gggacgcagg    1200
gaagagtatg acgttttgga caagcgcaga ggacgggacc ctgagatggg tggcaaacca    1260
agacgaaaaa accccaggga gggtctctat aatgagctgc agaaggataa gatggctgaa    1320
gcctattctg aaataggcat gaaggagag cggagaaggg gaaaagggca cgacggtttg    1380
```
taccagggac tcagcactgc tacgaaggat acttatgacg ctctccacat gcaagccctg 1440
ccacctaggt ag 1452

<210> SEQ ID NO 32
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 32

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Ala Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

```
Thr Arg Lys His Tyr Gln Pro Tyr Ala Pro Pro Arg Asp Phe Ala Ala
        355                 360                 365
Tyr Arg Ser Arg Val Lys Phe Ser Arg Ser Ala Asp Ala Pro Ala Tyr
    370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Gly Arg Asp Pro Glu Met
                405                 410                 415
Gly Gly Lys Pro Arg Arg Lys Asn Pro Gln Glu Gly Leu Tyr Asn Glu
            420                 425                 430
Leu Gln Lys Asp Lys Met Ala Glu Ala Tyr Ser Glu Ile Gly Met Lys
        435                 440                 445
Gly Glu Arg Arg Arg Gly Lys Gly His Asp Gly Leu Tyr Gln Gly Leu
    450                 455                 460
Ser Thr Ala Thr Lys Asp Thr Tyr Asp Ala Leu His Met Gln Ala Leu
465                 470                 475                 480
Pro Pro Arg
```

<210> SEQ ID NO 33
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 33

```
atggcactcc ccgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc agtagctatg catgcactgg gtccgccag    180
gctccaggca aggggctgga gtgggtggca gttatatcgt atgatggaag taataaatac   240
tatgcagact ccgtgaaggg ccgattcacc atctccagag acaattccaa gaacacgctg   300
tatctgcaaa tgaacagcct gagagccgag gacacggcgg tgtactactg cgtcaagggg   360
ccgttgcagg agccgccata cgattatgga atggacgtat ggggccaggg aacaactgtc   420
accgtctcct cagggtctac atccggctcc gggaagcccg aagtggcga aggtagtaca   480
aagggggaaa tagtgatgac gcagtctcca gccaccctgt ctgtgtctcc aggggaaaga   540
gccaccctct cctgcagggc cagtcagagt gttagcagca acttagcctg gtaccagcag   600
aaacctggcc aggctcccag gctcctcatc tatagcgcat ccaccagggc cactggtatc   660
ccagccaggt tcagtggcag tgggtctggg acagagttca ctctcaccat cagcagcctg   720
cagtctgaag attttgcagt ttattactgt cagcagcacc acgtctggcc tctcactttt   780
ggcggaggga ccaaggttga gatcaaacgg accgctgccc ttgataatga aaagtcaaac   840
ggaacaatca ttcacgtgaa gggcaagcac ctctccccgt cacccttgtt ccctggtcca   900
tccaagccat tctgggtgtt ggtcgtagtg ggtggagtcc tcgcttgtta ctctctgctc   960
gtcaccgtgg cttttataat cttctgggtt agatccaaaa gaagccgcct gctcccatag  1020
gattacatga atatgactcc acgccgccct ggccccacaa ggaaacacta ccagccttac  1080
gcaccaccta gagatttcgc tgcctatcgg agcagggtga agtttccag atctgcagat  1140
gcaccagcgt atcagcaggg ccagaaccaa ctgtataacg agctcaacct gggacgcagg  1200
gaagagtatg acgttttgga caagcgcaga ggacgggacc ctgagatggg tggcaaacca  1260
```

```
agacgaaaaa accccagga gggtctctat aatgagctgc agaaggataa gatggctgaa    1320
gcctattctg aaataggcat gaaaggagag cggagaaggg gaaaagggca cgacggtttg    1380
taccagggac tcagcactgc tacgaaggat acttatgacg ctctccacat gcaagccctg    1440
ccacctaggt ag                                                        1452
```

<210> SEQ ID NO 34
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 34

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Ser Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
```

```
                    325                 330                 335
Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
            355                 360                 365

Tyr Arg Ser Arg Val Lys Phe Ser Arg Ser Ala Asp Ala Pro Ala Tyr
        370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 35
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 35
atggcactcc ccgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc agtagctatg catgcactgg gtccgccag    180 gctccaggca aggggctgga gtgggtggca gttatatcgt atgatggaag taataaatac   240
tatgcagact ccgtgaaggg ccgattcacc atctccagag acaattccaa gaacacgctg   300
tatctgcaaa tgaacagcct gagagccgag gacacggcgg tgtactactg cgtcaagggg   360
ccgttgcagg agccgccata cgattatgga atggacgtat ggggccaggg aacaactgtc   420
accgtctcct cagggtctac atccggctcc gggaagcccg aagtggcga aggtagtaca   480 aagggggaaa tagtgatgac gcagtctcca gccaccctgt ctgtgtctcc aggggaaaga   540
gccaccctct cctgcagggc cagtcagagt gttagcagca acttagcctg gtaccagcag   600
aaacctggcc aggctcccag gctcctcatc tatagcgcat ccaccagggc cactggtatc   660
ccagccaggt tcagtggcag tgggtctggg acagagttca ctctcaccat cagcagcctg   720
cagtctgaag attttgcagt ttattactgt cagcagcacc acgtctggcc tctcactttt   780
ggcggaggga ccaaggttga gatcaaacgg gccgctgccc ttgataatga aaagtcaaac   840
ggaacaatca ttcacgtgaa gggcaagcac ctcgacccgt cacccttgtt ccctggtcca   900
tccaagccat tctgggtgtt ggtcgtagtg gtggagtcc tcgcttgtta ctctctgctc    960
gtcaccgtgg ctttttataat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
```

-continued

```
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa acccccagga gggtctctat aatgagctgc agaaggataa gatggctgaa   1320
gcctattctg aaataggcat gaaaggagag cggagaaggg gaaaagggca cgacggtttg   1380
taccagggac tcagcactgc tacgaaggat acttatgacg ctctccacat gcaagccctg   1440
ccacctaggt ag                                                        1452

<210> SEQ ID NO 36
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 36

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Asp Pro Ser Pro Leu Phe Pro Gly Pro Ser Lys Pro Phe
    290                 295                 300
```

```
Trp Val Leu Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
            325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
            355                 360                 365

Tyr Arg Ser Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 37
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 37
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg gcatgcactg ggtccgccag     180
gctccaggca aggggctgga gtgggtggca gttatatcgt atgatggaag taataaatac     240
tatgcagact ccgtgaaggg ccgattcacc atctccagag acaattccaa gaacacgctg     300
tatctgcaaa tgaacagcct gagagccgag gacacggcgg tgtactactg cgtcaagggg     360
ccgttgcagg agccgccata cgattatgga atggacgtat ggggccaggg aacaactgtc     420
accgtctcct cagggtctac atccggctcc ggaagcccg gaagtggcga aggtagtaca     480
aagggggaaa tagtgatgac gcagtctcca gccaccctgt ctgtgtctcc aggggaaaga     540
gccaccctct cctgcagggc cagtcagagt gttagcagca acttagcctg gtaccagcag     600
aaacctggcc aggctcccag gctcctcatc tatagcgcat ccaccagggc cactggtatc     660
ccagccaggt tcagtggcag tgggtctggg acagagttca ctctcaccat cagcagcctg     720
cagtctgaag attttgcagt ttattactgt cagcagcacc acgtctggcc tctcactttt     780
ggcggaggga ccaaggttga gatcaaacgg ccgctgccc ttgataatga aaagtcaaac     840
ggaacaatca ttcacgtgaa gggcaagcac ctctgtccgt cacccttgtt ccctggtcca     900
tccaagccat tctgggtgtt ggtcgtagtg ggtggagtcc tcgctgctta ctctctgctc     960
gtcaccgtgg cttttataat cttctgggtt agatccaaaa gaagccgcct gctccatagc    1020
```

| | |
|---|---|
| gattacatga atatgactcc acgccgccct ggccccacaa ggaaacacta ccagccttac | 1080 |
| gcaccaccta gagatttcgc tgcctatcgg agcagggtga agttttccag atctgcagat | 1140 |
| gcaccagcgt atcagcaggg ccagaaccaa ctgtataacg agctcaacct gggacgcagg | 1200 |
| gaagagtatg acgttttgga caagcgcaga ggacgggacc ctgagatggg tggcaaacca | 1260 |
| agacgaaaaa accccagga gggtctctat aatgagctgc agaaggataa gatggctgaa | 1320 |
| gcctattctg aaataggcat gaaggagag cggagaaggg gaaaagggca cgacggtttg | 1380 |
| taccagggac tcagcactgc tacgaaggat acttatgacg ctctccacat gcaagccctg | 1440 |
| ccacctaggt ag | 1452 |

<210> SEQ ID NO 38
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 38

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285
```

```
Lys His Leu Cys Pro Ser Pro Leu Phe Pro Gly Pro Ser Lys Pro Phe
            290                 295                 300
Trp Val Leu Val Val Val Gly Gly Val Leu Ala Ala Tyr Ser Leu Leu
305                 310                 315                 320
Val Thr Val Ala Phe Ile Ile Phe Trp Val Arg Ser Lys Arg Ser Arg
                325                 330                 335
Leu Leu His Ser Asp Tyr Met Asn Met Thr Pro Arg Arg Pro Gly Pro
            340                 345                 350
Thr Arg Lys His Tyr Gln Pro Tyr Ala Pro Pro Arg Asp Phe Ala Ala
            355                 360                 365
Tyr Arg Ser Arg Val Lys Phe Ser Arg Ser Ala Asp Ala Pro Ala Tyr
370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Arg Gly Arg Asp Pro Glu Met
                405                 410                 415
Gly Gly Lys Pro Arg Arg Lys Asn Pro Gln Glu Gly Leu Tyr Asn Glu
            420                 425                 430
Leu Gln Lys Asp Lys Met Ala Glu Ala Tyr Ser Glu Ile Gly Met Lys
            435                 440                 445
Gly Glu Arg Arg Arg Gly Lys Gly His Asp Gly Leu Tyr Gln Gly Leu
450                 455                 460
Ser Thr Ala Thr Lys Asp Thr Tyr Asp Ala Leu His Met Gln Ala Leu
465                 470                 475                 480
Pro Pro Arg

<210> SEQ ID NO 39
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 39
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg catgcactgg gtccgccag     180
gctccaggca aggggctgga gtgggtggca gttatatcgt atgatggaag taataaatac    240
tatgcagact ccgtgaaggg ccgattcacc atctccagag acaattccaa gaacacgctg    300
tatctgcaaa tgaacagcct gagagccgag gacacggcgg tgtactactg cgtcaagggg    360
ccgttgcagg agccgccata cgattatgga atggacgtat ggggccaggg aacaactgtc    420
accgtctcct cagggtctac atccggctcc gggaagcccg aagtggcga aggtagtaca    480
aagggggaaa tagtgatgac gcagtctcca gccaccctgt ctgtgtctcc aggggaaaga    540
gccaccctct cctgcagggc cagtcagagt gttagcagca cttagcctg gtaccagcag    600
aaacctggcc aggctcccag gctcctcatc tatagcgcat ccaccagggc cactggtatc    660
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg ccgctgccc ttgataatga aaagtcaaac    840
ggaacaatca ttcacgtgaa gggcaagcac ctcgacccgt cacccttgtt ccctggtcca    900
```

```
tccaagccat tctgggtgtt ggtcgtagtg ggtggagtcc tcgctgctta ctctctgctc    960
gtcaccgtgg cttttataat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa accccagga gggtctctat aatgagctgc agaaggataa gatggctgaa   1320
gcctattctg aaataggcat gaaggagag cggagaaggg gaaaagggca cgacggtttg   1380
taccagggac tcagcactgc tacgaaggat acttatgacg ctctccacat gcaagccctg   1440
ccacctaggt ag                                                       1452
```

<210> SEQ ID NO 40
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 40

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
```

```
        260                 265                 270
Ala Leu Asp Asn Glu Lys Ser Asn Gly Thr Ile Ile His Val Lys Gly
            275                 280                 285

Lys His Leu Asp Pro Ser Pro Leu Phe Pro Gly Pro Ser Lys Pro Phe
        290                 295                 300

Trp Val Leu Val Val Val Gly Gly Val Leu Ala Ala Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 41
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 41
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg catgcactgg gtccgccag     180 gctccaggca aggggctgga gtgggtggca gttatatcgt atgatggaag taataaatac     240
tatgcagact ccgtgaaggg ccgattcacc atctccagag acaattccaa gaacacgctg     300
tatctgcaaa tgaacagcct gagagccgag gacacggcgg tgtactactg cgtcaagggg     360
ccgttgcagg agccgccata cgattatgga atggacgtat ggggccaggg aacaactgtc     420
accgtctcct cagggtctac atccggctcc gggaagcccg aagtggcga aggtagtaca     480 aagggggaaa tagtgatgac gcagtctcca gccaccctgt ctgtgtctcc aggggaaaga     540
gccaccctct cctgcagggc cagtcagagt gttagcagca acttagcctg gtaccagcag     600
aaacctggcc aggctcccag gctcctcatc tatagcgcat ccaccagggc cactggtatc     660
ccagccaggt tcagtggcag tgggtctggg acagagttca ctctcaccat cagcagcctg     720
cagtctgaag attttgcagt ttattactgt cagcagcacc acgtctggcc tctcactttt     780
```

```
ggcggaggga ccaaggttga gatcaaacgg ccgctgccc ttgataatga aaagtcaaac    840
ggaacaatca ttcacgtgaa gggcaagcac ctctccccgt cacccttgtt ccctggtcca    900
tccaagccat tctgggtgtt ggtcgtagtg ggtggagtcc tcgctgtata ctctctgctc    960
gtcaccgtgg cttttataat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa accccagga gggtctctat aatgagctgc agaaggataa gatggctgaa   1320
gcctattctg aaataggcat gaaggagag cggagaaggg gaaaagggca cgacggtttg   1380 tacagggac tcagcactgc tacgaaggat acttatgacg ctctccacat gcaagccctg   1440
ccacctaggt ag                                                      1452
```

<210> SEQ ID NO 42
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 42

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240
```

```
Gln Ser Glu Asp Phe Ala Val Tyr Tyr Cys Gln Gln His His Val Trp
            245                 250                 255

Pro Leu Thr Phe Gly Gly Gly Thr Lys Val Glu Ile Lys Arg Ala Ala
        260                 265                 270

Ala Leu Asp Asn Glu Lys Ser Asn Gly Thr Ile Ile His Val Lys Gly
    275                 280                 285

Lys His Leu Ser Pro Ser Pro Leu Phe Pro Gly Pro Ser Lys Pro Phe
290                 295                 300

Trp Val Leu Val Val Val Gly Gly Val Leu Ala Val Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 43
<211> LENGTH: 1452
<212> TYPE: DNA
<213> ORGANISM: Artificial Sequence
<220> FEATURE:
<223> OTHER INFORMATION: POLYPEPTIDE

<400> SEQUENCE: 43
atggcactcc ccgtaactgc tctgctgctg ccgttggcat tgctcctgca cgccgcacgc      60
ccgcaggtgc agctggtgga gtctggggga ggcgtggtcc agcctgggag gtccctgaga     120
ctctcctgtg cagcgtctgg attcaccttc agtagctatg catgcactgg gtccgccag      180 gctccaggca aggggctgga gtgggtggca gttatatcgt atgatggaag taataaatac     240
tatgcagact ccgtgaaggg ccgattcacc atctccagag acaattccaa gaacacgctg     300
tatctgcaaa tgaacagcct gagagccgag gacacggcgg tgtactactg cgtcaagggg     360
ccgttgcagg agccgccata cgattatgga atggacgtat ggggccaggg aacaactgtc     420
accgtctcct cagggtctac atccggctcc gggaagcccg aagtggcga aggtagtaca     480 aaggggaaa tagtgatgac gcagtctcca gccaccctgt ctgtgtctcc aggggaaaga     540
gccaccctct cctgcagggc cagtcagagt gttagcagca acttagcctg gtaccagcag     600
aaacctggcc aggctcccag gctcctcatc tatagcgcat ccaccagggc cactggtatc     660
```

```
ccagccaggt tcagtggcag tgggtctggg acagagttca ctctcaccat cagcagcctg      720
cagtctgaag attttgcagt ttattactgt cagcagcacc acgtctggcc tctcactttt      780
ggcggaggga ccaaggttga gatcaaacgg gccgctgccc ttgataatga aaagtcaaac      840
ggaacaatca ttcacgtgaa gggcaagcac ctcaacgggt cagccttgtt ccctggtcca      900
tccaagccat tctgggtgtt ggtcgtagtg ggtggagtcc tcgctgtata ctctctgctc      960
gtcaccgtgg cttttataat cttctgggtt agatccaaaa gaagccgcct gctccatagc      1020
gattacatga atatgactcc acgccgccct ggccccacaa ggaaacacta ccagccttac      1080
gcaccaccta gagatttcgc tgcctatcgg agcagggtga agttttccag atctgcagat      1140
gcaccagcgt atcagcaggg ccagaaccaa ctgtataacg agctcaacct gggacgcagg      1200
gaagagtatg acgttttgga caagcgcaga ggacgggacc ctgagatggg tggcaaacca      1260
agacgaaaaa accccagga gggtctctat aatgagctgc agaaggataa gatggctgaa      1320
gcctattctg aaataggcat gaaaggagag cggagaaggg gaaaagggca cgacggtttg      1380 tacccaggcga ctcagcactgc tacgaaggat acttatgacg ctctccacat gcaagccctg      1440
ccacctaggt ag                                                          1452
```

<210> SEQ ID NO 44
<211> LENGTH: 483
<212> TYPE: PRT
<213> ORGANISM: Artificial Sequence
<220> FEATURE:
<223> OTHER INFORMATION: POLYPEPTIDE

<400> SEQUENCE: 44

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220
```

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
            245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
            275                 280                 285

Lys His Leu Asn Gly Ser Ala Leu Phe Pro Gly Pro Ser Lys Pro Phe
            290                 295                 300

Trp Val Leu Val Val Val Gly Gly Val Leu Ala Val Tyr Ser Leu Leu
305                 310                 315                 320

Val Thr Val Ala Phe Ile Ile Phe Trp Val Arg Ser Lys Arg Ser Arg
            325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
            355                 360                 365

Tyr Arg Ser Arg Val Lys Phe Ser Arg Ser Ala Asp Ala Pro Ala Tyr
            370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
            450                 455                 460

Ser Thr Ala Thr Lys Asp Thr Tyr Asp Ala Leu His Met Gln Ala Leu
465                 470                 475                 480

Pro Pro Arg

<210> SEQ ID NO 45
<211> LENGTH: 1443
<212> TYPE: DNA
<213> ORGANISM: Artificial Sequence
<220> FEATURE:
<223> OTHER INFORMATION: POLYPEPTIDE

<400> SEQUENCE: 45
atggcactcc ccgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc agtagctatg catgcactgg gtccgccag   180 gctccaggca aggggctgga gtgggtggca gttatatcgt atgatggaag taataaatac   240
tatgcagact ccgtgaaggg ccgattcacc atctccagag acaattccaa gaacacgctg   300
tatctgcaaa tgaacagcct gagagccgag gacacggcgg tgtactactg cgtcaagggg   360
ccgttgcagg agccgccata cgattatgga atggacgtat ggggccaggg aacaactgtc   420
accgtctcct cagggtctac atccggctcc gggaagcccg aagtggcga aggtagtaca   480 aagggggaaa tagtgatgac gcagtctcca gccaccctgt ctgtgtctcc aggggaaaga   540

-continued

```
gccaccctct cctgcagggc cagtcagagt gttagcagca acttagcctg gtaccagcag    600
aaacctggcc aggctcccag gctcctcatc tatagcgcat ccaccagggc cactggtatc    660
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg gccgctgccc ttgataatga aaagtcaaac    840
ggaacaatca ttcacgtgaa gggcaagcac ctctccccgt cacccttgtt ccctggtcca    900
tccaagccag aaatcacact gatcatattt ggtgtaattg ctggcgtcat agggaccatt    960
cttttgatca gttacggaat tagatccaaa agaagccgcc tgctccatag cgattacatg   1020
aatatgactc cacgccgccc tggccccaca aggaaacact accagcctta cgcaccacct   1080
agagatttcg ctgcctatcg gagcaggggtg aagttttcca gatctgcaga tgcaccagcg   1140
tatcagcagg ccagaaccaa actgtataac gagctcaacc tgggacgcag ggaagagtat   1200
gacgttttgg acaagcgcag aggacgggac cctgagatgg gtggcaaacc aagacgaaaa   1260
aacccccagg agggtctcta taatgagctg cagaaggata gatggctgaa gcctattct    1320 gaaataggca tgaaggaga gcggagaagg ggaaaagggc acgacggttt gtaccaggga   1380
ctcagcactg ctacgaagga tacttatgac gctctccaca tgcaagccct gccacctagg   1440
tag                                                                 1443
```

<210> SEQ ID NO 46
<211> LENGTH: 480
<212> TYPE: PRT
<213> ORGANISM: Artificial Sequence
<220> FEATURE:
<223> OTHER INFORMATION: POLYPEPTIDE

<400> SEQUENCE: 46

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
```

```
                195                 200                 205
Leu Ile Tyr Ser Ala Ser Thr Arg Ala Thr Gly Ile Pro Ala Arg Phe
        210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
        260                 265                 270

Ala Leu Asp Asn Glu Lys Ser Asn Gly Thr Ile Ile His Val Lys Gly
        275                 280                 285

Lys His Leu Ser Pro Ser Pro Leu Phe Pro Gly Pro Ser Lys Pro Glu
        290                 295                 300

Ile Thr Leu Ile Ile Phe Gly Val Ile Ala Gly Val Ile Gly Thr Ile
305                 310                 315                 320

Leu Leu Ile Ser Tyr Gly Ile Arg Ser Lys Arg Ser Arg Leu Leu His
                325                 330                 335

Ser Asp Tyr Met Asn Met Thr Pro Arg Arg Pro Gly Pro Thr Arg Lys
        340                 345                 350

His Tyr Gln Pro Tyr Ala Pro Pro Arg Asp Phe Ala Ala Tyr Arg Ser
        355                 360                 365

Arg Val Lys Phe Ser Arg Ser Ala Asp Ala Pro Ala Tyr Gln Gln Gly
        370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
        420                 425                 430

Asp Lys Met Ala Glu Ala Tyr Ser Glu Ile Gly Met Lys Gly Glu Arg
        435                 440                 445

Arg Arg Gly Lys Gly His Asp Gly Leu Tyr Gln Gly Leu Ser Thr Ala
        450                 455                 460

Thr Lys Asp Thr Tyr Asp Ala Leu His Met Gln Ala Leu Pro Pro Arg
465                 470                 475                 480

<210> SEQ ID NO 47
<211> LENGTH: 1443
<212> TYPE: DNA
<213> ORGANISM: Artificial Sequence
<220> FEATURE:
<223> OTHER INFORMATION: POLYPEPTIDE

<400> SEQUENCE: 47
atggcactcc ccgtaactgc tctgctgctg ccgttggcat tgctcctgca cgccgcacgc     60
ccgcaggtgc agctggtgga gtctggggga ggcgtggtcc agcctgggag gtccctgaga    120
ctctcctgtg cagcgtctgg attcaccttc agtagctatg catgcactgg gtccgccag    180 gctccaggca aggggctgga gtgggtggca gttatatcgt atgatggaag taataaatac    240
tatgcagact ccgtgaaggg ccgattcacc atctccagag acaattccaa gaacacgctg    300
tatctgcaaa tgaacagcct gagagccgag gacacggcgg tgtactactg cgtcaagggg    360
ccgttgcagg agccgccata cgattatgga atggacgtat ggggccaggg aacaactgtc    420
accgtctcct cagggtctac atccggctcc gggaagcccg gaagtggcga aggtagtaca    480
```

```
aaggggggaaa tagtgatgac gcagtctcca gccaccctgt ctgtgtctcc aggggaaaga    540
gccaccctct cctgcagggc cagtcagagt gttagcagca acttagcctg gtaccagcag    600
aaacctggcc aggctcccag gctcctcatc tatagcgcat ccaccagggc cactggtatc    660
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg gccgctgccc ttgataatga aaagtcaaac    840
ggaacaatca ttcacgtgaa gggcaagcac ctctccccgt cacccttgtt ccctggtcca    900
tccaagccag aaatcacact gatcatattt ggtgtaatgg ctatagtcat agggaccatt    960
cttttgatca gttacggaat tagatccaaa agaagccgcc tgctccatag cgattacatg   1020
aatatgactc cacgccgccc tggccccaca aggaaacact accagcctta cgcaccacct   1080
agagatttcg ctgcctatcg gagcagggtg aagttttcca gatctgcaga tgcaccagcg   1140
tatcagcagg gccagaacca actgtataac gagctcaacc tgggacgcag ggaagagtat   1200
gacgttttgg acaagcgcag aggacgggac cctgagatgg gtggcaaacc aagacgaaaa   1260 aaccccccagg agggtctcta taatgagctg cagaaggata gatggctga  agcctattct   1320 gaaataggca tgaaaggaga gcggagaagg ggaaaagggc acgacggttt gtaccaggga   1380
ctcagcactg ctacgaagga tacttatgac gctctccaca tgcaagccct gccacctagg   1440
tag                                                                 1443
```

<210> SEQ ID NO 48
<211> LENGTH: 480
<212> TYPE: PRT
<213> ORGANISM: Artificial Sequence
<220> FEATURE:
<223> OTHER INFORMATION: POLYPEPTIDE

<400> SEQUENCE: 48

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190
```

-continued

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
            245                 250                 255

Pro Leu Thr Phe Gly Gly Gly Thr Lys Val Glu Ile Lys Arg Ala Ala
        260                 265                 270

Ala Leu Asp Asn Glu Lys Ser Asn Gly Thr Ile Ile His Val Lys Gly
        275                 280                 285

Lys His Leu Ser Pro Ser Pro Leu Phe Pro Gly Pro Ser Lys Pro Glu
        290                 295                 300

Ile Thr Leu Ile Ile Phe Gly Val Met Ala Ile Val Ile Gly Thr Ile
305                 310                 315                 320

Leu Leu Ile Ser Tyr Gly Ile Arg Ser Lys Arg Ser Arg Leu Leu His
            325                 330                 335

Ser Asp Tyr Met Asn Met Thr Pro Arg Arg Pro Gly Pro Thr Arg Lys
        340                 345                 350

His Tyr Gln Pro Tyr Ala Pro Pro Arg Asp Phe Ala Ala Tyr Arg Ser
        355                 360                 365

Arg Val Lys Phe Ser Arg Ser Ala Asp Ala Pro Ala Tyr Gln Gln Gly
        370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
            405                 410                 415

Pro Arg Arg Lys Asn Pro Gln Glu Gly Leu Tyr Asn Glu Leu Gln Lys
        420                 425                 430

Asp Lys Met Ala Glu Ala Tyr Ser Glu Ile Gly Met Lys Gly Glu Arg
        435                 440                 445

Arg Arg Gly Lys Gly His Asp Gly Leu Tyr Gln Gly Leu Ser Thr Ala
        450                 455                 460

Thr Lys Asp Thr Tyr Asp Ala Leu His Met Gln Ala Leu Pro Pro Arg
465                 470                 475                 480

<210> SEQ ID NO 49
<211> LENGTH: 1449
<212> TYPE: DNA
<213> ORGANISM: Artificial Sequence
<220> FEATURE:
<223> OTHER INFORMATION: POLYPEPTIDE

<400> SEQUENCE: 49
atggcactcc ccgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc agtagctatg gcatgcactg ggtccgccag   180
gctccaggca aggggctgga gtgggtggca gttatatcgt atgatggaag taataaatac   240
tatgcagact ccgtgaaggg ccgattcacc atctccagag acaattccaa gaacacgctg   300
tatctgcaaa tgaacagcct gagagccgag gacacggcgg tgtactactg cgtcaagggg   360
ccgttgcagg agccgccata cgattatgga atggacgtat ggggccaggg aacaactgtc   420

```
accgtctcct cagggtctac atccggctcc gggaagcccg gaagtggcga aggtagtaca    480
aaggggggaaa tagtgatgac gcagtctcca gccaccctgt ctgtgtctcc aggggaaaga   540
gccaccctct cctgcagggc cagtcagagt gttagcagca acttagcctg gtaccagcag    600
aaacctggcc aggctcccag gctcctcatc tatagcgcat ccaccagggc cactggtatc    660
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg gccgctgccc ttgataatga aagtcaaac    840
ggaacaatca ttcacgtgaa gggcaagcac ctctccccgt cacccttgtt ccctggtcca    900
tccaagccac ttacgagcat aatctctgcc gttgtaggca tacttctggt ggttgtgctt    960
ggagttgtat tcggtatcct tataaaaaga tccaaaagaa gccgcctgct ccatagcgat   1020
tacatgaata tgactccacg ccgccctggc cccacaagga acactacca gccttacgca   1080
ccacctagag atttcgctgc ctatcggagc agggtgaagt tttccagatc tgcagatgca   1140
ccagcgtatc agcagggcca gaaccaactg tataacgagc tcaacctggg acgcagggaa   1200
gagtatgacg ttttggacaa gcgcagagga cgggaccctg agatgggtgg caaaccaaga   1260
cgaaaaaacc cccaggaggg tctctataat gagctgcaga aggataagat ggctgaagcc   1320
tattctgaaa taggcatgaa aggagagcgg agaaggggaa aagggcacga cggtttgtac   1380
cagggactca gcactgctac gaaggatact tatgacgctc tccacatgca agccctgcca   1440
cctaggtag                                                            1449

<210> SEQ ID NO 50
<211> LENGTH: 482
<212> TYPE: PRT
<213> ORGANISM: Artificial Sequence
<220> FEATURE:
<223> OTHER INFORMATION: POLYPEPTIDE

<400> SEQUENCE: 50

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175
```

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Ser Pro Ser Pro Leu Phe Pro Gly Pro Ser Lys Pro Leu
    290                 295                 300

Thr Ser Ile Ile Ser Ala Val Val Gly Ile Leu Leu Val Val Val Leu
305                 310                 315                 320

Gly Val Val Phe Gly Ile Leu Ile Lys Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 51
<211> LENGTH: 1449
<212> TYPE: DNA
<213> ORGANISM: Artificial Sequence
<220> FEATURE:
<223> OTHER INFORMATION: POLYPEPTIDE

<400> SEQUENCE: 51
atggcactcc cgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc agtagctatg catgcactg ggtccgccag    180 gctccaggca aggggctgga gtgggtggca gttatatcgt atgatggaag taataaatac   240
tatgcagact ccgtgaaggg ccgattcacc atctccagag acaattccaa gaacacgctg   300

-continued

```
tatctgcaaa tgaacagcct gagagccgag gacacggcgg tgtactactg cgtcaagggg    360
ccgttgcagg agccgccata cgattatgga atggacgtat ggggccaggg aacaactgtc    420
accgtctcct cagggtctac atccggctcc gggaagcccg gaagtggcga aggtagtaca    480 aaggggaaa tagtgatgac gcagtctcca gccaccctgt ctgtgtctcc aggggaaaga    540
gccaccctct cctgcagggc cagtcagagt gttagcagca acttagcctg gtaccagcag    600
aaacctggcc aggctcccag gctcctcatc tatagcgcat ccaccagggc cactggtatc    660
ccagccaggt tcagtggcag tgggtctggg acagagttca ctctcaccat cagcagcctg    720
cagtctgaag attttgcagt ttattactgt cagcagcacc acgtctggcc tctcactttt    780
ggcggaggga ccaaggttga gatcaaacgg gccgctgccc ttgataatga aaagtcaaac    840
ggaacaatca ttcacgtgaa gggcaagcac ctctccccgt cacccttgtt ccctggtcca    900
tccaagccac ttacgagcat aatctctgcc gttgtagtga tacttctggt ggttgtgctt    960
ggagttgtat tcgttatcct tataaaaaga tccaaaagaa gccgcctgct ccatagcgat   1020
tacatgaata tgactccacg ccgccctggc cccacaagga acactacca gccttacgca   1080 ccacctagag atttcgctgc ctatcggagc agggtgaagt tttccagatc tgcagatgca   1140
ccagcgtatc agcagggcca gaaccaactg tataacgagc tcaacctggg acgcagggaa   1200
gagtatgacg ttttggacaa gcgcagagga cgggaccctg agatgggtgg caaaccaaga   1260
cgaaaaaacc cccaggaggg tctctataat gagctgcaga aggataagat ggctgaagcc   1320
tattctgaaa taggcatgaa aggagagcgg agaagggaa agggcacga cggtttgtac     1380 cagggactca gcactgctac gaaggatact tatgacgctc tccacatgca agccctgcca   1440
cctaggtag                                                          1449
```

<210> SEQ ID NO 52
<211> LENGTH: 482
<212> TYPE: PRT
<213> ORGANISM: Artificial Sequence
<220> FEATURE:
<223> OTHER INFORMATION: POLYPEPTIDE

<400> SEQUENCE: 52

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160
```

Lys Gly Glu Ile Val Met Thr Gln Ser Pro Ala Thr Leu Ser Val Ser
            165                 170                 175

Pro Gly Glu Arg Ala Thr Leu Ser Cys Arg Ala Ser Gln Ser Val Ser
        180                 185                 190

Ser Asn Leu Ala Trp Tyr Gln Gln Lys Pro Gly Gln Ala Pro Arg Leu
    195                 200                 205

Leu Ile Tyr Ser Ala Ser Thr Arg Ala Thr Gly Ile Pro Ala Arg Phe
210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His His Val Trp
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
        275                 280                 285

Lys His Leu Ser Pro Ser Pro Leu Phe Pro Gly Pro Ser Lys Pro Leu
    290                 295                 300

Thr Ser Ile Ile Ser Ala Val Val Val Ile Leu Leu Val Val Val Leu
305                 310                 315                 320

Gly Val Val Phe Val Ile Leu Ile Lys Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 53
<211> LENGTH: 288
<212> TYPE: DNA
<213> ORGANISM: Artificial Sequence
<220> FEATURE:
<223> OTHER INFORMATION: polypeptide

<400> SEQUENCE: 53
gctgcagcat tgagcaactc aataatgtat tttagtcact ttgtaccagt gttcttgccg      60
gctaagccta ctaccacacc cgctccacgg ccacctaccc cagctcctac catcgcttca     120
cagcctctgt ccctgcgccc agaggcttgc cgaccggccg cagggggcgc tgttcatacc     180

```
agaggactgg atttcgcctg cgatatctat atctgggcac ccctggccgg aacctgcggc    240
gtactcctgc tgtccctggt catcacgctc tattgtaatc acaggaac                 288
```

<210> SEQ ID NO 54
<211> LENGTH: 96
<212> TYPE: PRT
<213> ORGANISM: Artificial Sequence
<220> FEATURE:
<223> OTHER INFORMATION: polypeptide

<400> SEQUENCE: 54

Ala Ala Ala Leu Ser Asn Ser Ile Met Tyr Phe Ser His Phe Val Pro
1               5                   10                  15

Val Phe Leu Pro Ala Lys Pro Thr Thr Thr Pro Ala Pro Arg Pro Pro
            20                  25                  30

Thr Pro Ala Pro Thr Ile Ala Ser Gln Pro Leu Ser Leu Arg Pro Glu
        35                  40                  45

Ala Cys Arg Pro Ala Ala Gly Gly Ala Val His Thr Arg Gly Leu Asp
    50                  55                  60

Phe Ala Cys Asp Ile Tyr Ile Trp Ala Pro Leu Ala Gly Thr Cys Gly
65                  70                  75                  80

Val Leu Leu Leu Ser Leu Val Ile Thr Leu Tyr Cys Asn His Arg Asn
                85                  90                  95

<210> SEQ ID NO 55
<211> LENGTH: 5
<212> TYPE: PRT
<213> ORGANISM: Artificial Sequence
<220> FEATURE:
<223> OTHER INFORMATION: Synthetic

<400> SEQUENCE: 55

Ser Tyr Gly Met His
1               5

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Val Ile Ser Tyr Asp Gly Ser Asn Lys Tyr Tyr Ala Asp Ser Val Lys
1               5                   10                  15

Gly

<210> SEQ ID NO 57
<211> LENGTH: 14
<212> TYPE: PRT
<213> ORGANISM: Artificial Sequence
<220> FEATURE:
<223> OTHER INFORMATION: Synthetic

<400> SEQUENCE: 57

Gly Pro Leu Gln Glu Pro Pro Tyr Asp Tyr Gly Met Asp Val
1               5                   10

<210> SEQ ID NO 58
<211> LENGTH: 11
<212> TYPE: PRT
<213> ORGANISM: Artificial Sequence
<220> FEATURE:

<223> OTHER INFORMATION: Synthetic

<400> SEQUENCE: 58

Arg Ala Ser Gln Ser Val Ser Ser Asn Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Synthetic

<400> SEQUENCE: 59

Ser Ala Ser Thr Arg Ala Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic

<400> SEQUENCE: 60

Gln Gln His His Val Trp Pro Leu Thr
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic

<400> SEQUENCE: 61

Gly Phe Thr Phe Ser Ser Tyr
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic

<400> SEQUENCE: 62

Ser Tyr Asp Gly Ser Asn
1               5

<210> SEQ ID NO 63
<211> LENGTH: 14
<212> TYPE: PRT
<213> ORGANISM: Artificial Sequence
<220> FEATURE:
<223> OTHER INFORMATION: Synthetic

<400> SEQUENCE: 63

Gly Pro Leu Gln Glu Pro Pro Tyr Asp Tyr Gly Met Asp Val
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Synthetic

```
<400> SEQUENCE: 64

Arg Ala Ser Gln Ser Val Ser Ser Asn Leu Ala
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Synthetic

<400> SEQUENCE: 65

Ser Ala Ser Thr Arg Ala Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

Gln Gln His His Val Trp Pro Leu Thr
1               5

<210> SEQ ID NO 67
<211> LENGTH: 24
<212> TYPE: PRT
<213> ORGANISM: Artificial Sequence
<220> FEATURE:
<223> OTHER INFORMATION: Synthetic

<400> SEQUENCE: 67

Glu Ile Thr Leu Ile Ile Phe Gly Val Met Ala Gly Val Ile Gly Thr
1               5                   10                  15

Ile Leu Leu Ile Ser Tyr Gly Ile
            20

<210> SEQ ID NO 68
<211> LENGTH: 26
<212> TYPE: PRT
<213> ORGANISM: Artificial Sequence
<220> FEATURE:
<223> OTHER INFORMATION: Synthetic

<400> SEQUENCE: 68

Leu Thr Ser Ile Ile Ser Ala Val Val Gly Ile Leu Leu Val Val Val
1               5                   10                  15

Leu Gly Val Val Phe Gly Ile Leu Ile Lys
            20                  25
```

What is claimed is:

1. A vector encoding a polypeptide comprising a chimeric antigen receptor (CAR), wherein the CAR comprises
   (i) an antibody or antigen-binding domain selected from the group consisting of single chain fragment (scFv), affibody, Fab fragment, F(ab')2 fragment, and disulfide-linked Fv (sdFv),
   (ii) a transmembrane domain comprising the amino acid sequence of EITLIIFGVMAGVIGTILLISYGI (SEQ ID NO:67) or LTSIISAVVGILLVVVLGVVFGILIK (SEQ ID NO:68), and
   (iii) an intracellular domain.

2. The vector of claim 1, wherein the intracellular domain comprises a signaling region of a protein selected from the group consisting of 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD28, CD276 (B7-H3), CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulatory (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, a Toll ligand receptor, TRANCE/RANKL, VLA1, and VLA-6.

3. The vector of claim 1, wherein the antigen binding domain is in the form of a scFv.

4. The vector of claim 1, wherein the antibody or antigen binding domain specifically binds an antigen selected from the group consisting of 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MuC-1, mutated p53, mutated ras, prostate-specific antigen, ROR1, and VEGFR2, and a combination thereof.

5. A cell comprising the vector of claim 1.

6. A method of making a cell expressing a polypeptide comprising transducing a cell with the vector of claim 1 under suitable conditions.

\* \* \* \* \*